(12) United States Patent
Lou et al.

(10) Patent No.: US 7,208,500 B2
(45) Date of Patent: Apr. 24, 2007

(54) THIENOPYRIDINE-PHENYLACETAMIDES AND THEIR DERIVATIVES USEFUL AS NEW ANTI-ANGIOGENIC AGENTS

(75) Inventors: Jihong Lou, San Diego, CA (US); Robert Steven Kania, San Diego, CA (US); Mingying He, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 75 days.

(21) Appl. No.: 10/928,674

(22) Filed: Aug. 26, 2004

(65) Prior Publication Data
US 2005/0090509 A1    Apr. 28, 2005

Related U.S. Application Data

(60) Provisional application No. 60/499,077, filed on Aug. 29, 2003.

(51) Int. Cl.
C07D 409/02     (2006.01)
A61K 31/381    (2006.01)

(52) U.S. Cl. ........................... 514/301; 546/301
(58) Field of Classification Search ............. 546/114; 514/301
See application file for complete search history.

(56) References Cited

U.S. PATENT DOCUMENTS

| | | | |
|---|---|---|---|
| 5,587,458 A | 12/1996 | King et al. | |
| 5,747,498 A | 5/1998 | Schnur et al. | |
| 5,792,783 A | 8/1998 | Tang et al. | |
| 5,834,504 A | 11/1998 | Tang et al. | |
| 5,861,510 A | 1/1999 | Piscopio et al. | |
| 5,863,949 A | 1/1999 | Robinson et al. | |
| 5,877,305 A | 3/1999 | Huston et al. | |
| 5,883,113 A | 3/1999 | Tang et al. | |
| 5,886,020 A | 3/1999 | Tang et al. | |
| 6,071,935 A | 6/2000 | Lyssikatos | |
| 6,211,164 B1 | 4/2001 | Luo et al. | |
| 6,383,744 B1 | 5/2002 | Green et al. | |
| 6,413,755 B1 | 7/2002 | Luyten et al. | |
| 6,531,491 B1 | 3/2003 | Kania et al. | |
| 6,534,524 B1 | 3/2003 | Kania et al. | |
| 6,995,171 B2 * | 2/2006 | Autry et al. ............ | 514/301 |
| 2001/0046989 A1 | 11/2001 | Levin et al. | |

FOREIGN PATENT DOCUMENTS

| | | |
|---|---|---|
| EP | 606046 | 10/1997 |
| EP | 1086705 | 3/2001 |
| EP | 931788 | 11/2002 |
| WO | WO90/05719 | 5/1990 |
| WO | WO95/19970 | 7/1995 |
| WO | WO95/21613 | 8/1995 |
| WO | WO95/23141 | 8/1995 |
| WO | WO96/14843 | 5/1996 |
| WO | WO96/27583 | 9/1996 |
| WO | WO96/30347 | 10/1996 |
| WO | WO96/33172 | 10/1996 |
| WO | WO96/40142 | 12/1996 |
| WO | WO97/13760 | 4/1997 |
| WO | WO97/13771 | 4/1997 |
| WO | WO97/22596 | 6/1997 |
| WO | WO97/32856 | 9/1997 |
| WO | WO97/34876 | 9/1997 |
| WO | WO97/49688 | 12/1997 |
| WO | WO98/02434 | 1/1998 |
| WO | WO98/02437 | 1/1998 |
| WO | WO98/02438 | 1/1998 |
| WO | WO98/03516 | 1/1998 |
| WO | WO98/07697 | 2/1998 |
| WO | WO98/14451 | 4/1998 |
| WO | WO98/23613 | 6/1998 |
| WO | WO98/30566 | 7/1998 |
| WO | WO98/33768 | 8/1998 |
| WO | WO98/34915 | 8/1998 |
| WO | WO98/34918 | 8/1998 |
| WO | WO98/51344 | 11/1998 |
| WO | WO98/54093 | 12/1998 |

(Continued)

OTHER PUBLICATIONS

Parikh et al., Expression and Regulation of the Novel Vascular Endothelial Growth Factor Receptor Neuropilin-1 by Epidermal Growth Factor in Human Pancreatic Carcinoma, Cancer, 98(4):720-729 (2003).*

(Continued)

*Primary Examiner*—Celia Chang
*Assistant Examiner*—R. James Balls
(74) *Attorney, Agent, or Firm*—Matthew J. Pugmire; Bryan C. Zielinski

(57) ABSTRACT

The invention relates to compounds represented by Formula (I):

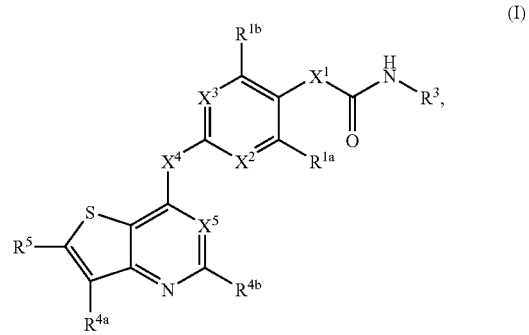

and to prodrugs thereof, pharmaceutically acceptable salts or solvates of said compounds or said prodrugs, wherein each of $X^1$–$X^5$ and $R^1$–$R^5$ are defined herein. The invention also relates to pharmaceutical compositions containing the compounds of Formula (I) and to methods of treating hyperproliferative disorders in a mammal by administering compounds of Formula (I).

32 Claims, No Drawings

FOREIGN PATENT DOCUMENTS

| | | |
|---|---|---|
| WO | WO99/10349 | 3/1999 |
| WO | WO99/16755 | 4/1999 |
| WO | WO99/24440 | 5/1999 |
| WO | WO99/35132 | 7/1999 |
| WO | WO99/35146 | 7/1999 |
| WO | WO 99/46268 | 9/1999 |
| WO | WO99/52889 | 10/1999 |
| WO | WO99/52910 | 10/1999 |
| WO | WO99/61422 | 12/1999 |
| WO | WO 00/00493 | 1/2000 |
| WO | WO00/16781 | 3/2000 |
| WO | WO00/37107 | 6/2000 |
| WO | WO00/38665 | 7/2000 |
| WO | WO00/38715 | 7/2000 |
| WO | WO00/38716 | 7/2000 |
| WO | WO00/38717 | 7/2000 |
| WO | WO00/38718 | 7/2000 |
| WO | WO00/38719 | 7/2000 |
| WO | WO00/38730 | 7/2000 |
| WO | WO00/38786 | 7/2000 |
| WO | WO01/16306 | 3/2001 |
| WO | WO01/21771 | 3/2001 |
| WO | WO01/70268 | 9/2001 |
| WO | WO01/74296 | 10/2001 |
| WO | WO01/74360 | 10/2001 |
| WO | WO01/85796 | 11/2001 |
| WO | WO02/30453 | 4/2002 |
| WO | WO02/41882 | 5/2002 |
| WO | WO02/064170 | 8/2002 |
| WO | WO02/070494 | 9/2002 |
| WO | WO03/006059 | 1/2003 |
| WO | WO 03/009852 A | 2/2003 |
| WO | WO03/035047 | 5/2003 |

OTHER PUBLICATIONS

Sumitomo et al., Immunohistochemical study of fibroblast Growth Factor-2 (FGF-2) and Fibroblast Growth Factor Receptor (FGF-R) in experimental squamous Cell Carcinoma of Rat Submandibular Gland, Oral Oncology 35:98-104 (1999).*

Zhu & Witte, Inhibition of Tumor Growth and Metastasis by Targeting Tumor-Associated Angiogenesis with Antagonists to the Receptors of Vascular Endothelial Growth Factor, Investigational New Drugs, 17:195-212 (1999).*

* cited by examiner

THIENOPYRIDINE-PHENYLACETAMIDES AND THEIR DERIVATIVES USEFUL AS NEW ANTI-ANGIOGENIC AGENTS

This application claims the benefit of U.S. Provisional Application No. 60/499,077, filed Aug. 29, 2003, the disclosure of which is incorporated by reference herein in its entirety.

FIELD OF THE INVENTION

This invention relates to novel thienopyridine-phenylacetamides and derivatives thereof, including pharmaceutically acceptable derivatives, such as salts, prodrugs, solvates, and metabolites. The compounds of the present invention inhibit the activity of receptor kinases such as VEGFR and PDGRF that are required for cell growth and differentiation and angiogenesis. Particularly, the compounds in this invention inhibit VEGFR/KDR and therefore are useful for treatment of diseases and conditions that are associated with VEGFR/KDR activity, e.g., cancer and ophthalmic diseases such as age-related macular degeneration and diabetic retinopathy. This invention also relates to a method of using such compounds in the treatment of hyperproliferative diseases in mammals, especially humans, and to pharmaceutical compositions containing such compounds.

BACKGROUND

A cell may become cancerous by virtue of the transformation of a portion of its DNA into an oncogene (i.e., a gene that upon activation leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors, a transmembrane domain, and an intracellular portion that functions as a kinase to phosphorylate a specific tyrosine residue in proteins and hence to influence cell proliferation. Tyrosine kinases may be classified as growth factor receptor (e.g. EGFR, PDGFR, FGFR and erbB2) or non-receptor (e.g. c-src and bcr-abl) kinases. Such kinases may be aberrantly expressed in common human cancers such as breast cancer, gastrointestinal cancers such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers. Studies indicate that epidermal growth factor receptor (EGFR) is mutated or overexpressed in many human cancers such as brain, lung, squamous cell, bladder, gastric, breast, head and neck, oesophageal, gynecological and thyroid cancers. Thus, inhibitors of receptor tyrosine kinases may be useful as selective inhibitors of the growth of mammalian cancer cells.

EGFR inhibitors may be useful in the treatment of pancreatitis and kidney disease (such as proliferative glomerulonephritis and diabetes-induced renal disease), and may reduce successful blastocyte implantation and therefore may be useful as a contraceptive. See PCT international application publication number WO 95/19970 (published Jul. 27, 1995), hereby incorporated by reference in its entirety.

Polypeptide growth factors, such as vascular endothelial growth factor (VEGF) having a high affinity to the human kinase insert-domain-containing receptor (KDR) or the murine fetal liver kinase 1 (FLK-1) receptor have been associated with the proliferation of endothelial cells and more particularly vasculogenesis and angiogenesis. See PCT international application publication number WO 95/21613 (published Aug. 17, 1995), hereby incorporated by reference in its entirety. Agents that are capable of binding to or modulating the KDR/FLK-1 receptor may be used to treat disorders related to vasculogenesis or angiogenesis, such as diabetes, diabetic retinopathy, age related macular degeneration, hemangioma, glioma, melanoma, Kaposi's sarcoma and ovarian, breast, lung, pancreatic, prostate, colon and epidermoid cancer.

Examples of compounds and methods that reportedly can be used to treat hyperproliferative diseases are disclosed in the following patents and applications: U.S. Pat. Nos. 6,534,524, 6,531,491 and 6,071,935; PCT international patent application publication nos. WO 00/38665 (published Jul. 6, 2001), WO 97/49688 (published Dec. 31, 1997), WO 98/23613 (published Jun. 4, 1998), WO 96/30347 (published Oct. 3, 1996), WO 96/40142 (published Dec. 19, 1996), WO 97/13771 (published Apr. 17, 1997), WO 95/23141 (published Aug. 31, 1995), WO 03/006059 (published Jan. 23, 2003), WO 03/035047 (published May 1, 2003), WO 02/064170 (published Aug. 22, 2002), WO 02/41882 (published May 30, 2002), WO 02/30453 (published Apr. 18, 2002), WO 01/85796 (published Nov. 15, 2001), WO 01/74360 (published Oct. 11, 2001), WO 01/74296 (published Oct. 11, 2001), WO 01/70268 (published Sep. 27, 2001) and WO 98/51344 (published Nov. 19, 1998); and European patent publication number EP 1086705 (published Mar. 28, 2001). The foregoing patent and applications are each incorporated herein by reference in their entirety.

SUMMARY

Described herein are compounds capable of modulating the activity of receptor kinases such as VEGFR and PDGRF and methods for utilizing such modulation in the treatment of cancer and other proliferative disorders. Also described are compounds that mediate and/or inhibit the activity of protein kinases, and pharmaceutical compositions containing such compounds. Also described are therapeutic or prophylactic use of such compounds and compositions, and methods of treating cancer as well as other diseases associated with unwanted angiogenesis and/or cellular proliferation, by administering effective amounts of such compounds.

In one aspect are novel thienopyridine-phenylacetamide compounds. In another aspect of the present invention are compounds that modulate the activity of receptor kinases such as KDR/VEGFR2 kinase in vitro and/or in vivo. According to a further aspect of the present invention are compounds that can selectively modulate the activity of receptor kinases such as KDR/VEGFR2 kinase. In yet another aspect of the present invention, provided are pharmaceutical compositions of such VEGFR2-modulating compounds, including pharmaceutically acceptable prodrugs, pharmaceutically acceptable solvates, pharmaceutically active metabolites, or pharmaceutically acceptable salts thereof. According to yet another aspect of the present invention, provided are syntheses schemes for the preparation of such VEGFR2-modulating compounds, and pharmaceutically acceptable prodrugs, pharmaceutically acceptable solvates, pharmaceutically active metabolites, or pharmaceutically acceptable salts thereof. In yet another aspect of the present invention, methods are provided for modulating KDR/VEGFR2 kinase which comprise contacting the VEGFR2-modulating compounds, or pharmaceutically acceptable prodrugs, pharmaceutically acceptable solvates, pharmaceutically active metabolites, or pharmaceutically acceptable salts thereof, described herein, with KDR/VEGFR2 kinase. In yet another aspect of the present invention, provided are methods for treating patients comprising administering a therapeutically effective amount of a VEGFR2-modulating compound, or a pharmaceutically acceptable prodrug, pharmaceutically acceptable solvate, pharmaceutically active metabolite, or pharmaceutically acceptable salt thereof. In yet another aspect of the present invention, are combination therapies involving administration of an anti-neoplastic agent and an effective amount of a VEGFR2-modulating compound, or a pharmaceutically acceptable prodrug, pharmaceutically acceptable solvate, pharmaceutically active metabolite, or pharmaceutically acceptable salt thereof.

In one aspect are compounds of Formula (I):

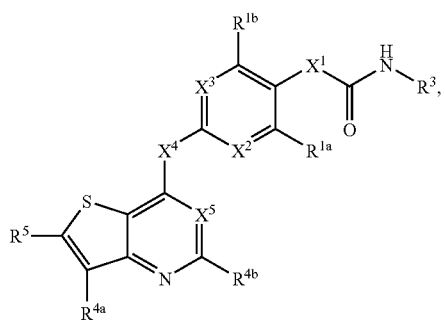

(I)

wherein (a) $X^1$ is O or $CR^{2a}R^{2b}$.

(b) $X^2$ is N or $CR^{1c}$;

(c) $X^3$ is N or $CR^{1d}$;

(d) $X^4$ is O or S;

(e) $X^5$ is N or $CR^{4c}$;

(f) each of $R^{1a}$, $R^{1b}$, $R^{1c}$, and $R^{1d}$ is independently selected from the group consisting of hydrogen, halogen, $(C_1-C_6)$alkoxy, $(C_1-C_6)$alkyl, $(C_1-C_6)$fluoroalkoxy, and $(C_1-C_6)$fluoroalkyl;

(g) each of $R^{2a}$ and $R^{2b}$ is independently selected from H, halogen, or a moiety, optionally substituted with 1 to 3 independently selected $Y^1$ groups, selected from the group consisting of $(C_1-C_6)$alkoxy, $(C_1-C_6)$alkylamine and $(C_1-C_6)$alkyl, wherein any number of the hydrogen atoms on the $(C_1-C_6)$alkoxy and $(C_1-C_6)$alkyl groups may be optionally replaced with F; or $R^{2a}$ and $R^{2b}$ together can be oxo or a moiety, optionally substituted with 1 to 3 independently selected $Y^1$ groups, selected from the group consisting of $(C_3-C_6)$cycloalkyl, 3–6 membered heterocycloalkyl and =CH—$(C_1$ to $C_5$)alkyl;

(h) $R^3$ is H or a moiety, optionally substituted with 1–3 independently selected $Y^2$ groups, selected from the group consisting of —$(CZ^1Z^2)_s$CN, —$(CZ^1Z^2)_s$—$(C_3-C_8)$cycloalkyl, —$(CZ^1Z^2)_s$—$(C_5-C_8)$cycloalkenyl, $(C_2-C_6)$alkenyl, $(C_2-C_6)$alkynyl, —$(CZ^1Z^2)_s$-aryl, —$(CZ^1Z^2)_s$-heterocycle, and $(C_1-C_8)$alkyl, where s is 0, 1, 2, or 3, and wherein when s is 2 or 3, the $CZ^1Z^2$ units may be the same or different;

(i) each of $R^{4a}$, $R^{4b}$, and $R^{4c}$ is independently selected from the group consisting of H, F, Cl, $CF_3$, $CH_3$, $OCH_3$, and $OCF_3$;

(j) $R^5$ is selected from the group consisting of hydrogen, nitro, halogen, azido, —$NR^{6a}R^{6b}$, —$NR^{6a}SO_2R^{6b}$, —$NR^{6a}C(O)R^{6b}$, —$OC(O)R^{6b}$, —$NR^{6a}C(O)OR^{6b}$, —$OC(O)NR^{6a}R^{6b}$, —$OR^{6a}$, —$SR^a$, —$S(O)R^{6a}$, —$SO_2R^{6a}$, —$SO_3R^{6a}$, —$SO_2NR^{6a}R_{6b}$, —$COR^{6a}$, —$CO_2R^{6a}$, —$CONR^{6a}R^{6b}$, —$(C_1-C_4)$fluoroalkyl, —$(C_1-C_4)$fluoroalkoxy, —$(CZ^3Z^4)_t$CN, and a moiety selected from the group consisting of —$(CZ^3Z^4)_t$-aryl, —$(CZ^3Z^4)_t$-heterocycle, $(C_2-C_6)$alkynyl, —$(CZ^3Z^4)_t$—$(C_3-C_6)$cycloalkyl, —$(CZ^3Z^4)_t$—$(C_5-C_6)$cycloalkenyl, $(C_2-C_6)$alkenyl, and $(C_1-C_6)$alkyl, which is optionally substituted with 1 to 3 independently selected $Y^2$ groups, where t is 0, 1, 2, or 3, and wherein when t is 2 or 3, the $CZ^3Z^4$ units may be the same or different;

(k) each $R^{6a}$ and $R^{6b}$ is independently selected from the group consisting of hydrogen and a moiety selected from the group consisting of —$(CZ^5Z^6)_u$—$(C_3-C_6)$cycloalkyl, —$(CZ^5Z^6)_u$—$(C_5-C_6)$cycloalkenyl, —$(CZ^5Z^6)_u$-aryl, —$(CZ^5Z^6)_u$-heterocycle, $(C_2-C_6)$alkenyl, and $(C_1-C_6)$alkyl, which is optionally substituted with 1 to 3 independently selected $Y^3$ groups, where u is 0, 1, 2, or 3, and wherein when u is 2 or 3, the $CZ^5Z^6$ units may be the same or different, or $R^{6a}$ and $R^{6b}$ taken together can with adjacent atoms form a heterocycle;

(l) each $Z^1$, $Z^2$, $Z^3$, $Z^4$, $Z^5$, and $Z^6$ is independently selected from the group consisting of H, F, and $(C_1-C_6)$alkyl, or each $Z^1$ and $Z^2$, $Z^3$ and $Z^4$, or $Z^5$ and $Z^6$ are selected together to form a carbocycle, or two $Z^1$, $Z^3$ or $Z^3$ groups on adjacent carbon atoms are selected together to optionally form a carbocycle; and (m) each $Y^1$ is independently selected from the group consisting of halogen, cyano, nitro, azido, —OH, —$NH_2$, $(C_1-C_6)$alkoxy, $(C_1-C_6)$alkylamino, $(C_1-C_6)$dialkylamino, $(C_1-C_6)$alkyl, $(C_2-C_6)$alkenyl, $(C_2-C_6)$alkynyl, $(C_1-C_6)$haloalkyl, $(C_1-C_6)$haloalkoxy, —$(C_3-C_6)$cycloalkyl;

(n) each $Y^2$ and $Y^3$ is independently selected and (i) is selected from the group consisting of halogen, cyano, nitro, tetrazolyl, guanidino, amidino, methylguanidino, azido, —$C(O)Z^7$, —$OC(O)NH_2$, —$OC(O)NHZ^7$, —$OC(O)NZ^7Z^8$, —$NHC(O)Z^7$, —$NHC(O)NH_2$, —$NHC(O)NHZ^7$, —$NHC(O)NZ^7Z^8$, —$C(O)OH$, —$C(O)OZ^7$, —$C(O)NH_2$, —$C(O)NHZ^7$, —$C(O)NZ^7Z^8$, —$P(O)_3H_2$, —$P(O)_3(Z^7)_2$, —$S(O)_3H$, —$S(O)Z^7$, —$S(O)_2Z^7$, —$S(O)_3Z^7$, —$Z^7$, —$OZ^7$, —OH, —$NH_2$, —$NHZ^7$, —$NZ^7Z^8$, —$C(=NH)NH_2$, —$C(=NOH)NH_2$, —N-morpholino, $(C_2-C_6)$alkenyl, $(C_2-C_6)$alkynyl, $(C_1-C_6)$haloalkyl, $(C_2-C_6)$haloalkenyl, $(C_2-C_6)$haloalkynyl, $(C_1-C_6)$haloalkoxy, —$(CZ^9Z^{10})_r$NH_2$, —$(CZ^9Z^{10})_r$NHZ^3$, —$(CZ^9Z^{10})_r$NZ^7Z^8$—$X^6(CZ^9Z^{10})_r$—$(C_3-C_8)$cycloalkyl, —$X^6(CZ^9Z^{10})_r$—$(C_5-C_8)$cycloalkenyl, —$X^6$ $(CZ^9Z^{10})_r$-aryl, and —$X^6(CZ^9Z^{10})_r$-heterocycle; r is 1, 2, 3, or 4; $X^6$ is O, S, NH, —C(O)—, —C(O)NH—, —C(O)O—, —S(O)—, —$S(O)_2$—, or —$S(O)_3$—; $Z^7$ and $Z^8$ are independently selected from the group consisting of alkyl of 1 to 12 carbon atoms, alkenyl of 2 to 12 carbon atoms, alkynyl of 2 to 12 carbon atoms, cycloalkyl of 3 to 8 carbon atoms, cycloalkenyl of 5 to 8 carbon atoms, aryl of 6 to 14 carbon atoms, heterocycle of 5 to 14 ring atoms, aralkyl of 7 to 15 carbon atoms, and heteroaralkyl of 5 to 14 ring atoms, or $Z^7$ and $Z^8$ together may optionally form a heterocycle; and $Z^9$ and $Z^{10}$ are independently selected from the group consisting of hydrogen, fluorine, alkyl of 1 to 12 carbon atoms, aryl of 6 to 14 carbon atoms, heteroaryl of about 5 to 14 ring atoms, aralkyl of 7 to 15 carbon atoms, and heteroaralkyl of 5 to 14 ring atoms, or $Z^9$ and $Z^{10}$ are selected together to form a carbocycle, or two $Z^9$ groups on adjacent carbon atoms are selected together to form a carbocycle; or (ii) any two $Y^2$ or $Y^3$ groups attached to adjacent carbon atoms may be selected together to be —O[C($Z^9$)($Z^{10}$)]$_r$—O— or —O[C($Z^9$)($Z^{10}$)]$_{r+1}$—; or (iii) any two $Y^2$ or $Y^3$ groups attached to the same or adjacent carbon atoms may be selected together to form a carbocycle or heterocycle;

and wherein any of the above-mentioned substituents comprising a CH$_3$ (methyl), CH$_2$ (methylene), or CH (methine) group which is not attached to a halogen, SO or SO$_2$ group or to a N, O or S atom optionally bears on said group a substituent selected from hydroxy, halogen, ($C_1$–$C_4$)alkyl, ($C_1$–$C_4$)alkoxy and —N[($C_1$–$C_4$)alkyl][($C_1$–$C_4$)alkyl];

or an N-oxide, pharmaceutically acceptable prodrug, pharmaceutically active metabolite, pharmaceutically acceptable salt, or pharmaceutically acceptable solvate thereof.

In one embodiment, $X^2$ is CH or $CR^{1c}$; and $X^3$ is CH, or $CR^{1d}$.

In another embodiment, $X^4$ is O. In a particular aspect of this embodiment, $X^2$ is $CR^{1c}$ and $X^3$ is $CR^{1d}$.

In another embodiment, $X^1$ is O. In a particular aspect of this embodiment, $X^4$ is O; $X^2$ is $CR^{1c}$; $X^3$ is $CR^{1d}$ and $X^5$ is CH.

In another embodiment, $X^1$ is CH$_2$. In a particular aspect of this embodiment, $X^4$ is O; $X^2$ is $CR^{1c}$; and $X^3$ is $CR^{1d}$.

In another embodiment $X^5$ is CH. In a particular aspect of this embodiment, $X^1$ is CH$_2$. In another particular aspect of this embodiment, $X^1$ is CH$^2$, $X^4$ is O; $X^2$ is $CR^{1c}$; and $X^3$ is $CR^{1d}$. In another particular aspect of this embodiment, $X^1$ is CH$_2$, $X^4$ is O; $X^2$ is $CR^{1c}$; $X^3$ is $CR^{1d}$ and each of $R^{1a}$, $R^{1b}$, $R^{1c}$, and $R^{1d}$ is independently H, F, or Cl. In another particular aspect of this embodiment, $X^1$ is CH$_2$, $X^4$ is O; $X^2$ is $CR^{1c}$; $X^3$ is $CR^{1d}$, each of $R^{1a}$, $R^{1b}$, $R^{1c}$, and $R^{1d}$ is independently H, F, or Cl, and each of $R^{4a}$, $R^{4b}$, and $R^{4c}$ is independently selected from the group consisting of H or F. In another particular aspect of this embodiment, $X^1$ is CH$_2$, $X^4$ is O; $X^2$ is $CR^{1c}$; $X^3$ is $CR^{1d}$, each of $R^{1a}$, $R^{1b}$, $R^{1c}$, and $R^{1d}$ is independently H, F, or Cl, each of $R^{4a}$, $R^{4b}$, and $R^{4c}$ is independently selected from the group consisting of H or F, and $R^3$ is either (a) a ($C_1$–$C_8$)alkyl, optionally substituted with 1–3 independently selected $Y^2$ groups; or (b) a heterocycle, optionally substituted with 1–3 independently selected $Y^2$ groups. In another particular aspect of this embodiment, $X^1$ is CH$_2$, $X^4$ is O; $X^2$ is $CR^{1c}$; $X^3$ is $CR^{1d}$, each of $R^{1a}$, $R^{1b}$, $R^{1c}$, and $R^{1d}$ is independently H, F, or Cl, each of $R^{4a}$, $R^{4b}$, and $R^{4c}$ is independently selected from the group consisting of H or F, and $R^5$ is either (a) —CONR$^{6a}$R$^{6b}$ or —(CZ$^3$Z$^4$)$_t$-heterocycle.

In another embodiment, $R^3$ is a ($C_1$–$C_8$)alkyl, optionally substituted with 1–3 independently selected $Y^2$ groups.

In another embodiment, $R^3$ is a heterocycle, optionally substituted with 1–3 independently selected $Y^2$ groups.

In another embodiment, $R^5$ is —CONR$^{6a}$R$^{6b}$.

In another embodiment, $R^5$ is a —(CZ$^3$Z$^4$)$_t$-heterocycle.

In another embodiment, $X^5$ is CH; $X^1$ is CH$_2$; $X^4$ is O; $X^2$ is $CR^{1c}$; $X^3$ is $CR^{1d}$; each of $R^{1a}$, $R^{1b}$, $R^{1c}$, and $R^{1d}$ is independently H, F, or Cl; and each of $R^{4a}$, $R^{4b}$, and $R^{4c}$ is independently selected from the group consisting of H or F; and $R^5$ is —CONR$^{6a}$R$^{6b}$.

In another embodiment are compounds having the structure of Formula (I), wherein $X^5$ is CH; $X^1$ is CH$_2$; $X^4$ is O; $X^2$ is $CR^{1c}$; $X^3$ is $CR^{1d}$; each of $R^{1a}$, $R^{1b}$, $R^{1c}$, and $R^{1d}$ is independently H, F, or Cl; and each of $R^{4a}$, $R^{4b}$, and $R^{4c}$ is independently selected from the group consisting of H or F; and $R^5$ is —(CZ$^3$Z$^4$)$_t$-heterocycle.

In another embodiment, $X^3$ is $CR^{1d}$. In a particular aspect of this embodiment, $X^2$ is $CR^{1c}$. In another particular aspect of this embodiment, $X^2$ is $CR^{1c}$ and $X^5$ is $CR^{4c}$. In another particular aspect of this embodiment, $X^2$ is $CR^{1c}$, $X^5$ is $CR^{4c}$, and $X^1$ is $CR^{2a}R^{2b}$. In another particular aspect of this embodiment, $X^2$ is $CR^{1c}$, $X^5$ is $CR^{4c}$, $X^1$ is $CR^{2a}R^{2b}$, and $X^4$ is O. In another particular aspect of this embodiment, $X^2$ is $CR^{1c}$, $X^5$ is $CR^{4c}$, $X^1$ is $CR^{2a}R^{2b}$, $X^4$ is O, and $R^5$ is —C(O)NR$^{6a}$R$^{6b}$ or —(CZ$^3$Z$^4$)$_t$-heterocycle. In another particular aspect of this embodiment, $X^2$ is $CR^{1c}$, $X^5$ is $CR^{4c}$, $X^1$ is $CR^{2a}R^{2b}$, $X^4$ is O, $R^5$ is —C(O)NR$^{6a}$R$^{6b}$ or —(CZ$^3$Z$^4$)$_t$-heterocycle, and $R^3$ is ($C_1$–$C_6$)alkyl or —(CZ$^1$Z$^2$)$_s$heterocycle. In another particular aspect of this embodiment, $X^2$ is $CR^{1c}$, $X^5$ is $CR^{4c}$, $X^1$ is $CR^{2a}R^{2b}$, $X^4$ is O, $R^5$ is —C(O)NR$^{6a}$R$^{6b}$ or —(CZ$^3$Z$^4$)$_t$-heterocycle, and $R^3$ is heteroaryl. In another particular aspect of this embodiment, $X^2$ is $CR^{1c}$, $X^5$ is $CR^{4c}$, $X^1$ is $CR^{2a}R^{2b}$, $X^4$ is O, $R^5$ is —C(O)NR$^{6a}$R$^{6b}$ or heteroaryl, and $R^3$ is heteroaryl. In another particular aspect of this embodiment, $X^2$ is $CR^{1c}$, $X^5$ is $CR^{4c}$, $X^1$ is $CR^{2a}R^{2b}$, $X^4$ is O, $R^5$ is —C(O)N$^{6a}$R$^{6b}$, wherein $R^{6a}$ and $R^{6b}$ taken with the nitrogen atom form a heterocycle or $R^5$ is imidazolye, either optionally substituted with $Y^3$, and $R^3$ is heteroaryl. In another particular aspect of this embodiment, $X^2$ is $CR^{1c}$, $X^5$ is $CR^{4c}$, $X^1$ is $CR^{2a}R^{2b}$, $X^4$ is O, $R^5$ is —C(O)NR$^{6a}$R$^{6b}$, wherein $R^{6a}$ and $R^{6b}$ taken with the nitrogen atom form a heterocycle or $R^5$ is imidazolye, either optionally substituted with $Y^3$, $R^3$ is heteroaryl, and $R^{1a}$, $R^{1b}$, $R^{1c}$, $R^{1d}$, $R^{2a}$, $R^{2b}$, $R^{4a}$, $R^{4b}$ and $R^{4c}$ are each independently hydrogen or halogen. In another particular aspect of this embodiment, $X^2$ is $CR^{1c}$, $X^5$ is $CR^{4c}$, $X^1$ is $CR^{2a}R^{2b}$, $X^4$ is O, $R^5$ is —C(O)NR$^{6a}$R$^{6b}$, wherein $R^{6a}$ and $R^{6b}$ taken with the nitrogen atom form a heterocycle or $R^5$ is imidazolye, either optionally substituted with $Y^3$, $R^3$ is heteroaryl, and $R^{1a}$, $R^{1b}$, $R^{1c}$, $R^{1d}$, $R^{2a}$, $R^{2b}$, $R^{4a}$, $R^{4b}$ and $R^{4c}$ are hydrogen.

In another embodiment, $X^2$ is $CR^{1c}$, $X^3$ is $CR^{1d}$ and $X^5$ is $CR^{4c}$. In a particular aspect of this embodiment, $X^4$ is O. In another particular aspect of this embodiment, $X^4$ is O and $X^1$ is $CR^{2a}R^{2b}$. In another particular aspect of this embodiment, $X^4$ is O, $X^1$ is $CR^{2a}R^{2b}$, and $R^{1a}$, $R^{1b}$, $R^{1c}$, $R^{1d}$, $R^{2a}$, $R^{2b}$, $R^{4a}$, $R^{4b}$ and $R^{4c}$ are each independently hydrogen or halogen. In another particular aspect of this embodiment, $X^4$ is O, $X^1$ is $CR^{2a}R^{2b}$, $R^{1a}$, $R^{1b}$, $R^{1c}$, $R^{1d}$, $R^{2a}$, $R^{2b}$, $R^{4a}$, $R^{4b}$ and $R^{4c}$ are each independently hydrogen or halogen, and $R^5$ is —C(O)NR$^{6a}$R$^{6b}$ or —(CZ$^3$Z$^4$)$_t$-heterocycle. In another particular aspect of this embodiment, $X^4$ is O, $X^1$ is $CR^{2a}R^{2b}$, $R^{1a}$, $R^{1b}$, $R^{1c}$, $R^{1d}$, $R^{2a}$, $R^{2b}$, $R^{4a}$, $R^{4b}$ and $R^{4c}$ are each independently hydrogen or halogen, $R^5$ is —C(O)NR$^{6a}$R$^{6b}$ or —(CZ$^3$Z$^4$)$_t$-heterocycle, and $R^3$ is ($C_1$–$C_6$)alkyl or —(CZ$^1$Z$^2$)$_s$-heterocycle.

In another embodiment, the invention provides a compound of Formula (II):

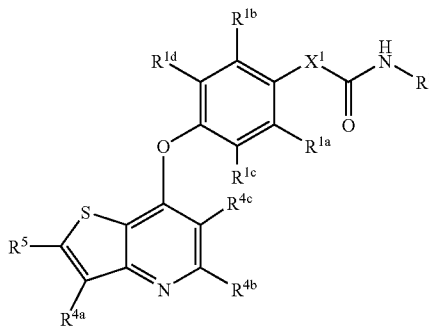

wherein
(a) $X^1$ is O or $CR^{2a}R^{2b}$;
(b) each of $R^{1a}$, $R^{1b}$, $R^{1c}$, and $R^{1d}$ is independently selected from the group consisting of hydrogen, halogen, $(C_1-C_6)$alkoxy, $(C_1-C_6)$alkyl, $(C_1-C_6)$fluoroalkoxy, and $(C_1-C_6)$fluoroalkyl;
(c) each of $R^{2a}$ and $R^{2b}$ is independently selected from H, halogen, or a moiety, optionally substituted with 1 to 3 independently selected $Y^1$ groups, selected from the group consisting of $(C_1-C_6)$alkoxy, $(C_1-C_6)$alkylamine and $(C_1-C_6)$alkyl, wherein any number of the hydrogen atoms on the $(C_1-C_6)$alkoxy and $(C_1-C_6)$alkyl groups may be optionally replaced with F; or $R^{2a}$ and $R^{2b}$ together can be oxo or a moiety, optionally substituted with 1 to 3 independently selected $Y^1$ groups, selected from the group consisting of $(C_3-C_6)$cycloalkyl, 3–6 membered heterocycloalkyl and $=CH-(C_1$ to $C_5)$alkyl;
(d) $R^3$ is H or a moiety, optionally substituted with 1–3 independently selected $Y^2$ groups, selected from the group consisting of $-(CZ^1Z^2)_sCN$, $-(CZ^1Z^2)_s-(C_3-C_8)$cycloalkyl, $-(CZ^1Z^2)_s-(C_5-C_8)$cycloalkenyl, $(C_2-C_6)$alkenyl, $(C_2-C_6)$alkynyl, $-(CZ^1Z^2)_s$-aryl, $-(CZ^1Z^2)_s$-heterocycle, and $(C_1-C_8)$alkyl, where s is 0, 1, 2, or 3, and wherein when s is 2 or 3, the $CZ^1Z^2$ units may be the same or different;
(e) each of $R^{4a}$, $R^{4b}$, and $R^{4c}$ is independently selected from the group consisting of H, F, Cl, $CF_3$, $CH_3$, $OCH_3$, and $OCF_3$;
(f) $R^5$ is selected from the group consisting of hydrogen, nitro, halogen, azido, $-NR^{6a}R^{6b}$, $-NR^{6a}SO_2R^{6b}$, $-NR^{6a}C(O)R^{6b}$, $OC(O)R^{6b}$, $-NR^{6a}C(O)OR^{6b}$, $-OC(O)NR^{6a}R^{6b}$, $-OR^{6a}$, $-SR^{6a}$, $-S(O)R^{6a}$, $-SO_2R^{6a}$, $-SO_3R^{6a}$, $-SO_2NR^{6a}R^{6b}$, $-COR^{6a}$, $-CO_2R^{6a}$, $-CONR^{6a}R^{6b}$, $-(C_1-C_4)$fluoroalkyl, $-(C_1-C_4)$fluoroalkoxy, $-(CZ^3Z^4)_tCN$, and a moiety selected from the group consisting of $-(CZ^3Z^4)_t$-aryl, $-(CZ^3Z^4)_t$-heterocycle, $(C_2-C_6)$alkynyl, $-(CZ^3Z^4)_t-(C_3-C_6)$cycloalkyl, $-(CZ^3Z^4)_t-(C_5-C_6)$cycloalkenyl, $(C_2-C_6)$alkenyl, and $(C_1-C_6)$alkyl, which is optionally substituted with 1 to 3 independently selected $Y^2$ groups, where t is 0, 1, 2, or 3, and wherein when t is 2 or 3, the $CZ^3Z^4$ units may be the same or different;
(g) each $R^{6a}$ and $R^{6b}$ is independently selected from the group consisting of hydrogen and a moiety selected from the group consisting of $-(CZ^5Z^6)_u-(C_3-C_6)$cycloalkyl, $-(CZ^5Z^6)_u-(C_1-C_5)$cycloalkenyl, $-(CZ^5Z^6)_u$-aryl, $-(CZ^5Z^6)_u$-heterocycle, $(C_2-C_6)$alkenyl, and $(C_1-C_6)$alkyl, which is optionally substituted with 1 to 3 independently selected $Y^3$ groups, where u is 0, 1, 2, or 3, and wherein when u is 2 or 3, the $CZ^5Z^6$ units may be same or different, or $R^{6a}$ and $R^{6b}$ taken together can with adjacent atoms form a heterocycle;
(h) each $Z^1$, $Z^2$, $Z^3$, $Z^4$, $Z^5$, and $Z^6$ is independently selected from the group consisting of H, F, and $(C_1-C_6)$alkyl, or each $Z^1$ and $Z^2$, $Z^3$ and $Z^4$, or $Z^5$ and $Z^6$ are selected together to form a carbocycle, or two $Z^1$, $Z^3$ or $Z^3$ groups on adjacent carbon atoms are selected together to optionally form a carbocycle; and
(i) each $Y^1$ is independently selected from the group consisting of halogen, cyano, nitro, azido, $-OH$, $-NH_2$, $(C_1-C_6)$alkoxy, $(C_1-C_6)$alkylamino, $(C_1-C_6)$dialkylamino, $(C_1-C_6)$alkyl, $(C_2-C_6)$alkenyl, $(C_2-C_6)$alkynyl, $(C_1-C_6)$haloalkyl, $(C_1-C_6)$haloalkoxy, $-(C_3-C_6)$cycloalkyl;
(j) each $Y^2$ and $Y^3$ is independently selected and
(i) is selected from the group consisting of halogen, cyano, nitro, tetrazolyl, guanidino, amidino, methylguanidino, azido, $-C(O)Z^7$, $-OC(O)NH_2$, $-OC(O)NHZ^7$, $-OC(O)NZ^7Z^8$, $-NHC(O)Z^7$, $-NHC(O)NH_2$, $-NHC(O)NHZ^7$, $-NHC(O)NZ^7Z^8$, $-C(O)OH$, $-C(O)OZ^7$, $-C(O)NH_2$, $-C(O)NHZ^7$, $-C(O)NZ^7Z^8$, $-P(O)_3H_2$, $-P(O)_3(Z^7)_2$, $-S(O)_3H$, $-S(O)Z^7$, $-S(O)_2Z^7$, $-S(O)_3Z^7$, $-Z^7$, $-OZ^7$, $-OH$, $-NH_2$, $-NHZ^7$, $-NZ^7Z^8$, $-C(=NH)NH_2$, $-C(=NOH)NH_2$, $-N$-morpholino, $(C_2-C_8)$alkenyl, $(C_2-C_6)$alkynyl, $(C_1-C_6)$haloalkyl, $(C_2-C_6)$haloalkenyl, $(C_2-C_6)$haloalkynyl, $(C_1-C_6)$haloalkynyl, $-(CZ^9Z^{10})_rNH_2$, $-(CZ^9Z^{10})_rNHZ^3$, $-(CZ^9Z^{10})_rNZ^7Z^8$, $-X^6(CZ^9Z^{10})_r-(C_3-C_8)$ cycloalkyl, $-X^6(CZ^9Z^{10})_r-(C_5-C_8)$cycloalkenyl, $-X^6(CZ^9Z^{10})_r$-aryl, and $-X^6(CZ^9Z^{10})_r$-heterocycle; r is 1, 2, 3, or 4; $X^6$ is O, S, NH, $-C(O)-$, $-C(O)NH-$, $-C(O)O-$, $-S(O)-$, $-S(O)_2-$, or $-S(O)_3-$; $Z^7$ and $Z^8$ are independently selected from the group consisting of alkyl of 1 to 12 carbon atoms, alkenyl of 2 to 12 carbon atoms, alkynyl of 2 to 12 carbon atoms, cycloalkyl of 3 to 8 carbon atoms, cycloalkenyl of 5 to 8 carbon atoms, aryl of 6 to 14 carbon atoms, heterocycle of 5 to 14 ring atoms, aralkyl of 7 to 15 carbon atoms, and heteroaralkyl of 5 to 14 ring atoms, or $Z^7$ and $Z^8$ together may optionally form a heterocycle; and $Z^9$ and $Z^{10}$ are independently selected from the group consisting of hydrogen, fluorine, alkyl of 1 to 12 carbon atoms, aryl of 6 to 14 carbon atoms, heteroaryl of about 5 to 14 ring atoms, aralkyl of 7 to 15 carbon atoms, and heteroaralkyl of 5 to 14 ring atoms, or $Z^9$ and $Z^{10}$ are selected together to form a carbocycle, or two $Z^9$ groups on adjacent carbon atoms are selected together to form a carbocycle; or
(ii) any two $Y^2$ or $Y^3$ groups attached to adjacent carbon atoms may be selected together to be $-O[C(Z^9)(Z^{10})]_r-O-$ or $-O[C(Z^9)(Z^{10})]_{r+1}-$; or
(iii) any two $Y^2$ or $Y^3$ groups attached to the same or adjacent carbon atoms may be selected together to form a carbocycle or heterocycle;
and wherein any of the above-mentioned substituents comprising a $CH_3$ (methyl), $CH_2$ (methylene), or CH (methine) group which is not attached to a halogen, SO or $SO_2$ group or to a N, O or S atom optionally bears on said group a substituent selected from hydroxy, halogen, $(C_1-C_4)$alkyl, $(C_1-C_4)$alkoxy and $-N[(C_1-C_4)$alkyl][$(C_1-C_4)$alkyl];

or a pharmaceutically acceptable salt or solvate thereof.

Preferred aspects of this embodiment include those described above for Formula I, to the extent not inconsistent with Formula II.

In another embodiment, the invention provides a compound selected from the group consisting of: N-(4,6-Dimethyl-pyridin-2-yl)-2-{3-fluoro-4-[2-(1-methyl-1H-imidazol-2-yl)-thieno[3,2-b]pyridin-7-yloxy]-phenyl}-acetamide,
2-{4-[2-((3R, 4R)-3,4-Dihydroxy-pyrrolidine-1-carbonyl)-thieno[3,2-b]pyridin-7-yloxy]-phenyl}-N-(4,6-dimethyl-pyridin-2-yl)-acetamide,
2-{4-[2-((R)-3-Dimethylamino-pyrrolidine-1-carbonyl)-thieno[3,2-b]pyridin-7-yloxy]-phenyl}-N-(4,6-dimethyl-pyridin-2-yl)-acetamide,
7-{4-[(4,6-Dimethyl-pyridin-2-ylcarbamoyl)-methyl]-phenoxy}-thieno[3,2-b]pyridine-2-carboxylic acid dimethylamide,
N-(4,6-Dimethyl-pyridin-2-yl)-2-{4-[2-(1-methyl-1H-imidazol-2-yl)-thieno[3,2-b]pyridin-7-yloxy]-phenyl}-acetamide,
N-(5-Chloro-pyridin-2-yl)-2-{4-[2-(1-methyl-1H-imidazol-2-yl)-thieno[3,2-b]pyridin-7-yloxy]-phenyl}-acetamide,
N-(4,6-Dimethyl-pyridin-2-yl)-2-{4-[2-((R)-3-hydroxy-pyrrolidine-1-carbonyl)-thieno[3,2-b]pyridin-7-yloxy]-phenyl}-acetamide,
2-{4-[2-((R)-3-Hydroxy-pyrrolidine-1-carbonyl)-thieno[3,2-b]pyridin-7-yloxy]-phenyl}-N-isoquinolin-3-yl-acetamide,
2-{4-[2-((R)-3-Hydroxy-pyrrolidine-1-carbonyl)-thieno[3,2-b]pyridin-7-yloxy]-phenyl}-N-phenyl-acetamide,
2-{4-[2-(Azetidine-1-carbonyl)-thieno[3,2-b]pyridin-7-yloxy]-phenyl}-N-(4,6-dimethyl-pyridin-2-yl)-acetamide,
2-{4-[2-(Azetidine-1-carbonyl)-thieno[3,2-b]pyridin-7-yloxy]-phenyl-N-(6-methyl-pyridin-2-yl)-acetamide,
2-{4-[2-(Azetidine-1-carbonyl)-thieno[3,2-b]pyridin-7-yloxy]-phenyl}-N-(5-trifluoromethyl-pyridin-2-yl)-acetamide,
2-{4-[2-(Azetidine-1-carbonyl)-thieno[3,2-b]pyridin-7-yloxy]-phenyl}-N-(5-chloro-pyridin-2-yl)-acetamide,
2-{4-[2-(Azetidine-1-carbonyl)-thieno[3,2-b]pyridin-7-yloxy]-phenyl}-N-(5-bromo-pyridin-2-yl)-acetamide,
2-{4-[2-(Azetidine-1-carbonyl)-thieno[3,2-b]pyridin-7-yloxy]-phenyl}-N-isoquinolin-3-yl-acetamide,
2-{4-[2-(Azetidine-1-carbonyl)-thieno[3,2-b]pyridin-7-yloxy]-2-chloro-phenyl}-N-(4,6-dimethyl-pyridin-2-yl)-acetamide,
2-{4-[2-(Azetidine-1-carbonyl)-thieno[3,2-b]pyridin-7-yloxy]-2-chloro-phenyl}-N-(5-methyl-1H-pyrazol-3-yl)-acetamide, and
Butyl-carbamic acid 4-[2-(azetidine-1-carbonyl)-thieno[3,2-b]pyridin-7-yloxy]-phenyl ester, or a pharmaceutically acceptable prodrug, pharmaceutically active metabolite, pharmaceutically acceptable solvate or pharmaceutically acceptable salt thereof.

In another embodiment, the invention provides a compound selected from the group consisting of:

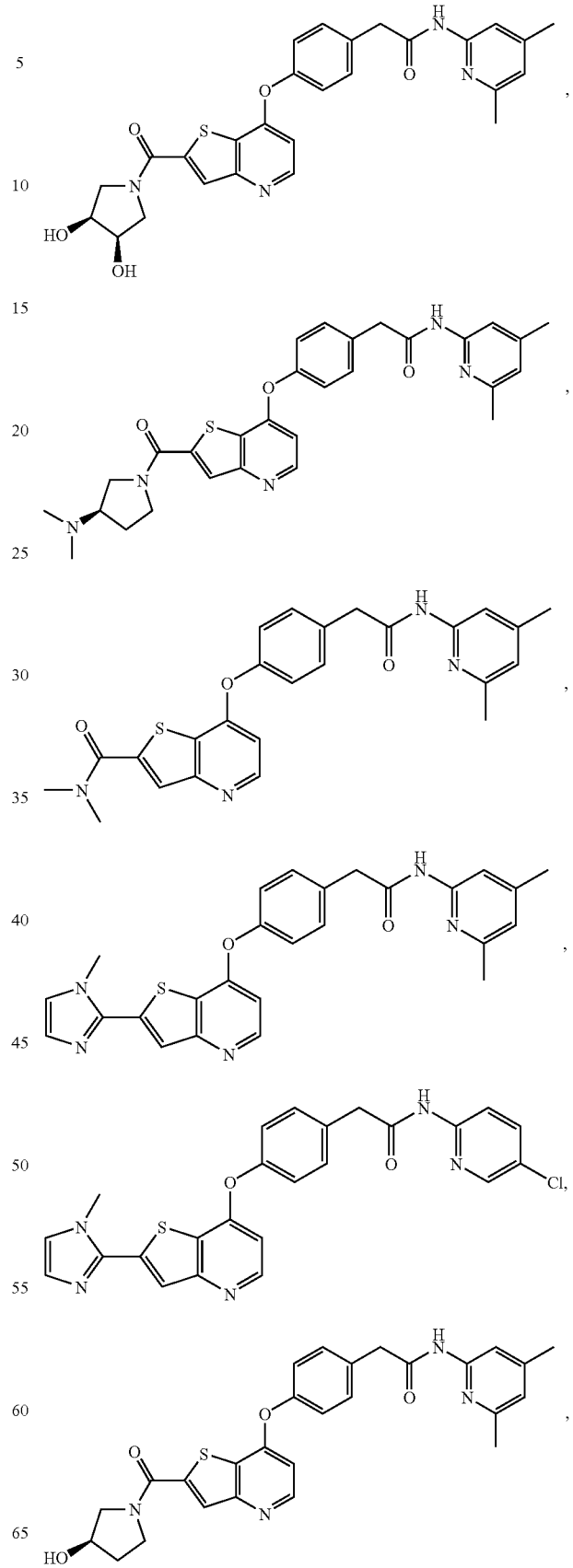

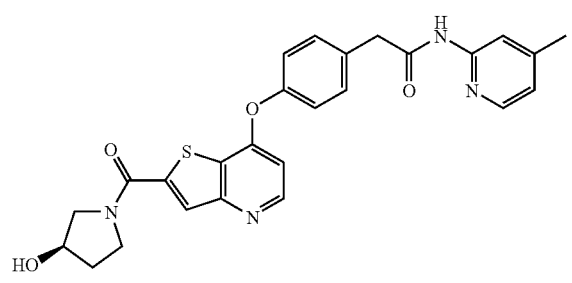,
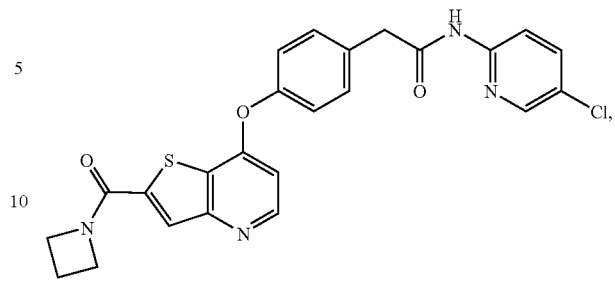,
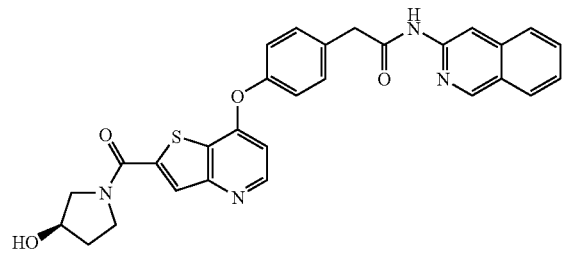,
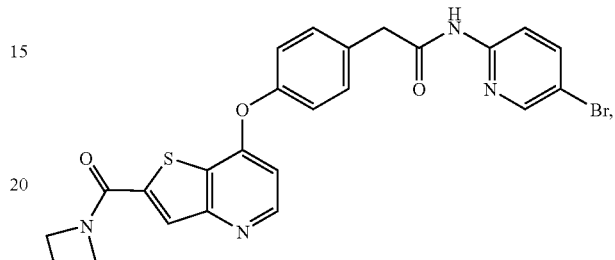,
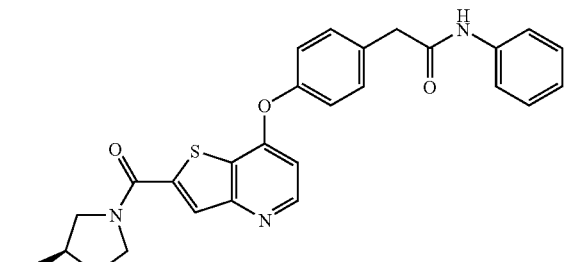,
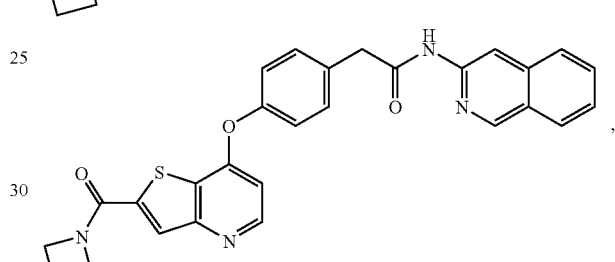,
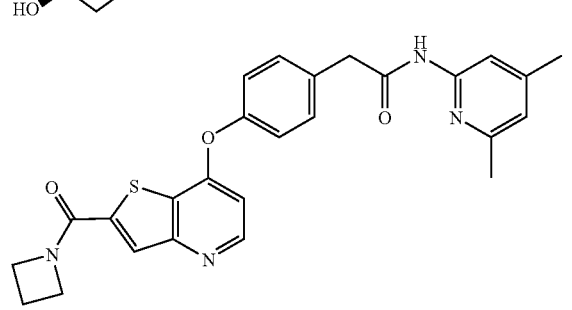,
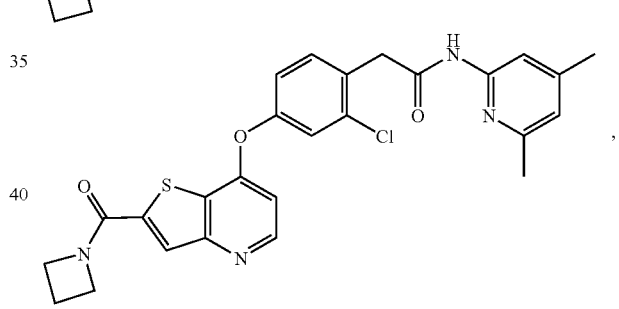,
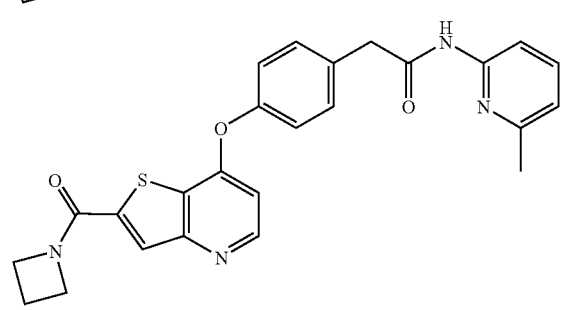,
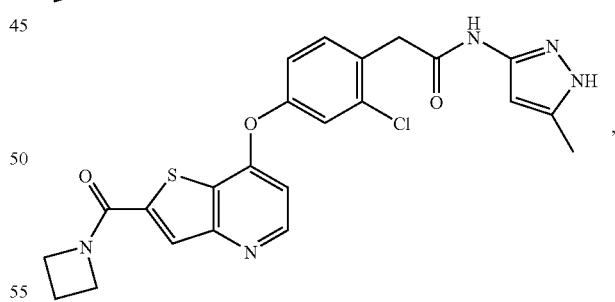,
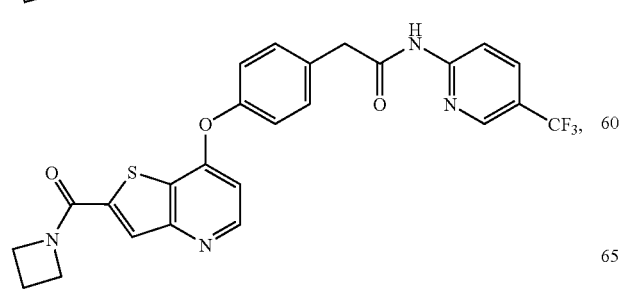,
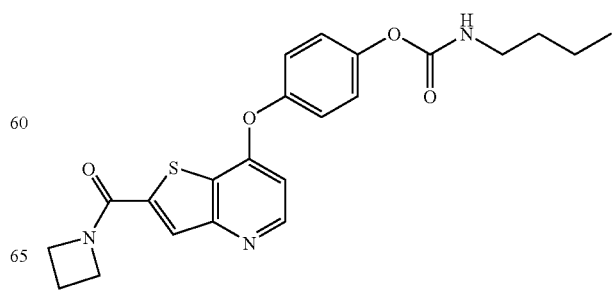

or a pharmaceutically acceptable prodrug, pharmaceutically active metabolite, pharmaceutically acceptable solvate or pharmaceutically acceptable salt thereof.

In another aspect of the present invention are methods for producing a compound having the structure of Formula (I), wherein $X^2$ is $CR^{1c}$, comprising:
(a) reacting a carboxylic acid having the structure

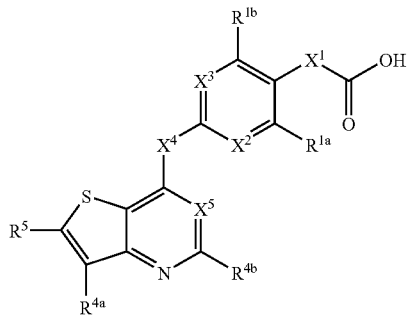

with a chlorinating agent; and
(b) reacting the corresponding product with $H_2N-R^3$. In a further embodiment of this method, the chlorinating agent is selected from the group consisting of thionyl chloride, oxalyl chloride, and chlorine.

In a further embodiment are methods for producing the the carboxylic acid having the structure:

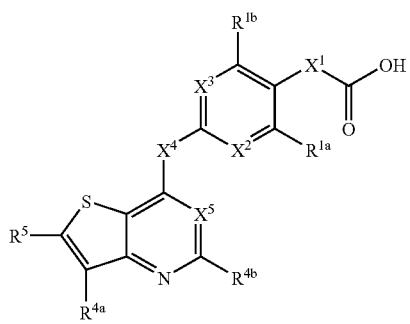

comprising
(a) reacting a compound having the formula

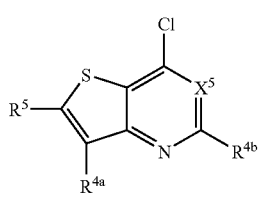

with a compound having the formula

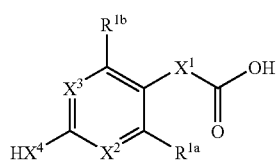

in the presence of a base.

In another embodiment are methods for producing a compound having the structure of Formula (I), wherein $X^2$ is O *?? X4 is O? * comprising
(a) reacting

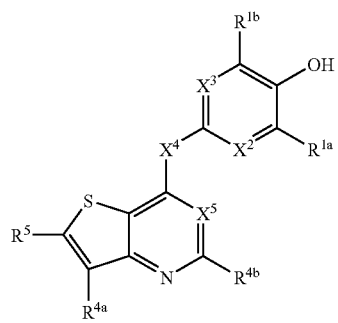

with a carbonyl electrophile; and
(b) reacting the corresponding product with $H_2N-R^3$. In a further embodiment of this method the carbonyl electrophile is phosgene.

This invention also relates to a pharmaceutical composition for the treatment of abnormal cell growth in a mammal, including a human, comprising an amount of a compound of the formula 1, as defined above, or a pharmaceutically acceptable salt, solvate or prodrug thereof, that is effective in treating abnormal cell growth, and a pharmaceutically acceptable carrier. In one embodiment of said composition, said abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said pharmaceutical composition, said abnormal cell growth is a benign proliferative disease, including, but not limited to, psoriasis, benign prostatic hypertrophy or restinosis.

The invention also relates to a pharmaceutical composition for the treatment of abnormal cell growth in a mammal, including a human, which comprises an amount of a compound of formula 1, as defined above, or a pharmaceutically acceptable salt, solvate or prodrug thereof, that is effective in treating abnormal cell growth in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention also relates to a method for the treatment of abnormal cell growth in a mammal, including a human, comprising administering to said mammal an amount of a compound of the formula 1, as defined above, or a pharmaceutically acceptable salt or solvate thereof, that is effective in treating abnormal cell growth. In one embodiment of this method, the abnormal cell growth is cancer, including, but not limited to, lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, chronic or acute leukemia, lymphocytic lymphomas, cancer of the bladder, cancer of the kidney or ureter, renal cell carcinoma, carcinoma of the renal pelvis, neoplasms of the central nervous system (CNS), primary CNS lymphoma, spinal axis tumors, brain stem glioma, pituitary adenoma, or a combination of one or more of the foregoing cancers. In another embodiment of said method, said abnormal cell growth is a benign proliferative disease, including, but not limited to, psoriasis, benign prostatic hypertrophy or restinosis.

This invention also relates to a method for the treatment of a disorder associated with angiogenesis in a mammal, including a human, comprising administering to said mammal an amount of a compound of the formula 1, as defined above, or a pharmaceutically acceptable salt, solvate or prodrug thereof, that is effective in treating said disorder. Such disorders include cancerous tumors such as melanoma; ocular disorders such as age-related macular degeneration, presumed ocular histoplasmosis syndrome, and retinal neovascularization from proliferative diabetic retinopathy; rheumatoid arthritis; bone loss disorders such as osteoporosis, Paget's disease, humoral hypercalcemia of malignancy, hypercalcemia from tumors metastatic to bone, and osteoporosis induced by glucocorticoid treatment; coronary restenosis; and certain microbial infections including those associated with microbial pathogens selected from adenovirus, hantaviruses, *Borrelia burgdorferi, Yersinia* spp., *Bordetella pertussis*, and group A *Streptococcus*.

This invention also relates to a method of (and to a pharmaceutical composition for) treating abnormal cell growth in a mammal which comprise an amount of a compound of formula 1, or a pharmaceutically acceptable salt, solvate or prodrug thereof, in combination with an amount of one or more substances selected from anti-tumor agents, anti-angiogenesis agents, signal transduction inhibitors, and antiproliferative agents, which amounts are together effective in treating said abnormal cell growth. Such substances include those disclosed in PCT publication Nos. WO 00/38715, WO 00/38716, WO 00/38717, WO 00/38718, WO 00/38719, WO 00/38730, WO 00/38665, WO 00/37107 and WO 00/38786, all published on Jul. 6, 2000, the disclosures of which are incorporated herein by reference in their entireties for all purposes.

Anti-tumor agents can be used in conjunction with a compound of formula 1 in the methods and pharmaceutical compositions described herein. Examples of anti-tumor agents include mitotic inhibitors, for example vinca alkaloid derivatives such as vinblastine vinorelbine, vindescine and vincristine; colchines allochochine, halichondrine, N-benzoyltrimethyl-methyl ether colchicinic acid, dolastatin 10, maystansine, rhizoxine, taxanes such as taxol (paclitaxel), docetaxel (Taxotere), 2'-N-[3-(dimethylamino)propyl]glutaramate (taxol derivative), thiocholchicine, trityl cysteine, teniposide, methotrexate, azathioprine, fluorouricil, cytocine arabinoside, 2'2'-difluorodeoxycytidine (gemcitabine), adriamycin and mitamycin. Alkylating agents, for example cis-platin, carboplatin oxiplatin, iproplatin, Ethyl ester of N-acetyl-DL-sarcosyl-L-leucine (Asaley or Asalex), 1,4-cyclohexadiene-1,4-dicarbamic acid, 2,5-bis(1-azirdinyl)-3,6-dioxo-, diethyl ester (diaziquone), 1,4-bis(methanesulfonyloxy)butane (bisulfan or leucosulfan) chlorozotocin, clomesone, cyanomorpholinodoxorubicin, cyclodisone, dianhydroglactitol, fluorodopan, hepsulfam, mitomycin C, hycantheonemitomycin C, mitozolamide, 1-(2-chloroethyl)-4-(3-chloropropyl)-piperazine dihydrochloride, piperazinedione, pipobroman, porfiromycin, spirohydantoin mustard, teroxirone, tetraplatin, thiotepa, triethylenemelamine, uracil nitrogen mustard, bis(3-mesyloxypropyl)amine hydrochloride, mitomycin, nitrosoureas agents such as cyclohexyl-chloroethylnitrosourea, methylcyclohexyl-chloroethylnitrosourea 1-(2-chloroethyl)-3-(2,6-dioxo-3-piperidyl)-1-nitroso-urea, bis(2-chloroethyl)nitrosourea, procarbazine, dacarbazine, nitrogen mustard-related compounds such as mechloroethamine, cyclophosphamide, ifosamide, melphalan, chlorambucil, estramustine sodium phosphate, strptozoin, and temozolamide. DNA anti-metabolites, for example 5-fluorouracil, cytosine arabinoside, hydroxyurea, 2-[(3hydroxy-2-pyrinodinyl)methylene]-hydrazinecarbothioamide, deoxyfluorouridine, 5-hydroxy-2-formylpyridine thiosemicarbazone, alpha-2'-deoxy-6-thioguanosine, aphidicolin glycinate, 5-azadeoxycytidine, beta-thioguanine deoxyriboside, cyclocytidine, guanazole, inosine glycodialdehyde, macbecin II, pyrazolimidazole, cladribine, pentostatin, thioguanine, mercaptopurine, bleomycin, 2-chlorodeoxyadenosine, inhibitors of thymidylate synthase such as raltitrexed and pemetrexed disodium, clofarabine, floxuridine and fludarabine. DNA/RNA antimetabolites, for example, L-alanosine, 5-azacytidine, acivicin, aminopterin and derivatives thereof such as N-[2-chloro-5-[[(2,4-diamino-5-methyl-6-quinazolinyl)methyl]amino] benzoyl]-L-aspartic acid, N-[4-[[(2,4-diamino-5-ethyl-6-quinazolinyl)methyl]amino]benzoyl]-L-aspartic acid, N-[2-chloro-4-[[(2,4-diaminopteridinyl)methyl]amino]benzoyl]-L-aspartic acid, soluble Baker's antifol, dichloroallyl lawsone, brequinar, ftoraf, dihydro-5-azacytidine, methotrexate, N-(phosphonoacetyl)-L-aspartic acid tetrasodium salt, pyrazofuran, trimetrexate, plicamycin, actinomycin D, cryptophycin, and analogs such as cryptophycin-52 or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; proteins, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 in the methods and pharmaceutical compositions described herein. Examples of useful COX-II inhibitors include CELEBREX™ (alecoxib), valdecoxib, and rofecoxib.

Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 331, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are herein incorporated by reference in their entirety. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP4, MMP-5, MMP-6, MMP-7, MMP-8, MMP-10, MMP-11, MMP-12, and MMP-13).

Some specific examples of MMP inhibitors useful in combination with the compounds of the present invention are AG-3340, RO 32-3555, RS 13-0830, and the compounds recited in the following list:

3-[[4-(4-fluoro-phenoxy)-benzenesulfonyl]-(1-hydroxycarbamoyl-cyclopentyl)-amino]-propionic acid;

3-exo-3-[4-(4-fluoro-phenoxy)-benzenesulfonylamino]-8-oxa-bicyclo[3.2.1]octane-3-carboxylic acid hydroxyamide;

(2R, 3R) 1-[4-(2-chloro-4-fluoro-benzyloxy)-benzenesulfonyl]-3-hydroxy-3-methyl-piperidine-2-carboxylic acid hydroxyamide;

4-[4-(4-fluoro-phenoxy)-benzenesulfonylamino]-tetrahydro-pyran-4-carboxylic acid hydroxyamide;

3-[[4-(4-fluoro-phenoxy)-benzenesulfonyl]-(1-hydroxycarbamoyl-cyclobutyl)-amino]-propionic acid;

4-[4-(4-chloro-phenoxy)-benzenesulfonylamino]-tetrahydro-pyran-4-carboxylic acid hydroxyamide;

3-[4-(4-chloro-phenoxy)-benzenesulfonylamino]-tetrahydro-pyran-3-carboxylic acid hydroxyamide;

(2R, 3R) 1-[4-(4-fluoro-2-methyl-benzyloxy)-benzenesulfonyl]-3-hydroxy-3-methyl-piperidine-2-carboxylic acid hydroxyamide;

3-[[4-(4-fluoro-phenoxy)-benzenesulfonyl]-(1-hydroxycarbamoyl-1-methyl-ethyl)-amino]-propionic acid;

3-[[4-(4-fluoro-phenoxy)-benzenesulfonyl]-(4-hydroxycarbamoyl-tetrahydro-pyran-4-yl)-amino]-propionic acid;

3-exo-3-[4-(4-chloro-phenoxy)-benzenesulfonylamino]-8-oxa-bicyclo[3.2.1]octane-3-carboxylic acid hydroxyamide;

3-endo-3-[4-(4-fluoro-phenoxy)-benzenesulfonylamino]-8-oxa-bicyclo[3.2.1]octane-3-carboxylic acid hydroxyamide; and 3-[4-(4-fluoro-phenoxy)-benzenesulfonylamino]-tetrahydro-furan-3-carboxylic acid hydroxyamide;

and pharmaceutically acceptable salts, solvates and prodrugs of said compounds.

Signal transduction inhibitors can be used in conjunction with a compound of formula 1 in the methods and pharmaceutical compositions described herein. Examples of signal transduction inhibitors include agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

VEGF inhibitors, for example SU-5416 and SU-6668 (Sugen Inc. of South San Francisco, Calif., USA), can also be combined with a compound of formula 1. VEGF inhibitors are described in, for example, U.S. Pat. No. 6,534,524, issued Mar. 18, 2003, U.S. Pat. No. 6,531,491, issued Mar. 11, 2003, WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are herein incorporated by reference in their entirety. Other examples of some specific VEGF inhibitors are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.).

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), may be administered in combination with a compound of formula 1. Such erbB2 inhibitors include those described in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), each of which is herein incorporated by reference in its entirety. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are herein incorporated by reference in their entirety.

Other antiproliferative agents that may be used with the compounds of the present invention include inhibitors of the enzyme farnesyl protein transferase and inhibitors of the receptor tyrosine kinase PDGFr, including the compounds disclosed and claimed in the following United States patent applications: Ser. No. 09/221,946 (filed Dec. 28, 1998); Ser. No. 09/454,058 (filed Dec. 2, 1999); Ser. No. 09/501,163 (filed Feb. 9, 2000); Ser. No. 09/539,930 (filed Mar. 31, 2000); Ser. No. 09/202,796 (filed May 22, 1997); Ser. No. 09/384,339 (filed Aug. 26, 1999); and Ser. No. 09/383,755 (filed Aug. 26, 1999); and the compounds disclosed and claimed in the following United States provisional patent applications: No. 60/168,207 (filed Nov. 30, 1999); No. 60/170,119 (filed Dec. 10, 1999); No. 60/177,718 (filed Jan. 21, 2000); No. 60/168,217 (filed Nov. 30, 1999), and No. 60/200,834 (filed May 1, 2000). Each of the foregoing patent applications and provisional patent applications is herein incorporated by reference in their entirety.

A compound of formula 1 may also be used with other agents useful in treating abnormal cell growth or cancer, including, but not limited to, agents capable of enhancing antitumor immune responses, such as CTLA4 (cytotoxic lymphocite antigen 4) antibodies, and other agents capable of blocking CTLA4; and anti-proliferative agents such as other farnesyl protein transferase inhibitors, for example the farnesyl protein transferase inhibitors described in the references cited in the "Background" section, supra. Specific CTLA4 antibodies that can be used in the present invention include those described in U.S. Provisional Application No. 60/113,647 (filed Dec. 23, 1998) which is herein incorporated by reference in its entirety.

The invention also relates to a pharmaceutical composition for the treatment of pancreatitis or kidney disease (including proliferative glomerulonephritis and diabetes-induced renal disease) in a mammal which comprises a therapeutically effective amount of a compound of formula (I), or prodrugs thereof, pharmaceutically active metabolites, pharmaceutically acceptable salts, or pharmaceutically acceptable solvates of said compounds and said prodrugs, and a pharmaceutically acceptable carrier.

The invention also relates to a pharmaceutical composition for the prevention of blastocyte implantation in a mammal which comprises a therapeutically effective amount of a compound of formula (I), or prodrugs thereof, pharmaceutically active metabolites, pharmaceutically acceptable salts, or pharmaceutically acceptable solvates of said compounds and said prodrugs, and a pharmaceutically acceptable carrier.

The invention also relates to a pharmaceutical composition for treating a disease related to vasculogenesis or angiogenesis in a mammal which comprises a therapeutically effective amount of a compound of formula (I), or prodrugs thereof, pharmaceutically active metabolites, pharmaceutically acceptable salts, or pharmaceutically acceptable solvates of said compounds and said prodrugs, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula (I), or prodrugs thereof, pharmaceutically active metabolites, pharmaceutically acceptable salts, or pharmaceutically acceptable solvates of said compounds and said prodrugs in one embodiment, said method relates to the treatment of cancer such as brain, ophthalmic, squamous cell, bladder, gastric, pancreatic, breast, head, neck, oesophageal, prostate, colorectal, lung, renal, kidney, ovarian, gynecological or thyroid cancer. In another embodiment, said method relates to the treatment of a non-cancerous hyperproliferative disorder such as benign hyperplasia of the skin (e.g., psoriasis) or prostate (e.g., BPH).

The invention also relates to a method for the treatment of a hyperproliferative disorder in a mammal which comprises administering to said mammal a therapeutically effective amount of a compound of formula (I), or prodrugs thereof, pharmaceutically active metabolites, pharmaceutically acceptable salts, or pharmaceutically acceptable solvates of said compounds and said prodrugs, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The treatment of a hyperproliferative disorder in a mammal which comprises administering to said mammal a therapeutically effective amount of a VEGF receptor tyrosine kinase inhibitor may lead to a sustained increase in blood pressure. The compounds of the present invention may be used in conjunction with an anti-hypertensive, such as NORVASC or PROCARDIA XL, commercially available from Pfizer, for use in the treatment of a hyperproliferative disorder in a mammal.

This invention also relates to a pharmaceutical composition for treating a disease related to vasculogenesis or angiogenesis in a mammal comprising (a) therapeutically effective amount of a compound of formula (I), or prodrugs thereof, pharmaceutically active metabolites, pharmaceutically acceptable salts, or pharmaceutically acceptable solvates of said compounds and said prodrugs, (b) a therapeutically effective amount of a compound, prodrug, metabolite, salt or solvate of an inhibitor of tumor necrosis factor alpha, and (c) a pharmaceutically acceptable carrier.

This invention also relates to a pharmaceutical composition for treating a disease related to undesired angiogenesis, endothelial cell migration or endothelial cell proliferation in a mammal comprising (a) therapeutically effective amount of a compound of formula (I), or prodrugs thereof, pharmaceutically active metabolites, pharmaceutically acceptable salts, or pharmaceutically acceptable solvates of said compounds and said prodrugs, (b) a therapeutically effective amount of a compound, prodrug, metabolite, salt or solvate of a NADPH oxidase inhibitor, and (c) a pharmaceutically acceptable carrier.

This invention also relates to a pharmaceutical composition for inhibiting abnormal cell growth in a mammal, including a human, comprising an amount of a compound of formula (I), or prodrugs thereof, pharmaceutically active metabolites, pharmaceutically acceptable salts, or pharmaceutically acceptable solvates of said compounds and said prodrugs, that is effective in inhibiting farnesyl protein transferase, and a pharmaceutically acceptable carrier.

This invention also relates to a pharmaceutical composition for inhibiting abnormal cell growth in a mammal which comprises an amount of a compound of formula (I), or prodrugs thereof, pharmaceutically active metabolites, pharmaceutically acceptable salts, or pharmaceutically acceptable solvates of said compounds and said prodrugs, in combination with an amount of a chemotherapeutic, wherein the amounts of the compound, salt, solvate, or prodrug of formula (I), and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, e.g. anti-androgens.

The compounds described herein may be used in a method for preventing or reducing the growth of tumor cells expressing functional VEGF-1 receptors by administering an effective amount of a small molecule VEGF-1 receptor antagonist to inhibit autocrine stimulation and an effective amount of a compound of Formula (I). Active ingredients in such compositions may be present in free form or in the form of a pharmaceutical acceptable salt and optionally at least one pharmaceutically acceptable carrier.

The compounds described herein also may be used in combination with a selective COX-2-inhibitor for simultaneous, separate or sequential use. The compounds described herein may also be used in combination with a truncated, soluble Flkl/KDR receptor to treat a subjects having disease or disorder associated with VEGF. Active ingredients in such compositions may be present in free form or in the form of a pharmaceutical acceptable salt and optionally at least one pharmaceutically acceptable carrier.

The compounds described herein also may be used in combination with a second active ingredient which decreases the activity of, binds to, or inhibits the epidermal growth factor (EGF). Active ingredients in such compositions may be present in free form or in the form of a pharmaceutical acceptable salt and optionally at least one pharmaceutically acceptable carrier.

The compounds described herein also may be used to inhibit VEGF-mediated angiogenesis in a tissue via several methods including but not limited to, contacting the tissue with an inhibitor of NADPH oxidase and an effective amount of a compound of formula 1, by contacting the tissue with an inhibitor of reactive oxygen species (ROS) and an effective amount of a compound of Formula (I), or by contacting the tissue with an inhibitor of superoxide dismutase (SOD) and an effective amount of a compound of formula 1. Active ingredients in such compositions may be present in free form or in the form of a pharmaceutical acceptable salt and optionally at least one pharmaceutically acceptable carrier.

The compounds described herein may also be used in combination with molecules which specifically bind to placenta growth factor in order to suppress or prevent placenta growth factor-induced pathological angiogenesis, vascular leakage (oedema), pulmonary hypertension, tumour formation and/or inflammatory disorders.

The compounds described herein also may be used in combination with molecules chosen from the group comprising: an antibody or any fragment thereof which specifically binds to placenta growth factor, a small molecule specifically binding to placenta growth factor or to vascular endothelial growth factor receptor-1, -vascular endothelial growth factor receptor-1 antagonists or any fragment thereof, -a ribozyme against nucleic acids encoding placenta growth factor or the vascular endothelial growth factor receptor-1, and -anti-sense nucleic acids hybridizing with nucleic acids encoding placenta growth factor or vascular endothelial growth factor receptor-1. Active ingredients in such compositions may be present in free form or in the form of a pharmaceutical acceptable salt and optionally at least one pharmaceutically acceptable carrier.

The compounds described herein may be used in a method of inhibiting the growth of non-solid tumor cells that are stimulated by a ligand of vascular endothelial growth factor receptor (including but not limited to VEGFR2 kinase) in mammals, the method comprising treating the mammals with an effective amount of a compound of Formula (I). The compounds described herein may be used in a method of inhibiting the growth of non-solid tumors that are stimulated by a ligand of vascular endothelial growth factor receptor (including but not limited to VEGFR2 kinase) in mammals, the method comprising treating the mammals with an effective amount of a compound of Formula (I) in combination with radiation.

The compounds described herein may also be used in combination with G2/M agents and with therapeutic agents whose therapeutic effectiveness is dependent, at least in part, on the presence of an internalizing cell surface structure on the target cell. Such G2/M agents include but are not limited to vinorelbine tartrate, cisplatin, carboplatin, paclitaxel, doxorubicin, 5FU, docetaxel, vinblastine, vincristine, cyclophosphamide, apigenin, genistein, cycloxazoline.

The compounds described herein may also be used in combination with substances which inhibit signal transduction mediated by human VEGF receptor Flt-1.

The compounds described herein may also be used for treating or preventing a tumor necrosis factor-mediated disease comprising co-administering a tumor necrosis factor alpha antagonist and an effective amount of a compound of Formula (I) to a patient. Contemplated tumor necrosis factor-mediated diseases include but are not limited to autoimmune disease, acute or chronic immune disease, inflammatory disease and neurodegenerative disease.

This invention further relates to a method for inhibiting abnormal cell growth in a mammal which method comprises administering to the mammal an amount of a compound of formula (I), or prodrugs thereof, pharmaceutically active metabolites, pharmaceutically acceptable salts, or pharmaceutically acceptable solvates of said compounds and said prodrugs, in combination with radiation therapy, wherein the amount of the compound, salt, solvate or prodrug is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compounds of formula (I) can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula (I), or prodrugs thereof, pharmaceutically active metabolites, pharmaceutically acceptable salts, or pharmaceutically acceptable solvates of said compounds and said prodrugs, which amount is effective in sensitizing abnormal cells to or enhancing the effects of treatment with radiation. The amount of the compound, salt, solvate or prodrug of formula (I) in this method can be determined according to the means for ascertaining effective amounts of such compounds described herein.

This invention further relates to a method for treating a disease related to vasculogenesis or angiogenesis in a mammal comprising administering to said mammal a therapeutically effective amount of a compound of formula (I), or prodrugs thereof, pharmaceutically active metabolites, pharmaceutically acceptable salts, or pharmaceutically acceptable solvates of said compounds and said prodrugs, in conjunction with a therapeutically effective amount of an anti-hypertensive agent.

Compounds of the present invention may be used in combination with CHK-1 inhibitors. Certain CHK-1 inhibitors have been proposed for cancer therapy (see Sanchez, Y. et.al. (1997) Science 277: 1497–1501 and Flaggs, G. et. al. (1997) Current Biology 7:977–986; U.S. Pat. Nos. 6,413,755, 6,383,744, and 6,211,164; and International Publication Nos. WO 01/16306, WO 01/21771, WO 00/16781, and WO 02/070494). In this embodiment, the CHK-1 inhibitor may be administered as a single agent or as co-therapy with other anti-neoplasm therapies including anti-neoplastic agents and radiation therapy.

The wide variety of available anti-neoplastic agents are contemplated for combination therapy with CHK-1 in accordance with present invention. In a preferred embodiment, anti-neoplastic agents that assert their cytotoxic effects by activating programmed cell death or apoptosis may be used in combination with the CHK-1 inhibitor. The anti-neoplastic agents contemplated in accordance with the present invention include, but are not limited to alkylating agents, including busulfan, chlorambucil, cyclophosphamide, iphosphamide, melphalan, nitrogen mustard, streptozocin, thiotepa, uracil nitrogen mustard, triethylenemelamine, temozolomide, and SARCnu; antibiotics and plant alkaloids including actinomycin-D, bleomycin, cryptophycins, daunorubicin, doxorubicin, idarubicin, irinotecan, L-asparaginase, mitomycin-C, mitramycin, navelbine, paclitaxel, docetaxel, topotecan, vinblastine, vincristine, VM-26, and VP-16-213; hormones and steroids including 5α-reductase inhibitor, aminoglutethimide, anastrozole, bicalutamide, chlorotrianisene, DES, dromostanolone, estramustine, ethinyl estradiol, flutamide, fluoxymesterone, goserelin, hydroxyprogesterone, letrozole, leuprolide, medroxyprogesterone acetate, megestrol acetate, methyl prednisolone, methyltestosterone, mitotane, nilutamide, prednisolone, SERM3, tamoxifen, testolactone, testosterone, triamicnolone, and zoladex; synthetics including all-trans retinoic acid, BCNU (carmustine), CBDCA carboplatin (paraplatin), CCNU (lomustine), cis-diaminedichloroplatinum (cisplatin), dacarbazine, gliadel, hexamethylmelamine, hydroxyurea, levamisole, mitoxantrone, o, p'-DDD (lysodren, mitotane), oxaliplatin, porfimer sodium, procarbazine, GleeVec; antimetabolites including chlorodeoxyadenosine, cytosine arabinoside, 2'-deoxycoformycin, fludarabine phosphate, 5-fluorouracil, 5-FUDR, gemcitabine, camptothecin, 6-mercaptopurine, methotrexate, MTA, and thioguanine; and biologics including alpha interferon, BCG, G-CSF, GM-CSF, interleukin-2, herceptin; and the like.

In a preferred embodiment of the invention, the anti-neoplastic agent is selected from the group consisting of alkylating agents, antibiotics and plant alkaloids, hormones and steroids, synthetic agents having anti-neoplastic activity, antimetabolites and biological molecules having anti-neoplastic activity.

In a preferred embodiment of the invention the antineoplastic agent is selected from the group consisting of Ara-c, VP-16, cis-platin, adriamycin, 2-chloro-2-deoxyadenosine, 9-β-D-arabinosyl-2-fluoroadenine, carboplatin, gemcitabine, camptothecin, paclitaxel, BCNU, 5-fluorouracil, irinotecan, and doxorubicin; more preferably gemcitabine.

The CHK-1 inhibitor in combination with the VEGF inhibitor identified in the present invention may also enhance the antineoplasm effects of radiation therapy. Usually, radiation can be used to treat the site of a solid tumor directly or administered by brachytherapy implants. The various types of therapeutic radiation which are contemplated for combination therapy in accordance with the present invention may be those used in the treatment of cancer which include, but are not limited to X-rays, gamma radiation, high energy electrons and High LET (Linear Energy Transfer) radiation such as protons, neutrons, and alpha particles. The ionizing radiation may be employed by techniques well known to those skilled in the art. For example, X-rays and gamma rays are applied by external and/or interstitial means from linear accelerators or radioactive sources. High-energy electrons may be produced by linear accelerators. High LET radiation is also applied from radioactive sources implanted interstitially.

The compounds of formula (I) or prodrugs thereof, pharmaceutically active metabolites, pharmaceutically acceptable salts, or pharmaceutically acceptable solvates of said compounds and said prodrugs, can each independently also be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

The compounds of the present invention may have asymmetric carbon atoms. Such diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of present invention may in certain instances exist as tautomers. This invention relates to the use of all such tautomers and mixtures thereof.

Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the formulae are intended to cover solvated as well as unsolvated forms of the identified structures. For example, Formula I includes compounds of the indicated structure in both hydrated and non-hydrated forms. Additional examples of solvates include the structures in combination with isopropanol, ethanol, methanol, DMSO, ethyl acetate, acetic acid, or ethanolamine.

In the case of agents that are solids, it is understood by those skilled in the art that the inventive compounds and salts may exist in different crystal or polymorphic forms, all of which are intended to be within the scope of the present invention and specified formulas.

This invention also encompasses pharmaceutical compositions containing and methods of treating bacterial infections through administering prodrugs of compounds of the formula 1. Compounds of formula 1 having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula 1. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

Definitions

As used herein, the following terms have the following meanings, unless expressly indicated otherwise.

The term "comprising" and "including" are used in their open, non-limiting sense.

The terms "abnormal cell growth" and "hyperproliferative disorder" are used interchangeably in this application.

"Abnormal cell growth" refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

The term "acyl" includes alkyl, aryl, or heteroaryl substituents attached to a compound via a carbonyl functionality (e.g., —C(O)-alkyl, —C(O)-aryl, etc.).

The term "acylamino" refers to an acyl radical appended to an amino or alkylamino group, and includes —C(O)—NH$_2$ and —C(O)—NRR" groups where R and R' are as defined in conjunction with alkylamino.

The term "acyloxy" refers to the ester group —OC(O)—R, where R is H, alkyl, alkenyl, alkynyl, or aryl.

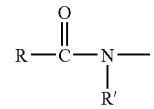

where each of R and R' are independently selected from the group consisting of H, alkyl, and aryl.

The term "alkenyl" includes alkyl moieties having at least one carbon-carbon double bond, including E and Z isomers of said alkenyl moiety. The term also includes cycloalkyl moieties having at least one carbon-carbon double bond, i.e., cycloalkenyl. Examples of alkenyl radicals include ethenyl, propenyl, butenyl, 1,4-butadienyl, cyclopentenyl, cyclohexenyl, prop-2-enyl, but-2-enyl, but-3-enyl, 2-methylprop-2-enyl, hex-2-enyl, and the like. An alkenyl group may be optionally substituted.

The term "alkenylene" refers to a divalent straight chain, branched chain or cyclic saturated aliphatic group containing at least one carbon-carbon double bond, and including E and Z isomers of said alkenylene moiety. An alkyenylene group may be optionally substituted.

The term "alkoxy" means an O-alkyl group. Examples of alkoxy radicals include methoxy, ethoxy, n-propoxy, isopropoxy, n-butoxy, iso-butoxy, sec-butoxy, tert-butoxy and the like.

The term "alkyl" means saturated monovalent hydrocarbon radicals having straight, cyclic or branched moieties. An "alkyl" group may include an optional carbon-carbon double or triple bond where the alkyl group comprises at least two carbon atoms. Cycloalkyl moieties require at least three carbon atoms. Examples of straight or branched alkyl radicals include methyl (Me), ethyl (Et), n-propyl, isopropyl, n-butyl, isobutyl, sec-butyl, tert-butyl, tert-amyl, pentyl, isopentyl, hexyl, heptyl, octyl and the like. An alkyl group may be optionally substituted.

The term "alkylamino" refers to the —NRR' group, where R and R' are independently selected from hydrogen (however, R and R' cannot both be hydrogen), alkyl, and aryl groups; or R and R', taken together, can form a cyclic ring system.

The term "alkylene" refers to a divalent straight chain, branched chain or cyclic saturated aliphatic group. The latter group may also be referred to more specifically as a cycloalkylene group. An alkylene group may be optionally substituted.

The term "alkylthio" alone or in combination, refers to an optionally substituted alkyl thio radical, alkyl-S—.

The term "alkynyl" refers to straight- and branched-chain alkynyl groups having from two to twelve carbon atoms, preferably from 2 to 6 carbons, and more preferably from 2 to 4 carbons. Illustrative alkynyl groups include prop-2-ynyl, but-2-ynyl, but-3-ynyl, 2-methylbut-2-ynyl, hex-2-ynyl, and the like. An alkynyl group may be optionally substituted.

The term "amide" refers to the radical —C(O)N(R')(R") where R' and R" are each independently selected from hydrogen, alkyl, alkenyl, alkynyl, —OH, alkoxy, cycloalkyl, heterocycloalkyl, heteroaryl, aryl as defined above; or R' and R" cyclize together with the nitrogen to form a heterocycloalkyl or heteroaryl.

The term "amino" refers to the —NH$_2$ group.

The term "anti-neoplastic agent" refers to agents capable of inhibiting or preventing the growth of neoplasms, or checking the maturation and proliferation of malignant (cancer) cells.

The term "aromatic" refers to compounds or moieties comprising multiple conjugated double bonds. Examples of aromatic moieties include, without limitation, aryl or heteroaryl ring systems.

The term "aryl" (Ar) means an organic radical derived from a monocyclic or polycyclic aromatic hydrocarbon by removal of one hydrogen, such as phenyl or naphthyl. Preferred aryl groups have from 4 to 20 ring atoms, and more preferably from 6 to 14 ring atoms. An aryl group may be optionally substituted. Illustrative examples of aryl groups include the following moieties:

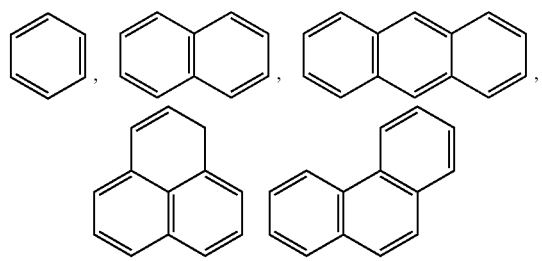

and the like.

The term "aryloxy" means aryl-O—.

The term "arylthio" means an aryl thio radical, aryl-S—.

The term "carbamoyl" or "carbamate" refers to the group —O—C(O)—NRR" where R and R" are independently selected from hydrogen, alkyl, and aryl groups; and R and R" taken together can form a cyclic ring system.

The term "carbocycle" includes optionally substituted cycloalkyl and aryl moieties. The term "carbocycle" also includes cycloalkenyl moieties having at least one carbon-carbon double bond.

The term "carboxy esters" refers to —C(O)OR where R is alkyl or aryl.

The term "cycloalkyl" refers to a monocyclic or polycyclic radical which contains only carbon and hydrogen, and may be saturated, partially unsaturated, or fully unsaturated. A cycloalkyl group may be optionally substituted. Preferred cycloalkyl groups include groups having from three to twelve ring atoms, more preferably from 5 to 10 ring atoms. Illustrative examples of cycloalkyl groups include the following moieties:

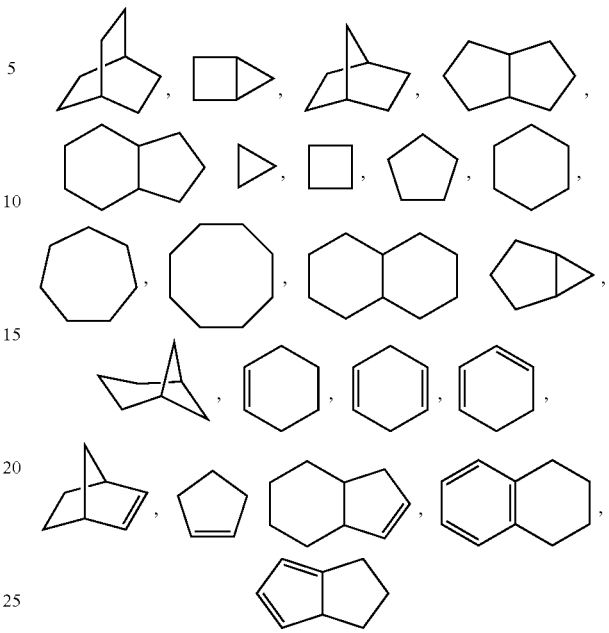

and compounds of the like.

The term "halo" or "halogen" means fluoro, chloro, bromo or iodo. Preferred halo groups are fluoro, chloro and bromo.

The terms haloalkyl, haloalkenyl, haloalkynyl and haloalkoxy include alkyl, alkenyl, alkynyl and alkoxy structures, that are substituted with one or more halo groups or with combinations thereof.

The terms "heteroalkyl" "heteroalkenyl" and "heteroalkynyl" include optionally substituted alkyl, alkenyl and alkynyl radicals and which have one or more skeletal chain atoms selected from an atom other that carbon, e.g., oxygen, nitrogen, sulfur, phosphorus or combinations thereof.

The term "heteroaryl" (heteroAr) refers to an aryl group that includes one or more ring heteroatoms selected from nitrogen, oxygen and sulfur. A heteroaryl group may be optionally substituted. The polycyclic heteroaryl group may be fused or non-fused. Illustrative examples of aryl groups include the following moieties:

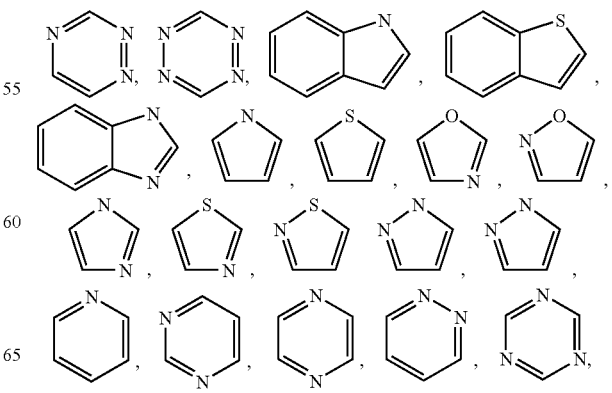

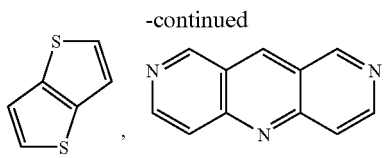

and the like.

The term "heterocycle" refers to aromatic and non-aromatic heterocyclic groups containing one to four heteroatoms each selected from O, S and N, wherein each heterocyclic group has from 4 to 10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzo-fused ring systems. An example of a 4 membered heterocyclic group is azetidinyl (derived from azetidine). An example of a 5 membered heterocyclic group is thiazolyl. An example of a 6 membered heterocyclic group is pyridyl, and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. A heterocycle group may be optionally substituted.

The term "heterocyclic" comprises both heterocycloalkyl and heteroaryl groups.

A "heterocycloalkyl" group refers to a cycloalkyl group that includes at least one heteroatom selected from nitrogen, oxygen and sulfur. The radicals may be fused with an aryl or heteroaryl. Illustrative examples of heterocycloalkyl groups include

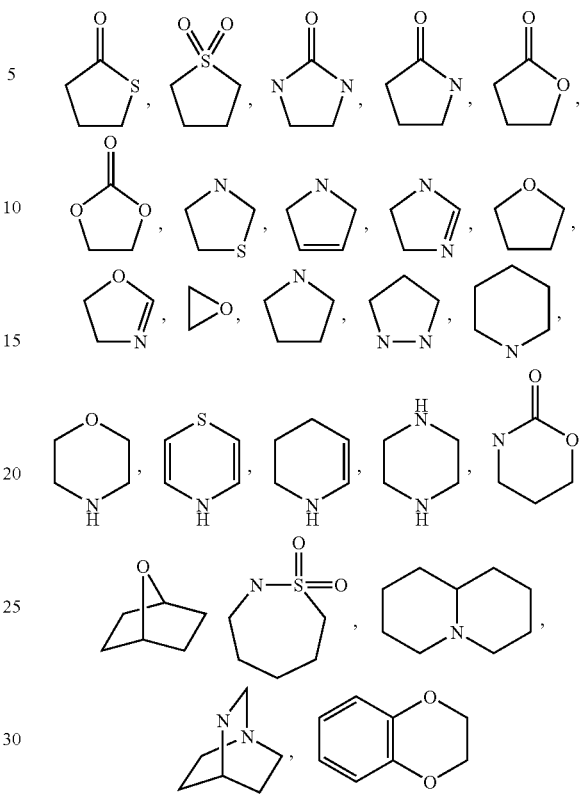

and the like.

The terms "5 membered heterocyclic", "5 or 6 membered heterocyclic", "5 to 8 membered heterocyclic", "5 to 10 membered heterocyclic" or "5 to 13 membered heterocyclic" includes aromatic and non-aromatic heterocyclic groups containing one to four heteroatoms each selected from O, S and N, wherein each heterocyclic group has from 5, 6, 5 to 8, 5 to 10 or 5 to 13 atoms in its ring system, respectively.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "neoplasm" is defined as in Stedman's Medical Dictionary 25$^{th}$ Edition (1990)and refers to an abnormal tissue that grows by cellular proliferation more rapidly than normal and continues to grow after the stimuli that initiated the new growth ceases. Neoplasms show partial or complete lack of structural organization and functional coordination compared with normal tissue, and usually form a distinct mass of tissue that may be either benign (benign tumor) or malignant (cancer).

"Optionally substituted" groups may be substituted or unsubstituted. When substituted, the substituents of an "optionally substituted" group may include, without limitation, one or more substituents independently selected from the following groups or designated subsets thereof: ($C_1$–$C_6$) alkyl, ($C_2$–$C_6$)alkenyl, ($C_2$–$C_6$)alkynyl, ($C_1$–$C_6$)heteroalkyl, ($C_1$–$C_6$)haloalkyl, ($C_2$–$C_6$)haloalkenyl, ($C_2$–$C_6$)haloalkynyl, ($C_3$–$C_6$)cycloalkyl, phenyl, ($C_1$–$C_6$)alkoxy, phenoxy, ($C_1$–$C_6$)haloalkoxy, amino, ($C_1$–$C_6$)alkylamino, ($C_1$–$C_6$)

alkylthio, phenyl-S—, oxo, $(C_1-C_6)$carboxyester, $(C_1-C_6)$ carboxamido, $(C_1-C_6)$acyloxy, H, halogen, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, pyridinyl, thiophene, furanyl, $(C_1-C_6)$carbamate, and $(C_1-C_6)$urea. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstituted (e.g., —$CH_2CF_3$).

The term "oxo" means an "O" group.

The term "perhalo" refers to groups wherein every C—H bond has been replaced with a C-halo bond on an aliphatic or aryl group. Examples of perhaloalkyl groups include —$CF_3$ and —$CFCl_2$.

The term "substituted" means that the group in question, e.g., alkyl group, etc., may bear one or more substituents.

The term "ureyl" or "urea" refers to the group —N(R)—C(O)—NR'R" where R, R', and R" are independently selected from hydrogen, alkyl, aryl; and where each of R—R', R'R", or R—R" taken together can form a cyclic ring system.

Pharmaceutical Formulations and Compositions

In addition to compounds of Formula I, the invention includes N-oxides, pharmaceutically acceptable prodrugs, pharmaceutically acceptable solvates, pharmaceutically active metabolites, and pharmaceutically acceptable salts of such compounds, prodrugs, solvates and metabolites.

The term "pharmaceutically acceptable" means pharmacologically acceptable and substantially non-toxic to the subject being administered the agent.

A "pharmacological composition" refers to a mixture of one or more of the compounds described herein, or physiologically acceptable salts thereof, with other chemical components, such as physiologically acceptable carriers and/or excipients. The purpose of a pharmacological composition is to facilitate administration of a compound to an organism.

A "physiologically acceptable carrier" refers to a carrier or diluent that does not cause significant or otherwise unacceptable irritation to an organism and does not unacceptably abrogate the biological activity and properties of the administered compound.

An "excipient" generally refers to substance, often an inert substance, added to a pharmacological composition or otherwise used as a vehicle to further facilitate administration of a compound. Examples of excipients include but are not limited to calcium carbonate, calcium phosphate, various sugars and types of starch, cellulose derivatives, gelatin, vegetable oils and polyethylene glycols.

The term "prodrug" means compounds that are drug precursors, which following administration, release the drug in vivo via some chemical or physiological process (e.g., a prodrug on being brought to the physiological pH is converted to the desired drug form).

Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula (I). The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

"A pharmaceutically acceptable prodrug" is a compound that may be converted under physiological conditions or by solvolysis to the specified compound or to a pharmaceutically acceptable salt of such compound. "A pharmaceutically active metabolite" is intended to mean a pharmacologically active product produced through metabolism in the body of a specified compound or salt thereof. Prodrugs and active metabolites of a compound may be identified using routine techniques known in the art. See, e.g., Bertolini et al., *J. Med. Chem.*, 40, 2011–2016 (1997); Shan et al., *J. Pharm. Sci.*, 86 (7), 765–767; Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); and Larsen, *Design and Application of Prodrugs, Drug Design and Development* (Krogsgaard-Larsen et al., eds., Harwood Academic Publishers, 1991).

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, phosphoric acid and the like, or with an organic acid, such as acetic acid, phenylacetic acid, propionic acid, stearic acid, lactic acid, ascorbic acid, maleic acid, hydroxymaleic acid, isethionic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid, 2-acetoxybenzoic acid or cinnamic acid, a sulfonic acid, such as p-toluenesulfonic acid, methanesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine and piperazine, and inorganic salts derived from sodium, calcium, potassium, magnesium, manganese, iron, copper, zinc, aluminum and lithium.

Pharmaceutical compositions according to the invention may, alternatively or in addition to a compound of Formula (I), comprise as an active ingredient pharmaceutically acceptable prodrugs, pharmaceutically active metabolites, and pharmaceutically acceptable salts of such compounds and metabolites. Such compounds, prodrugs, multimers, salts, and metabolites are sometimes referred to herein collectively as "active agents" or "agents."

It will be appreciated that any solvate (e.g. hydrate) form of compounds of formula (I) and prodrugs thereof can be used for the purpose of the present invention.

Therapeutically effective amounts of the active agents of the invention may be used to treat diseases mediated by modulation or regulation of protein kinases. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The compositions containing the compound(s) of the described herein can be administered for prophylactic and/or therapeutic treatments. In therapeutic applications, the compositions are administered to a patient already suffering from a proliferative disorder or condition (including, but not limited to, cancer), as described above, in an amount sufficient to cure or at least partially arrest the symptoms of the proliferative disorder or condition. An amount adequate to accomplish this is defined as "therapeutically effective amount or dose."Amounts effective for this use will depend on the severity and course of the proliferative disorder or condition, previous therapy, the patient's health status and response to the drugs, and the judgment of the treating physician. In prophylactic applications, compositions containing the compounds described herein are administered to a patient susceptible to or otherwise at risk of a particular proliferative disorder or condition. Such an amount is defined to be a "prophylactically effective amount or dose." In this use, the precise amounts also depend on the patient's state of health, weight, and the like. It is considered well within the skill of the art for one to determine such therapeutically effective or prophylactically effective amounts by routine experimentation (e.g., a dose escalation clinical trial).

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system (e.g., a tumor cell). An "enhancing-effective amount," as used herein, refers to an amount adequate to enhance the effect of another therapeutic agent in a desired system (including, by way of example only, a tumor cell in a patient). When used in a patient, amounts effective for this use will depend on the severity and course of the proliferative disorder (including, but not limited to, cancer), previous therapy, the patient's health status and response to the drugs, and the judgment of the treating physician. It is considered well within the skill of the art for one to determine such enhancing-effective amounts by routine experimentation.

Once improvement of the patient's conditions has occurred, a maintenance dose is administered if necessary. Subsequently, the dosage or the frequency of administration, or both, can be reduced, as a function of the symptoms, to a level at which the improved proliferative disorder or condition is retained. When the symptoms have been alleviated to the desired level, treatment can cease. Patients can, however, require intermittent treatment on a long-term basis upon any recurrence of the disease symptoms.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of one or more kinases, for example protein kinases such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

Agents that potently regulate, modulate, or inhibit cell proliferation are preferred. For certain mechanisms, inhibition of the protein kinase activity associated with CDK complexes, among others, and those which inhibit angiogenesis and/or inflammation are preferred. The present invention is further directed to methods of modulating or inhibiting protein kinase activity, for example in mammalian tissue, by administering a compound of Formula (I). The activity of agents as anti-proliferatives is easily measured by known methods, for example by using whole cell cultures in an MTT assay. The activity of the compounds of Formula (I) as modulators of protein kinase activity, such as the activity of kinases, may be measured by any of the methods available to those skilled in the art, including in vivo and/or in vitro assays. Examples of suitable assays for activity measurements include those described in International Publication No. WO 99/21845; Parast et al., *Biochemistry*, 37, 16788–16801 (1998); Connell-Crowley and Harpes, *Cell Cycle: Materials and Methods*, (Michele Pagano, ed.

Springer, Berlin, Germany)(1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I and an inert, pharmaceutically acceptable carrier or diluent. In one embodiment of the pharmaceutical compositions, efficacious levels of the compounds of Formula (I) are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

A compound of Formula (I) can be administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of a compound of Formula (I) can be dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, with courses of treatment repeated at appropriate intervals. Administration of prodrugs is typically dosed at weight levels that are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations that can be used pharmaceutically.

Proper formulation is dependent upon the route of administration chosen. For injection, the agents of the invention may be formulated into aqueous solutions, preferably in physiologically compatible buffers such as Hanks's solution, Ringers solution, or physiological saline buffer. For transmucosal administration, penetrants appropriate to the barrier to be permeated are used in the formulation. Such penetrants are generally known in the art.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of agents.

Pharmaceutical preparations that can be used orally include push-fit capsules made of gelatin, as well as soft, sealed capsules made of gelatin and a plasticizer, such as glycerol or sorbitol. The push-fit capsules can contain the agents in admixture with fillers such as lactose, binders such as starches, and/or lubricants such as talc or magnesium stearate, and, optionally, stabilizers. In soft capsules, the agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions take the form of tablets or lozenges formulated in conventional manners.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the agents in water-soluble form. Additionally, suspensions of the agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

For administration to the eye, the agent is delivered in a pharmaceutically acceptable ophthalmic vehicle such that the compound is maintained in contact with the ocular surface for a sufficient time period to allow the compound to penetrate the corneal and internal regions of the eye, for example, the anterior chamber, posterior chamber, vitreous body, aqueous humor, vitreous humor, cornea, iris/ciliary, lens, choroid/retina and sclera. The pharmaceutically acceptable ophthalmic vehicle may be an ointment, vegetable oil, or an encapsulating material. A compound of the invention may also be injected directly into the vitreous and aqueous humor.

Alternatively, the agents may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the agents may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semi-permeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The agents of the invention may be useful in combination with known anti-cancer treatments such as: DNA interactive agents such as cisplatin or doxorubicin; topoisomerase II inhibitors such as etoposide; topoisomerase I inhibitors such as CPT-11 or topotecan; tubulin interacting agents such as paclitaxel, docetaxel or the epothilones; hormonal agents such as tamoxifen; thymidilate synthase inhibitors such as 5-fluorouracil; and anti-metalbolites such as methotrexate. They may be administered together or sequentially, and when administered sequentially, the agents may be administered either prior to or after administration of the known anticancer or cytotoxic agent.

The term "chemotherapeutic agent" as used herein includes, for example, hormonal agents, antimetabolites, DNA interactive agents, tubulin-interactive agents, and others such as aspariginase or hydroxyureas.

DNA-interactive agents include alkylating agents, such as cisplatin, cyclophosphamide, altretamine; DNA strand-breakage agents, such as bleomycin; intercalating topoisomerase II inhibitors, e.g., dactinomycin and doxorubicin); nonintercalating topoisomerase II inhibitors such as, etoposide and teniposide; and the DNA minor groove binder plicamydin, for example.

Alkylating agents may form covalent chemical adducts with cellular DNA, RNA, or protein molecules, or with smaller amino acids, glutathione, or similar chemicals. Examples of typical alkylating agents include, but are not limited to, nitrogen mustards, such as chlorambucil, cyclophosphamide, isofamide, mechlorethamine, melphalan, uracil mustard; aziridine such as thiotepa; methanesulfonate esters such as busulfan; nitroso ureas, such as carmustine, lomustine, streptozocin; platinum complexes, such as cisplatin, carboplatin; bioreductive alkylator, such as mitomycin, and procarbazine, dacarbazine and altretamine. DNA strand-breaking agents include bleomycin, for example.

DNA topoisomerase II inhibitors may include intercalators such as the following: amsacrine, dactinomycin, daunorubicin, doxorubicin (adriamycin), idarubicin, and mitoxantrone; as well as nonintercalators such as etoposide and teniposide.

An example of a DNA minor groove binder is plicamycin.

Antimetabolites generally interfere with the production of nucleic acids and thereby growth of cells by one of two major mechanisms. Certain drugs inhibit production of deoxyribonucleoside triphosphates that are the precursors for DNA synthesis, thus inhibiting DNA replication. Examples of these compounds are analogues of purines or pyrimidines and are incorporated in anabolic nucleotide pathways. These analogues are then substituted into DNA or RNA instead of their normal counterparts.

Antimetabolites useful as chemotherapeutic agents include, but are not limited to: folate antagonists such as methotrexate and trimetrexate; pyrimidine antagonists, such as fluorouracil, fluorodeoxyuridine, CB3717, azacitidine, cytarabine, and floxuridine; purine antagonists such as mercaptopurine, 6-thioguanine, fludarabine, pentostatin; and ribonucleotide reductase inhibitors such as hydroxyurea.

Tubulin interactive agents act by binding to specific sites on tubulin, a protein that polymerizes to form cellular microtubules. Microtubules are critical cell structure units and are required for cell division. These therapeutic agents disrupt the formation of microtubules. Exemplary tubulin-interactive agents include vincristine and vinblastine, both alkaloids and paclitaxel (Taxol).

Hormonal agents are also useful in the treatment of cancers and tumors, but only rarely in the case of B cell malignancies. They are used in hormonally susceptible tumors and are usually derived from natural sources. Hormonal agents include, but are not limited to, estrogens, conjugated estrogens and ethinyl estradiol and diethylstilbesterol, chlortrianisen and idenestrol; progestins such as hydroxyprogesterone caproate, medroxyprogesterone, and megestrol; and androgens such as testosterone, testosterone propionate; fluoxymesterone, and methyltestosterone.

Adrenal corticosteroids are derived from natural adrenal cortisol or hydrocortisone and are used to treat B cell malignancies. They are used because of their anti-inflammatory benefits as well as the ability of some to inhibit mitotic divisions and to halt DNA synthesis. These compounds include, but are not limited to, prednisone, dexamethasone, methylprednisolone, and prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include, for example, antiestrogenic agents such as tamoxifen, antiandrogen agents such as flutamide; and antiadrenal agents such as mitotane and aminoglutethimide.

Other agents include hydroxyurea (which appears to act primarily through inhibition of the enzyme ribonucleotide reductase), and asparaginase (an enzyme which converts asparagine to aspartic acid and thus inhibits protein synthesis).

Included within the scope of cancer therapy agents are radiolabeled antibodies, including but not limited to, Zevalin™ (IDEC Pharmaceuticals Corp.) and Bexxar™ (Corixa, Inc.); the use of any other radioisotope (e.g., $^{90}$Y and $^{131}$I) coupled to an antibody or antibody fragment that recognizes an antigen expressed by a neoplasm; external beam radiation or any other method for administration of radiation to a patient.

Further included within the scope of cancer therapy agents are cytotoxins, including but not limited to an antibody or antibody fragment linked to a cytotoxin, or any other method for selectivly delivering a cytotoxic agent to a tumor cell.

Further included within the scope of cancer therapy agents are selective methods for destroying DNA, or any method for delivering heat to a tumor cells, including by way of example only, nanoparticles.

Further included within the scope of cancer therapy agents is the use of unlabeled antibodies or antibody fragments capable of killing or depleting tumor cells, including by way of example only, Rituxan™ (IDEC Pharmaceuticals Corp.) and Herceptin™ (Genentech).

The agents may be prepared using the reaction routes and synthesis schemes as described below, employing the general techniques known in the art using starting materials that are readily available. The preparation of preferred compounds of the present invention is described in detail in the following examples, but the artisan will recognize that the chemical reactions described may be readily adapted to prepare a number of other anti-proliferatives or protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

DETAILED DESCRIPTION

The compounds of Formula (I) can act as antagonists of the VEGFR2. Without being bound to any particular theory, the linked rings are thought to provide favorable space-filling and electrostatic complementarity in the active site of the targeted protein.

In the examples described below, unless otherwise indicated, all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF), N,N-dimethylformamide (DMF), dichloromethane, toluene, and dioxane were purchased from Aldrich in Sure seal bottles and used as received. All solvents were purified using standard methods readily known to those skilled in the art, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates Analtech (0.25 mm) and eluted with the appropriate solvent ratios (v/v), and are denoted where appropriate. The reactions were assayed by TLC and terminated as judged by the consumption of starting material.

Visualization of the TLC plates was done with a p-anisaldehyde spray reagent or phosphomolybdic acid reagent (Aldrich Chemical 20 wt % in ethanol) and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Baker grade flash silica gel (47–61 μm) and a silica gel: crude material ratio of about 20:1 to 50:1 unless otherwise stated. Hydrogenolysis was done at the pressure indicated in the examples or at ambient pressure.

$^1$H-NMR spectra were recorded on a Bruker instrument operating at 300 MHz and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers (cm$^{-1}$). The mass spectra were obtained using LSIMS or electrospray. All melting points (mp) are uncorrected.

General Synthetic Schemes Used for the Preparation of Thenopyridine Compounds

Preparative Methods

The following methods describe typical synthetic procedures using specific materials. Many embodiments of the present invention may be synthesized using the described methods. The skilled artisan will recognize that different acids, acid chlorides, amines, phenols, chloropyridine derivatives, and methyl ethers may be substituted in the following descriptions to suit the preparation of a desired embodiment. The following methods may be scaled upwards or downwards to suit the amount of desired material.

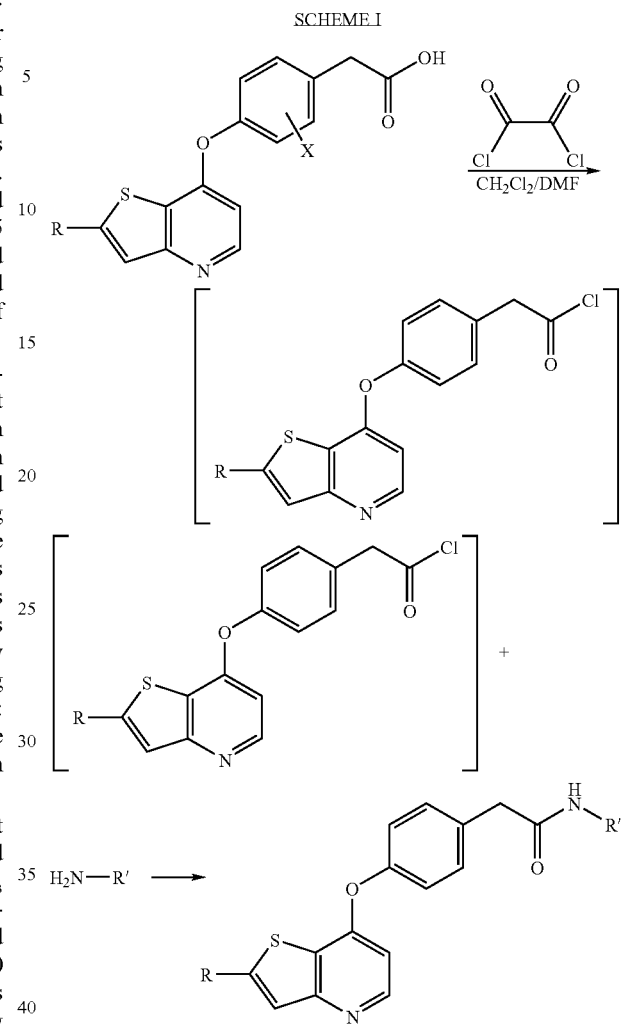

(A) Method A

Method A follows the general procedure provided in Scheme I. Scheme I is a general method for amide bond formation beginning with carboxylic acids and amines. The skilled artisan will recognize that many methods exist for the coupling of amines and carboxylates and the method described herein is given by way of example.

(B) Example of Method A

To a suspension or solution of acid, for example {3-fluoro-4-[2-(1-methyl-1H-imidazol-2-yl)-thieno[3,2-b]pyridin-7-yloxy]-phenyl}-acetic acid (126 mg, 0.329 mmol) in $CH_2Cl_2$ (5 mL) was added 2 M oxalyl chloride in $CH_2Cl_2$ (0.49 mL, 0.987 mmol, 3 eq), followed by 3 drops of DMF. The mixture was stirred at ambient temperature for one hour, concentrated and dried under vacuum. The crude phenylacetylchloride was re-dissolved in $CH_2Cl_2$ (5 mL), and the corresponding amine, for example 2-amino-4,6-dimethylpyridine (60 mg, 0.492 mmol, 1.5 eq) was added, followed by DMAP (catalytic amount) and triethylamine (1–1.5 eq). The mixture was stirred at ambient temperature overnight, concentrated and purified by reversed phase HPLC eluted with 30%–70% acetonitrile in water, or by normal phase silica gel column eluting with 1%–10% MeOH in $CHCl_3$ or gradient of EtOAc in hexanes (depending on the polarity of the product) to give the desired amide in 20–90% yield.

SCHEME II

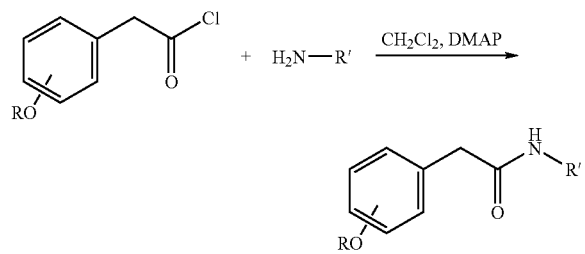

(A) Method B

Method B follows the general procedure provided in Scheme II. Method B is similar to Method A, but demonstrates that amide bond formation may precede formation of thienopyridine-aryl (phenyl) ether bond formation.

(B) Example of Method B

To a solution of acid chloride, for example 4-methoxyphenylacetyl chloride (1.00 g, 5.42 mmol) in $CH_2Cl_2$ (30 mL) was added amine, such as 2-amino-4,6-dimethylpyridine (661 mg, 5.42 mmol), followed by DMAP (catalytic amount) and triethylamine (1 eq). After stirring at ambient temperature overnight, the mixture was concentrated and purified by flash column chromatography and eluted with gradient of EtOAc in hexanes to provide the desired amide in 50–90% yield.

SCHEME III

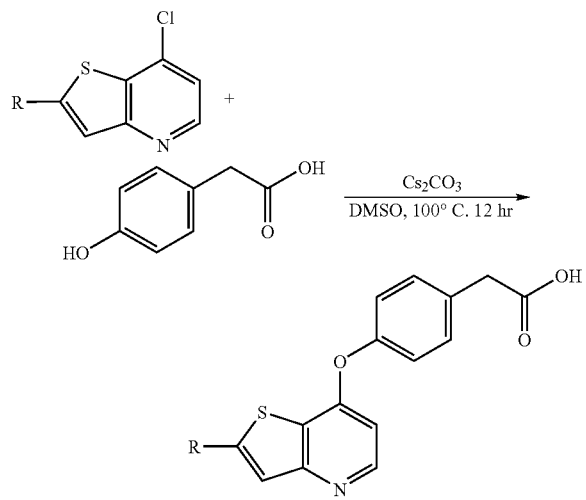

(A) Method C

Method C follows the general procedure provided in Scheme III. Method C is a general method for coupling thienopyridine moieties to phenyl acetic moieties via an ether linkage. In this method, chloride is displace by phenolate to yield an aryl phenyl ether.

(B) Example of Method C

To a solution of chloropyridine derivative, for example 7-chloro-2-(1-methyl-1H-imidazol-2-yl)-thieno[3,2-b]pyridine (300 mg, 1.20 mmol), and phenol, for example 3-fluoro-4-hydroxyphenylactic acid (245 mg, 1.44 mmol, 1.2 eq), in 3 ml DMSO was added $Cs_2CO_3$ (984 mg, 3.00 mmol, 2.5 eq). The mixture was heated at 100° C. for 12 hours and cooled to room temperature. EtOAc and water were added, and the mixture was neutralized by 1N HCl. Precipitate was formed, filtered, and washed by water. The solid was dried in a vacuum-oven at 60° C. and used as is for the next step or was further purified by column chromatography eluting with 1–10% MeOH in $CHCl_3$. The desired phenyl ethers were obtained in 40–80% yield.

SCHEME IV

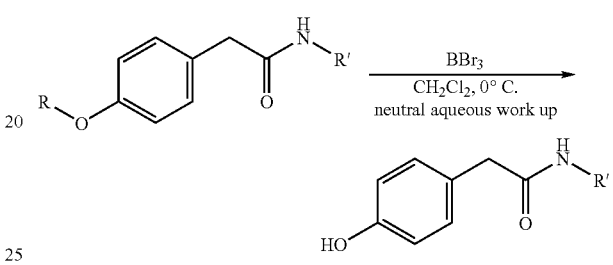

(A) Method D

Method D follows the general procedure provided in Scheme IV. Method D is a general method for dealkylating alkyl phenyl ethers to form phenols.

(B) Example of Method D

To a 0° C. solution of methyl ether, such as N-(4,6-dimethyl-pyridin-2-yl)-2-(4-methoxy-phenyl)-acetamide (720 mg, 2.67 mmol), in 15 mL of $CH_2Cl_2$ was added 1.0 M $BBr_3$ (8.00 mL, 8.00 mmol, 3–4 eq). The mixture was stirred at room temperature overnight. The reaction was quenched with MeOH, neutralized with concentrated aqueous $NH_4OH$ to pH ~7. The resulting mixture was stirred at room temperature for one hour and poured into water, extracted with $CH_2Cl_2$ for three times, dried over $Na_2SO_4$, concentrated in vacuo, and further purified by column chromatography to give the desired phenol or alcohol in 70–100% yield.

EXAMPLES

Example 1

N-(4,6-Dimethyl-pyridin-2-yl)-2-{3-fluoro-4-[2-(1-methyl-1H-imidazol-2-yl)-thieno[3,2-b]pyridin-7-yloxy]-phenyl}-acetamide

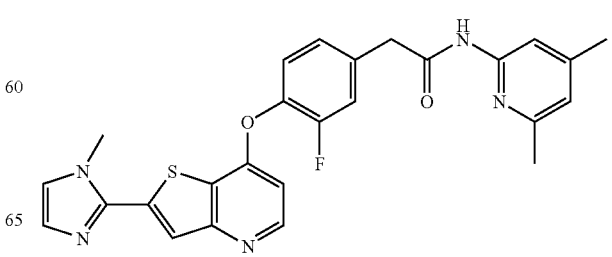

Intermediate 1a: {3-Fluoro-4-[2-(1-methyl-1H-imidazol-2-yl)-thieno[3,2-b]pyridin-7-yloxy]-phenyl}-acetic acid

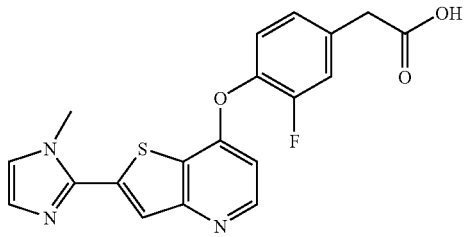

was prepared from 7-chloro-2-(1-methyl-1H-imidazol-2-yl)-thieno[3,2-b]pyridine and 3-fluoro-4-hydroxyphenyllactic acid following Method C. The synthesis of 7-chloro-2-(1-methyl-1H-imidazol-2-yl)-thieno[3,2-b]pyridine has been described in PCT application WO99/24440, Example 150. $^1$H NMR (300 MHz, DMSO-$d_6$) δ 8.54 (d, 1H, J=4.90 Hz), 7.91 (s, 1H), 7.49–7.42 (m, 3H), 7.26 (d, 1H, J=9.42 Hz), 7.05(s, 1H), 6.65 (d, 1H, J=5.27 Hz), 4.00 (s, 2H), 3.17 (s, 3H). LCMS (ESI+) [M+H]/z Calc'd 384, found 384.

The compound of Example 1 was prepared from intermediate 1a and 2-amino-4,6-dimethylpyridine following Method A. $^1$H NMR (300 MHz, CD$_3$OD) δ 8.41 (d, 1H, J=5.65 Hz), 7.73 (s, 1H), 7.65 (s, 1H), 7.35–7.24 (m, 4H), 7.03 (s, 1H), 6.77 (s, 1H), 6.62 (d, 2H, J=4.52 Hz), 3.95 (s, 3H), 3.74 (s, 2H), 2.32 (s, 3H), 2.23 (s, 3H). LCMS (ESI+) [M+H]/z Calc'd 488, found 488. Anal. (C$_{26}$H$_{22}$N$_5$O$_2$SF. 1.0H$_2$O.1.2CH$_3$COOH)C, H, N.

Example 2

2-{3-Fluoro-4-[2-((R)-3-hydroxy-pyrrolidine-1-carbonyl)-thieno[3,2-b]pyridin-7-yloxy]-phenyl}-N-methyl-acetamide

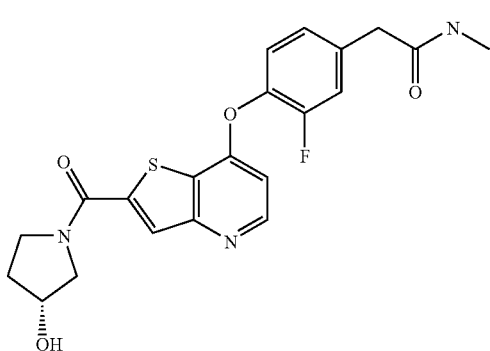

Intermediate 2a:
2-(3-Fluoro-4-hydroxy-phenyl)-N-methyl-acetamide

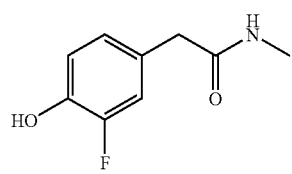

was prepared from 3-fluoro-4-hydroxyphenyllactic acid and methyl amine following Method A. S$^1$H NMR (300 MHz, CD$_3$OD) δ 7.89 (s, 1H), 6.90 (d, 1H, J=13.37 Hz), 6.82–6.71 (m, 1H), 3.29 (s, 2H), 2.62 (s, 3H). LCMS (ESI+) [M+H]/z Calc'd 184, found 184.

Intermediate 2b: (7-Chloro-thieno[3,2-b]pyridin-2-yl)-(3-hydroxy-pyrrolidin-1-yl)-methanone

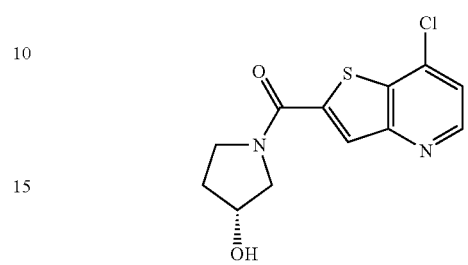

was prepared from 7-chloro-thieno[3,2-b]pyridine-2-carboxylic acid lithium salt (prepared according to PCT application WO01/94353, Example 1) and 3R-hydroxy-pyrrolidine following Method A. $^1$H NMR (DMSO-$d_6$): δ 8.73 (1H, d, J=5.1 Hz), 8.15, 8.09 (1H, s), 7.69 (1H, d, J=5.1 Hz), 5.10–5.06 (1H, m), 4.43–4.29 (1H, m), 4.05–3.89 (2H, m), 3.72–3.43 (2H, m), 2.08–1.79 (2H, m).

The compound of Example 2 was prepared from the coupling of intermediates 2a and 2b following Method C. $^1$H NMR (300 MHz, CD$_3$OD) δ 8.43 (d, 1H, J=5.46 Hz), 7.85 (d, 1H, J=17.33 Hz), 7.28–7.12 (m, 3H), 6.62 (d, 1H, J=5.46 Hz), 4.41(bs, 1H), 3.95–3.89 (m, 2H), 3.73–3.60 (m, 3H), 3.47 (s, 2H), 2.65 (s, 3H), 2.13–1.94 (m, 2H). LCMS (ESI+) [M+H]/z Calc'd 430, found 430. Anal. (C$_{21}$H$_{20}$N$_3$O$_4$SF. 0.4CH$_2$Cl$_2$) C, H, N.

Example 3

2-{4-[2-((3R, 4R)-3,4-Dihydroxy-pyrrolidine-1-carbonyl)-thieno 3,2-b]pyridin-7-yloxy]-phenyl}-N-(4,6-dimethyl-pyridin-2-yl)-acetamide

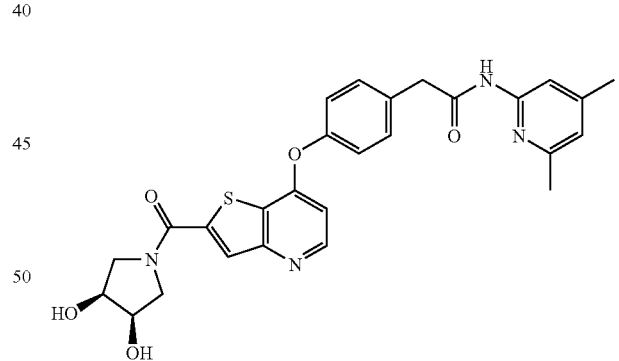

Intermediate 3a: N-(4,6-Dimethyl-pyridin-2-yl)-2-(4-methoxy-phenyl)-acetamide

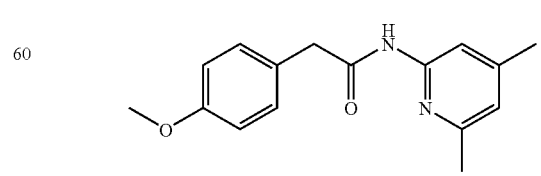

was prepared from 4-methoxyphenylacetyl chloride and 2-amino-4,6-dimethylpyridine following Method B. $^1$H NMR (300 MHz, CDCl₃) δ 7.86 (s, 1H), 7.73 (s, 1H), 7.24 (d, 2H, J=8.34 Hz), 6.91 (d, 2H, J=8.59 Hz), 6.70(s, 1H), 3.81 (s, 3H), 3.66 (s, 2H), 2.35 (s, 3H), 2.29 (s, 3H). LCMS (ESI+) [M+H]/z Calc'd 271, found 271.

Intermediate 3b: N-(4,6-Dimethyl-pyridin-2-yl)-2-(4-hydroxy-phenyl)-acetamide

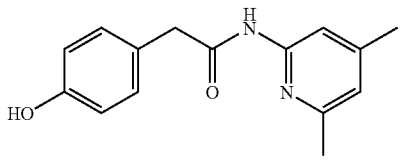

was prepared from intermediate 3a following Method D. ¹H NMR (300 MHz, CDCl₃) δ 7.99 (s, 1H), 7.95 (s, 1H), 7.06 (d, 2H, J=8.34 Hz), 6.74 (s, 1H), 6.63 (d, 2H, J=8.59 Hz), 3.66 (s, 2H), 2.34 (s, 3H), 2.33 (s, 3H). LCMS (ESI+) [M+H]/z Calc'd 257, found 257.

Intermediate 3c: 3,4-cis-Dihydroxy-pyrrolidine-1-carboxylic acid benzyl ester

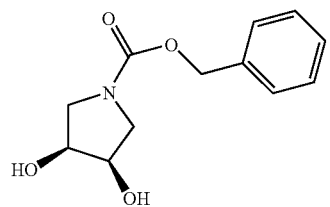

To a solution of benzyl 3-pyrroline-1-carboxylate (15 g, 90%, 66.4 mmol) in THF (100 mL) and water (25 mL), was added osmium tetroxide (10 mL, 2.5 wt. % solution in 2-methyl-2-propanol, 0.8 mmol) and 4-methylmorpholine N-oxide (8.56 g, 73 mmol) as solid. The mixture was stirred at room temperature overnight and concentrated, in vacuo. The residue was re-dissolved in EtOAc (300 mL) and washed with aqueous Na₂SO₃ (1.5 g in 100 mL water) solution, aqueous NaHCO₃ solution and brine. The combined aqueous layer was extracted once with EtOAc (100 mL). The combined organic extracts were dried over Na₂SO₄ and concentrated, in vacuo. The crude product was further purified by flash column chromatography eluting with 4–5% MeOH in CH₂Cl₂ to give 15.26 g (97%) of a white solid. ¹H NMR (300 MHz, CDCl₃) δ 7.34 (5H, m), 5.11 (2H, bs), 4.26 (2H, m), 3.66 (2H, m), 3.41 (2H, m), 1.56 (2H, bs).

Intermediate 3d: 3,4-cis-Dimethoxy-pyrrolidine-1-carboxylic acid benzyl ester

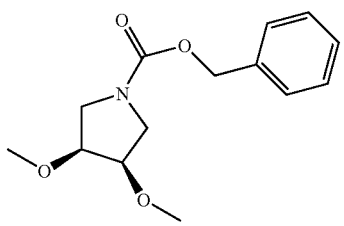

To a stirred solution of 3,4-cis-dihydroxy-pyrrolidine-1-carboxylic acid benzyl ester 3c (15.2 g, 64.3 mmol) in anhydrous THF (130 mL) was added iodomethane (36 g, 257 mmol) at 0° C.; sodium hydride (6.4 g, 60% in mineral oil, 160 mmol) was then added slowly as at 0° C. The mixture was allowed to warm to room temperature and stirred at room temperature for 3 hours. Aqueous 1N HCl (30 mL) was then added to the mixture which was concentrated, in vacuo, to remove THF. The residue was re-dissolved in EtOAc (300 mL) and washed with water and brine. The organic layer was dried over Na₂SO₄, filtered, and concentrated, in vacuo. The crude was further purified by flash column chromatography eluting with 5–25% EtOAc in CH₂Cl₂, to give 17 g (99%) of intermediate 3d as a yellow oil. ¹H NMR (300 MHz, CDCl₃) δ 7.35 (5H, m), 5.12 (2H, m), 3.87 (2H, m), 3.55 (2H, m), 3.42 (6H, bs), 1.58 (2H, s).

Intermediate 3e: 3,4-cis-Dimethoxy-pyrrolidine

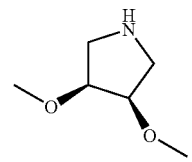

To a stirred solution of 3,4-cis-dimethoxy-pyrrolidine-1-carboxylic acid benzyl ester 3d (16.95 g, 63.9 mmol) in MeOH (150 mL), was added 10% Pd on C (1.3 g). The mixture was stirred under an H₂ balloon at room temperature for 3 hours and filtered through celite. The filtrate was concentrated, in vacuo, re-dissolved in CH₂Cl₂ and dried over Na₂SO₄. The solution was concentrated to give 8.3 g (99%) of intermediate 3e as a yellow oil. ¹H NMR (300 MHz, CDCl₃) δ 3.80 (2H, m), 3.47 (2H, bs), 3.41 (6H, s), 3.01 (2H, bs).

Intermediate 3f: 7-Chloro-2-[meso-3,4-dimethoxy-pyrrolidine-1-carbonyl]thieno[3,2-b]pyridine

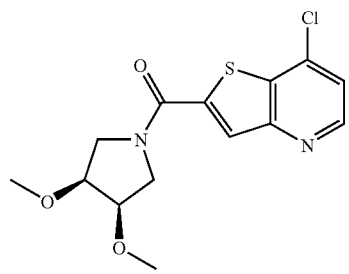

was prepared by the coupling of lithium 7-chlorothieno[3,2-b]pyridine-2-carboxylate and 3,4-cis-dimethoxypyrrolidine 3e in a manner as previously described in Method A to give intermediate 3f as a pale yellow syrup. ¹H NMR (CD₃OD): δ 8.70 (1H, d, J=5.1 Hz), 8.03 (1H, s), 7.61 (1H, d, J=5.1 Hz), 4.20–4.07 (2H, m), 3.97–3.75 (2H, m), 3.52 (3H, s), 3.48 (3H, s), 3.35–3.29 (2H, m).

Intermediate 3g: 7-Chloro-2-[meso-3,4-dimethoxy-pyrrolidine-1-carbonyl]thieno[3,2-b]pyridine

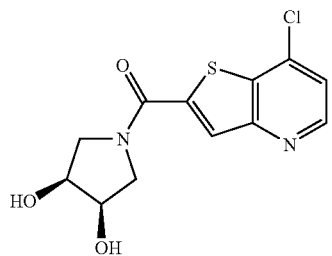

was prepared from 7-chloro-2-[meso-3,4-dimethoxypyrrolidine-1-carbonyl]thieno[3,2-b]pyridine (3f) and BBr$_3$ in a manner described in Method D and gave the intermediate 3g as a pale white solid.

The compound of Example 3 was prepared from (7-chloro-thieno[3,2-b]pyridin-2-yl)-(3,4-dihydroxy-pyrrolidin-1-yl)-methanone (3g) and N-(4,6-dimethyl-pyridin-2-yl)-2-(4-hydroxy-phenyl)-acetamide (3b) following Method C. $^1$H NMR (300 MHz, CD$_3$OD) δ 8.43 (d, 1H, J=5.47 Hz), 7.81 (d, 1H, J=6.60 Hz), 7.64 (s, 1H), 7.42 (d, 2H, J=8.67 Hz), 7.14 (d, 2H, J=8.47 Hz), 6.75 (s, 1H), 6.66 (d, 1H, J=5.46 Hz), 4.19 (s, 2H), 4.03–3.98 (m, 1H), 3.74–3.68 (m, 4H), 3.57–3.52 (m, 1H), 2.30 (s, 3H), 2.21 (s, 3H). LCMS (ESI+) [M+H]/z Calc'd 519, found 519. Anal. (C$_{27}$H$_{26}$N$_4$O$_5$S.0.6EtOAc.0.2CHCl$_3$) C, H, N.

Example 4

2-{4-[2-((R)-3-Dimethylamino-pyrrolidine-1-carbonyl)-thieno[3,2-b]pyridin-7-yloxy]-phenyl}-N-(4,6-dimethyl-pyridin-2-yl)-acetamide

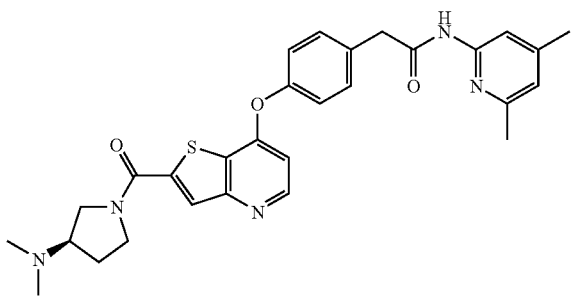

Intermediate 4a: (7-Chloro-thieno[3,2-b]pyridin-2-yl)-(3R-dimethylamino-pyrrolidin-1-yl)-Methanone

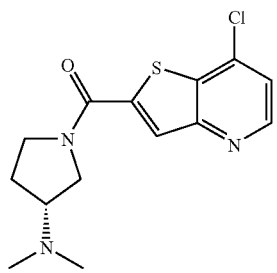

was prepared by the reaction of 7-chlorothieno[3,2-b]pyridine-2-carboxylic acid (0.214 g, 1.0 mmol) with (3R)-N,N-dimethylpyrrolidin-3-amine (0.114 g, 1.0 mmol) and Et$_3$N (0.139 mL, 1.0 mmol) in the manner of Method A and gave intermediate 4a as a brown solid (0.1349, 43%). $^1$H NMR (300 MHz, CD$_3$OD) δ 7.24 (d, 1H, J=5.09 Hz), 6.57 (d, 1H, J=8.48 Hz), 6.15 (d, 1H, J=5.09 Hz), 2.70 (m, 1H), 2.51 (m, 2H), 2.24 (m, 1H), 2.04 (m, 1H), 1.49 (m, 1H), 0.93 (s, 3H), 0.90 (s, 3H), 0.52 (m, 1H); ESIMS (MH$^+$): 310.10.

The compound of Example 4 was prepared from (7-chloro-thieno[3,2-b]pyridin-2-yl)-(3-dimethylamino-pyrrolidin-1-yl)-methanone (4a) and intermediate 3b following Method C. $^1$H NMR (300 MHz, CD$_3$OD) δ 8.43 (d, 1H, J=5.46 Hz), 7.84 (d, 1H, J=6.40 Hz), 7.65 (s, 1H), 7.43 (d, 2H, J=8.48 Hz), 7.16 (d, 2H, J=8.47 Hz), 6.76 (s, 1H), 6.67 (d, 1H, J=5.46 Hz), 4.14–3.95 (m, 3H), 3.95–3.77 (m, 2H), 3.72 (s, 2H), 3.65–3.35 (m, 2H), 2.31 (s, 6H), 2.22 (s, 6H). LCMS (ESI+) [M+H]/z Calc'd 530, found 530. Anal. (C$_{29}$H$_{31}$N$_5$O$_3$S.1.0CH$_3$COOH)C, H, N.

Example 5

7-{4-[(4,6-Dimethyl-pyridin-2-ylcarbamoyl)-methyl]-phenoxy}-thieno[3,2-b]pyridine-2-carboxylic acid (3-dimethylamino-propyl)-methyl-amide

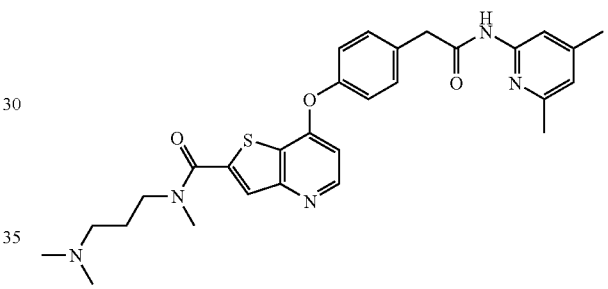

Intermediate 5a: 7-Chloro-thieno[3,2-b]pyridine-2-carboxylic acid (3-dimethylamino-propyl)-methyl-amide

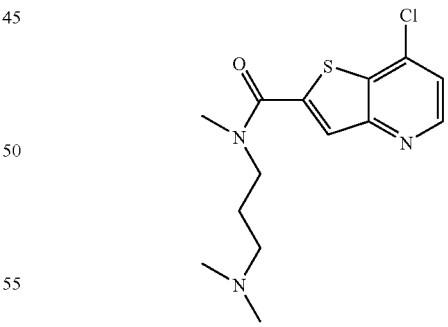

was prepared by the reaction of 7-chlorothieno[3,2-b]pyridine-2-carbonic acid (1.0 g, 4.68 mmol) with N,N,N'-trimethylpropane-1,3-diamine (0.868 mL, 4.68 mmol) and Et$_3$N (1.96 mL, 14.04 mmol) in a manner as described previously in Method A and gave intermediate 5a as a white foam (1.07 g, 77%). $^1$H NMR (300 MHz, CD$_3$OD) 38.56 (d, 1H, J=5.09 Hz), 7.76 (s, 1H), 7.46 (d, 1H, J=5.27 Hz), 3.51 (m, 2H), 3.20 (s, 3H), 2.33 (m, 2H), 2.18 (s, 6H), 1.79 (m, 2H); ESIMS (MH$^+$): 312.05.

The compound of Example 5 was prepared from 7-chloro-thieno[3,2-b]pyridine-2-carboxylic acid (3-dimethylamino-propyl)-methyl-amide (5a) and intermediate 3b following Method C. $^1$H NMR (300 MHz, CD$_3$OD) δ 8.42 (d, 1H, J=5.27 Hz), 7.76 (d, 1H, J=8.67 Hz), 7.65 (s, 1H), 7.43 (d, 2H, J=8.48 Hz), 7.15 (d, 2H, J=8.48 Hz), 6.75 (s, 1H), 6.65 (d, 1H, J=5.65 Hz), 3.71 (s, 2H), 3.56–3.51 (m, 2H), 3.08 (s, 3H), 2.60–2.43 (m, 2H), 2.30 (s, 6H), 2.22 (s, 6H), 1.90–1.81 (m, 2H). LCMS (ESI+) [M+H]/z Calc'd 532, found 532. Anal. (C$_{29}$H$_{33}$N$_5$O$_3$S.1.1CH$_3$COOH)C, H, N.

Example 6

7-{4-[(4,6-Dimethyl-pyridin-2-ylcarbamoyl)-methyl]-phenoxy}-thieno[3,2-b]pyridine-2-carboxylic acid (2-dimethylamino-ethyl)-methyl-amide

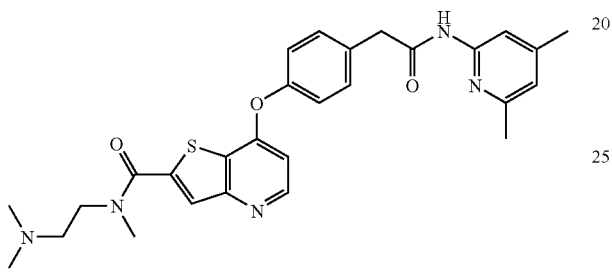

Intermediate 6a: 7-Chloro-thieno[3,2-b]pyridine-2-carboxylic acid (2-dimethylamino-ethyl)-methyl-amide

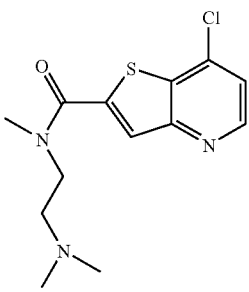

was prepared by the reaction of 7-chlorothieno[3,2-b]pyridine-2-carboxylic acid (0.957 g, 4.48 mmol) with N,N,N'-trimethylethane-1,2-diamine (0.640 mL, 4.93 mmol) and Et$_3$N (0.624 mL, 4.48 mmol) in a manner as described previously in Method A to give a brown solid (0.167 g, 13%). $^1$H NMR (400 MHz, CDCl$_3$) δ 8.60 (d, 1H, J=5.05 Hz), 7.74 (s, 1H), 7.32 (d, 1H, J=5.05 Hz), 3.66 (t, 2H, J=6.19 Hz), 3.26 (s, 3H), 2.57 (t, 2H, J=6.69 Hz), 2.25 (s, 6H). ESIMS (MH$^+$): 298.05.

The compound of Example 6 was prepared from 7-chloro-thieno[3,2-b]pyridine-2-carboxylic acid (2-dimethylamino-ethyl)-methyl-amide (6a) and intermediate 3b following Method C. $^1$H NMR (300 MHz, CD$_3$OD) δ 8.42 (d, 1H, J=5.56 Hz), 7.75 (m, 1H), 7.65 (s, 1H), 7.44 (d, 2H, J=8.59 Hz), 7.15 (d, 2H, J=8.59 Hz), 6.76 (s, 1H), 6.67 (d, 1H, J=5.56 Hz), 3.72 (s, 2H), 3.22 (s, 5H), 2.86–2.72 (m, 2H), 2.44 (s, 6H), 2.31 (s, 3H), 2.22 (s, 3H). LCMS (ESI+) [M+H]/z Calc'd 518, found 518. Anal. (C$_{28}$H$_{31}$N$_5$O$_3$S.1.0H$_2$O.0.8CH$_3$COOH)C, H, N.

Example 7

7-{4-[(4,6-Dimethyl-pyridin-2-ylcarbamoyl)-methyl]-phenoxy}-thieno[3,2-b]pyridine-2-carboxylic acid dimethylamide

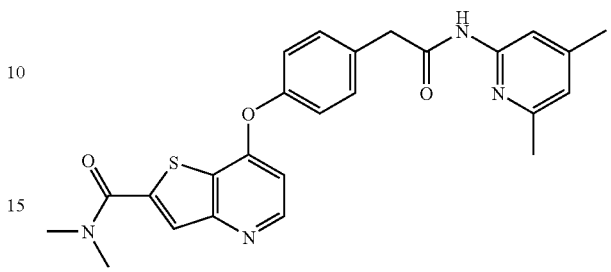

Intermediate 7a: 7-Chloro-thieno[3,2-b]pyridine-2-carboxylic acid dimethylamide

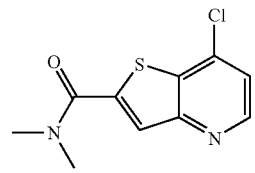

was prepared by the reaction of 7-chloro-thieno[3,2-b]pyridine-2-carboxylic acid (0.57 g, 2.67 mmol) with 2.0 M N,N-dimethylamine in THF (1.60 mL, 3.20 mmol) and Et$_3$N (0.447 mL, 3.20 mmol) in a manner as described in Method A to give the desired amide as brown solid (0.54 g, 84%). $^1$H NMR (300 MHz, CDCl$_3$) δ 8.63 (d, 1H, J=4.85 Hz), 7.74 (s, 1H), 7.35 (d, 1H, J=5.02 Hz), 3.28 (s, 3H), 3.22 (s, 3H); ESIMS (MH$^+$): 240.95.

The compound of Example 7 was prepared from 7-chloro-thieno[3,2-b]pyridine-2-carboxylic acid dimethylamide (7a) and intermediate 3b following Method C. $^1$H NMR (300 MHz, CD$_3$OD) δ 8.48 (d, 1H, J=5.27 Hz), 7.78 (d, 1H, J=8.67 Hz), 7.60 (s, 1H), 7.48 (d, 2H, J=8.48 Hz), 7.18 (d, 2H, J=8.48 Hz), 6.78 (s, 1H), 6.68 (d, 1H, J=5.65 Hz), 3.78 (s, 2H), 3.14 (s, 3H), 3.08 (s, 3H), 2.33 (s, 3H), 2.28 (s, 3H). LCMS (ESI+) [M+H]/z Calc'd 461, found 461. Anal. (C$_{25}$H$_{24}$N$_4$O$_3$S.1.0H$_2$O.0.4CH$_3$COOH)C, H, N.

Example 8

7-{4-[(5-Chloro-pyridin-2-ylcarbamoyl)-methyl]-phenoxy}-thieno[3,2-b]pyridine-2-carboxylic acid dimethylamide

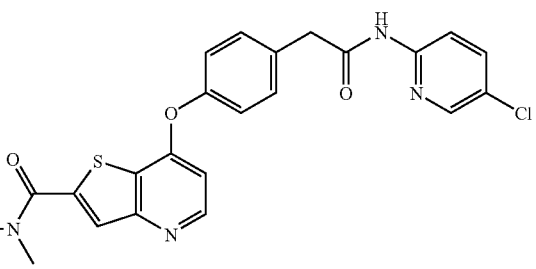

Intermediate 8a: [4-(2-Dimethylcarbamoyl-thieno[3,2-b]pyridin-7-yloxy)-phenyl]-acetic acid

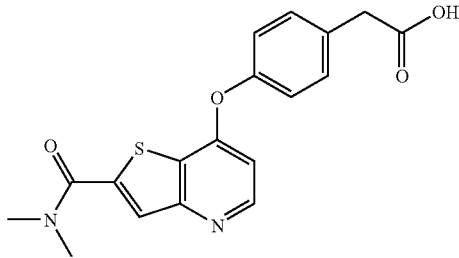

was prepared from 7-chloro-thieno[3,2-b]pyridine-2-carboxylic acid dimethylamide (7a) and 4-hydroxyphenylacetic acid following Method C. $^1$H NMR (300 MHz, DMSO-d$_6$) δ 8.56 (d, 1H, J=5.31 Hz), 7.92 (s, 1H), 7.40 (d, 2H, J=8.58 Hz), 7.24 (d, 2H, J=8.09 Hz), 6.70 (d, 1H, J=5.06 Hz), 3.64 (s, 2H), 3.33 (s, 6H). LCMS (ESI+) [M+H]/z Calc'd 357, found 357.

The compound of Example 8 was prepared from intermediate 8a and 2-amino-5-chloro pyridine following Method A. $^1$H NMR (300 MHz, CD$_3$OD) δ 8.68 (d, 1H, J=5.27 Hz), 8.32 (s, 1H), 8.22 (m, 1H), 7.68 (d, 2H, J=6.03 Hz), 7.43 (d, 2H, J=8.29 Hz), 7.15 (d, 2H, J=8.48 Hz), 6.70 (d, 1H, J=4.71 Hz), 3.74 (s, 2H), 3.21 (s, 6H). LCMS (ESI+) [M+H]/z Calc'd 467, found 467. Anal. (C$_{23}$H$_{19}$N$_4$O$_3$SCl. 0.6H$_2$O.0.6CH$_3$COOH)C, H, N.

Example 9

N-(4,6-Dimethyl-pyridin-2-yl)-2-{4-[2-(1-methyl-1H-imidazol-2-yl)-thieno[3,2-b]pyridin-7-yloxy]-phenyl}-acetamide

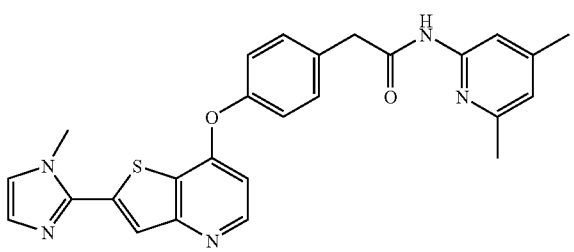

Intermediate 9a: {4-[2-(1-Methyl-1H-imidazol-2-yl)-thieno[3,2-b]pyridin-7-yloxy]-phenyl}-acetic acid

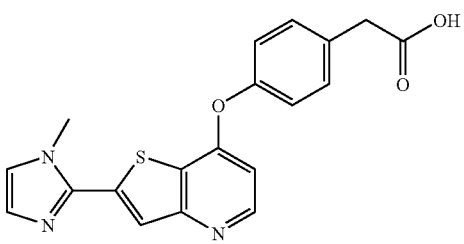

was prepared from 7-chloro-2-(1-methyl-1H-imidazol-2-yl)-thieno[3,2-b]pyridine and 4-hydroxyphenylactic acid following Method C. $^1$H NMR (300 MHz, DMSO-d$_6$) δ 8.51 (d, 1H, J=5.09), 7.88 (s, 1H), 7.40 (m, 3H), 7.24 (d, 2H, J=8.48 Hz), 7.04 (s, 1H), 6.65 (d, 1H, J=5.09 Hz), 3.98 (s, 3H), 3.64 (s, 2H). LCMS (ESI+) [M+H]/z Calc'd 366, found 366.

The compound of Example 9 was prepared from intermediate 9a and 2-amino-4,6-dimethyl-pyridine following Method A. $^1$H NMR (300 MHz, CDCl$_3$) δ 8.45 (d, 1H, J=5.84 Hz), 8.19 (d, 1H, J=5.65 Hz), 7.85 (s, 1H), 7.52 (m, 2H), 7.21 (m, 3H), 7.04(s, 1H), 6.89 (s, 1H), 6.71 (d, 1H, J=6.05 Hz), 3.98 (s, 3H), 3.90 (s, 2H), 2.59 (s, 3H), 2.45 (s, 3H). LCMS (ESI+) [M+H]/z Calc'd 470, found 470. Anal. (C$_{26}$H$_{23}$N$_5$O$_2$S.0.6H$_2$O.1.0CH$_3$COOH)C, H, N.

Example 10

N-(5-Chloro-pyridin-2-yl)-2-{4-[2-(1-methyl-1H-imidazol-2-yl)-thieno[3,2-b]pyridin-7-yloxy]-phenyl}-acetamide

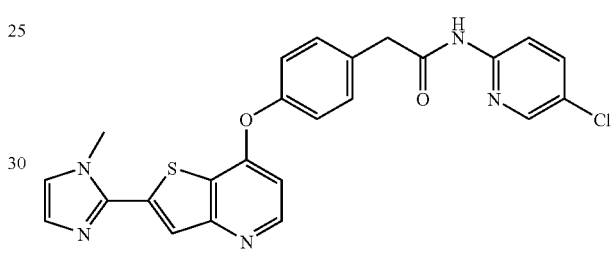

was prepared from intermediate 9a and 2-amino-5-chloro pyridine following Method A. $^1$H NMR (300 MHz, CDCl$_3$) δ 8.46 (d, 1H, J=6.22 Hz), 8.18 (m, 3H), 8.12 (s, 1H), 7.68 (m, 1H), 7.50 (d, 2H, J=8.67 Hz), 7.23(d, 2H, J=8.67 Hz), 7.10 (s, 1H), 6.78 (d, 1H, J=6.22 Hz), 4.04 (s, 3H), 3.82 (s, 2H). LCMS (ESI+) [M+H]/z Calc'd 476, found 476. Anal. (C$_{24}$H$_{18}$N$_5$O$_2$SCl.CH$_2$Cl$_2$) C, H, N.

Example 11

2-{4-[2-(1-Methyl-1H-imidazol-2-yl)-thieno[3,2-b]pyridin-7-yloxy]-phenyl}-N-(4-methyl-pyridin-2-yl)-acetamide

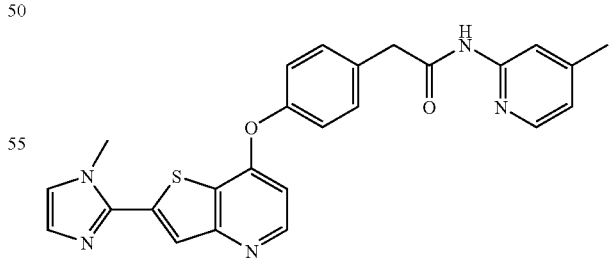

was prepared from intermediate 9a and 2-amino-4-methyl pyridine following Method A. $^1$H NMR (300 MHz, CD$_3$OD) δ 8.38 (d, 1H, J=5.65 Hz), 8.05 (d, 1H, J=5.28 Hz), 7.86 (s, 1H), 7.71 (s, 1H), 7.44 (d, 2H, J=8.29 Hz), 7.23(s, 1H), 7.16 (d, 2H, J=8.48 Hz), 7.01 (s, 1H), 6.88 (d, 1H, J=4.70 Hz), 6.63 (d, 1H, J=5.65 Hz), 3.93 (s, 3H), 3.73 (s, 2H), 2.27 (s, 3H). LCMS (ESI+) [M+H]/z Calc'd 456, found 456.

Example 12

N-Isoquinolin-3-yl-2-(4-[2-(1-methyl-1H-imidazol-2-yl)-thieno[3,2-b]pyridin-7-yloxy]-phenyl}-acetamide

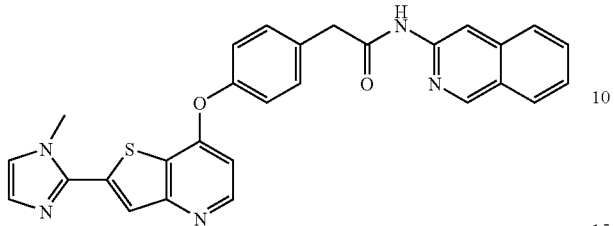

was prepared from intermediate 9a and 3-amino isoquinoline following Method A. Spectral and analytical data for the compound of Example 12: $^1$H NMR (300 MHz, CD$_3$OD) δ 8.97(s, 1H), 8.39 (d, 2H, J=5.46 Hz), 7.90 (s, 1H), 7.71 (m, 2H), 7.51(m, 1H), 7.46 (m, 3H), 7.20 (m, 3H), 7.01 (s, 1H), 6.64 (d, 1H, J=6.22 Hz), 3.94 (s, 3H), 3.82 (s, 2H). LCMS (ESI+) [M+H]/z Calc'd 492, found 492.

Example 13

2-{4-[2-(1-Methyl-1H-imidazol-2-yl)-thieno[3,2-b]pyridin-7-yloxy]-phenyl}-N-(5-trifluoromethyl-pyridin-2-yl)-acetamide

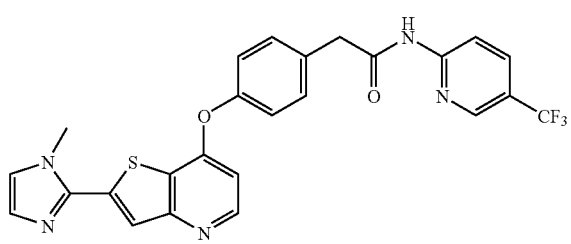

was prepared from intermediate 9a and 2-amino-5-trifluoromethyl pyridine following Method A. $^1$H NMR (300 MHz, CDCl$_3$) δ 8.51 (s, 1H), 8.38 (d, 1H, J=5.65 Hz), 8.24 (d, 1H, J=8.67 Hz), 7.96 (d, 1H, J=8.86 Hz), 7.71 (s, 1H), 7.43 (d, 2H, J=8.48 Hz), 7.23 (s, 1H), 7.16 (d, 2H, J=8.67 Hz), 7.01 (s, 1H), 6.62 (d, 1H, J=5.46 Hz), 3.93 (s, 3H), 3.77 (s, 2H). LCMS (ESI+) [M+H]/z Calc'd 510, found 510.

Example 14

N-(4,6-Dimethyl-pyridin-2-yl)-2-{4-[2-((R)-3-hydroxy-pyrrolidine-1-carbonyl)-thieno[3,2-b]pyridin-7-yloxy]-phenyl}-acetamide

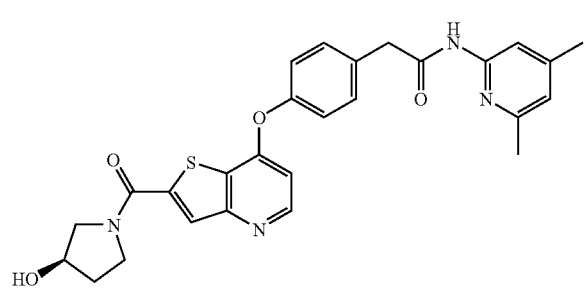

Intermediate 14a: {4-[2-((R)-3-Hydroxy-pyrrolidine-1-carbonyl)-thieno[3,2-b]pyridin-7-yloxy]-phenyl}-acetic acid

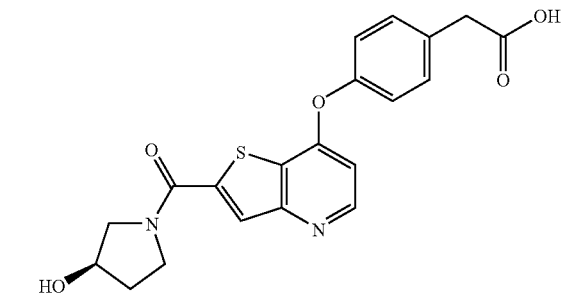

was prepared from (7-chloro-thieno[3,2-b]pyridin-2-yl)-(3-hydroxy-pyrrolidin-1-yl)-methanone (2b) and 4-hydroxyphenylacetic acid following Method C. $^1$H NMR (300 MHz, DMSO-d$_6$) δ 8.36 (d, 1H, J=4.89 Hz), 7.77 (s, 1H), 7.29 (d, 2H, J=8.47 Hz), 7.29 (d, 2H, J=8.66 Hz), 6.59 (d, 1H, J=5.47 Hz), 4.36 (bs, 1H), 3.92–3.83 (m, 2H), 3.53 (s, 2H), 3.71–3.60 (m, 3H), 2.01–1.93(m, 2H). LCMS (ESI+) [M+H]/z Calc'd 399, found 399.

The compound of Example 14 was prepared from intermediate 14a and 2-amino-4,6-dimethylpyridine following Method A. $^1$H NMR (300 MHz, CD$_3$OD) δ 8.45 (d, 1H, J=5.84 Hz), 7.82 (s, 1H), 7.65 (s, 1H), 7.44 (d, 2H, J=8.48 Hz), 7.11 (d, 2H, J=8.67 Hz), 6.76 (s, 1H), 6.67 (d, 1H, J=5.65 Hz), 4.51 (bs, 1H), 4.01–3.91 (m, 2H), 3.85 (s, 2H), 3.75–3.72 (m, 3H), 2.31 (s, 3H), 2.22 (s, 3H), 2.15–1.94 (m, 2H). LCMS (ESI+) [M+H]/z Calc'd 503, found 503. Anal. (C$_{27}$H$_{26}$N$_4$O$_4$S.0.8H$_2$O.0.8CH$_3$COOH)C, H, N.

Example 15

2-{4-[2-((R)-3-Hydroxy-pyrrolidine-1-carbonyl)-thieno[3,2-b]pyridin-7-yloxy]-phenyl}-N-(4-methyl-pyridin-2-yl)-acetamide

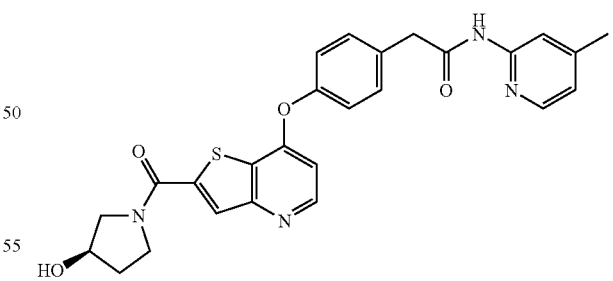

was prepared from intermediate 14a and 2-amino-4-methyl pyridine following Method A. $^1$H NMR (300 MHz, CD$_3$OD) δ 8.44 (d, 1H, J=5.28 Hz), 8.06 (d, 1H, J=5.09 Hz), 7.90–7.81 (m, 2H), 7.45 (d, 2H, J=8.29 Hz), 7.17 (d, 2H, J=8.11 Hz), 6.89 (d, 1H, J=5.65 Hz), 6.68 (d, 1H, J=5.27 Hz), 4.43 (bs, 1H), 3.98–3.93 (m, 2H), 3.74 (s, 2H), 3.67–3.61(m, 3H), 2.28 (s, 3H), 2.11–1.92 (m, 2H). LCMS (ESI+) [M+H]/z Calc'd 489, found 489. Anal. (C$_{26}$H$_{24}$N$_4$O$_4$S.1.0H$_2$O.1.0CH$_3$COOH)C, H, N.

Example 16

N-(5-Chloro-pyridin-2-yl)-2-{4-[2-((R)-3-hydroxy-pyrrolidine-1-carbonyl)-thieno[3,2-b]pyridin-7-yloxy]-phenyl}-acetamide

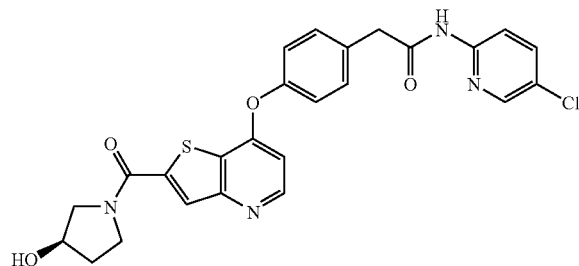

was prepared from intermediate 14a and 2-amino-5-chloro pyridine following Method A. ¹H NMR (300 MHz, CD₃OD) δ 8.43 (d, 1H, J=5.46 Hz), 8.20 (d, 1H, J=2.07 Hz), 8.05 (d, 1H, J=9.04 Hz), 7.85 (d, 1H, J=17.52 Hz), 7.72–7.66 (m, 1H), 7.44 (d, 2H, J=8.48 Hz), 7.16 (d, 2H, J=8.67 Hz), 6.68 (d, 1H, J=5.66 Hz), 4.52 (bs, 1H), 3.99–3.93 (m, 2H), 3.74 (s, 2H), 3.68–3.60(m, 3H), 2.11–1.92(m, 2H). LCMS (ESI+) [M+H]/z Calc'd 509, found 509.

Example 17

2-{4-[2-((R)-3-Hydroxy-pyrrolidine-1-carbonyl)-thieno[3,2-b]pyridin-7-yloxy]-phenyl}-N-isoquinolin-3-yl-acetamide

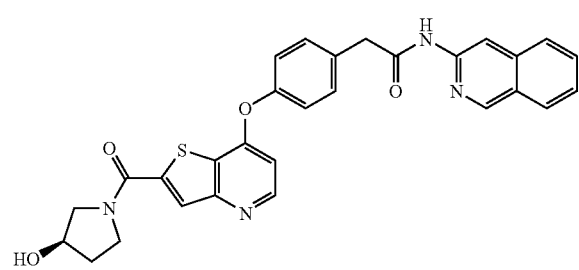

was prepared from intermediate 14a and 3-amino-isoquinoline following Method A. ¹H NMR (300 MHz, CD₃OD) δ 8.97 (s, 1H), 8.45–8.36 (m, 2H), 7.91–7.81 (m, 2H), 7.74 (d, 1H, J=8.10 Hz), 7.62–7.57 (m, 1H), 7.51–7.41 (m, 3H), 7.18 (d, 2H, J=8.48 Hz), 6.68 (d, 1H, J=5.65 Hz), 4.44 (bs, 1H), 4.02–3.91 (m, 2H), 3.80 (s, 2H), 3.75–3.60 (m, 3H), 2.10–1.91 (m, 2H). LCMS (ESI+) [M+H]/z Calc'd 525, found 525. Anal. (C₂₉H₂₄N₄O₄S.0.8CH₂Cl₂) C, H, N.

Example 18

2-{4-[2-((R)-3-Hydroxy-pyrrolidine-1-carbonyl)-thieno[3,2-b]pyridin-7-yloxy]-phenyl}-N-(5-trifluoromethyl-pyridin-2-yl)-acetamide

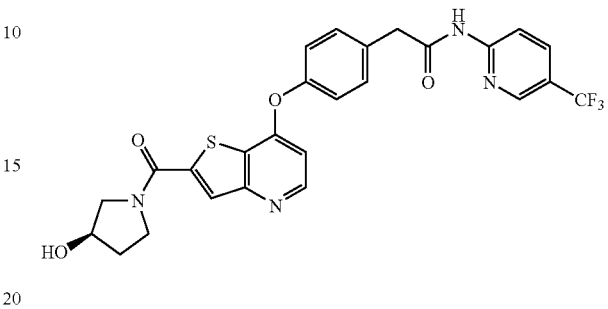

was prepared from intermediate 14a and 2-amino-5-trifluoro-methyl pyridine following Method A. ¹H NMR (300 MHz, CD₃OD) δ 8.51 (s, 1H), 8.42 (d, 1H, J=5.27 Hz), 8.23 (d, 1H, J=8.29 Hz), 7.95 (d, 1H, J=8.48 Hz), 7.84 (d, 1H, J=17.71 Hz), 7.43 (d, 2H, J=8.29 Hz), 7.15 (d, 2H, J=8.66 Hz), 6.66 (d, 1H, J=5.47 Hz), 4.41 (bs, 1H), 3.99–3.91 (m, 2H), 3.77 (s, 2H), 3.71–3.59 (m, 3H), 2.07–1.98 (m, 2H). LCMS (ESI+) [M+H]/z Calc'd 543, found 543.

Example 19

2-{4-[2-((R)-3-Hydroxy-pyrrolidine-1-carbonyl)-thieno[3,2-b]pyridin-7-yloxy]-phenyl}-N-pyridin-2-yl-acetamide

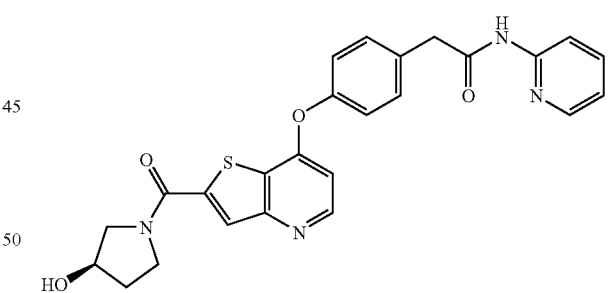

was prepared from intermediate 14a and 2-aminopyridine following Method A. Spectral and analytical data for the compound of Example 19: ¹H NMR (300 MHz, CD₃OD) δ 8.53 (d, 1H, J=5.27 Hz), 8.27 (s, 1H), 8.11 (d, 1H, J=8.48 Hz), 7.98 (d, 1H, J=17.71 Hz), 7.85–7.71 (m, 1H), 7.52 (d, 2H, J=8.66 Hz), 7.31 (d, 2H, J=8.66 Hz), 7.18–7.09 (m, 1H), 6.72 (d, 1H, J=5.47 Hz), 4.42 (bs, 1H), 4.18–3.98 (m, 2H), 3.88–3.55 (m, 5H), 2.21–1.98 (m, 2H). LCMS (ESI+) [M+H]/z Calc'd 475, found 475. Anal. (C₂₅H₂₂N₄O₄S.1.2CH₂Cl₂) C, H, N.

Example 20

2-{4-[2-((R)-3-Hydroxy-pyrrolidine-1-carbonyl)-thieno[3,2-b]pyridin-7-yloxy]-phenyl}-N-phenyl-acetamide

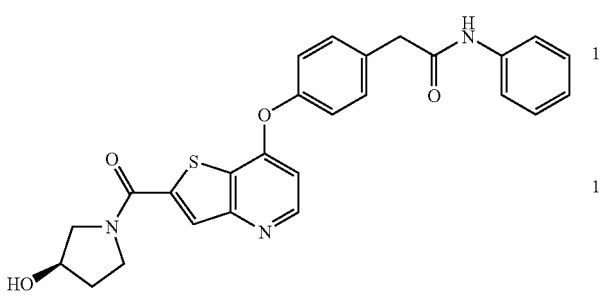

was prepared from intermediate 14a and aniline following Method A. Spectral and analytical data for the compound of Example 20: ¹H NMR (300 MHz, CD₃OD) δ 8.41 (d, 1H, J=5.65 Hz), 7.83 (d, 1H, J=17.52 Hz), 7.53–7.38 (m, 4H), 7.26–7.11 (m, 4H), 7.03–6.95 (m, 1H), 6.65 (d, 1H, J=5.65 Hz), 4.42 (bs, 1H), 4.04–3.89 (m, 2H), 3.76–3.56 (m, 5H), 2.12–1.98 (m, 2H). LCMS (ESI+) [M+H]/z Calc'd 474, found 474. Anal. (C$_{26}$H$_{23}$N$_3$O$_4$S.0.6CH$_2$Cl$_2$) C, H, N.

Example 21

2-{4-[2-(Azetidine-1-carbonyl)-thieno[3,2-b]pyridin-7-yloxy]-phenyl}-N-(6-methoxy-pyridin-3-yl)-acetamide

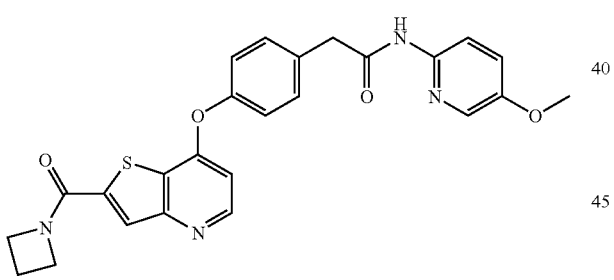

Intermediate 21a: Azetidin-1-yl-(7-chloro-thieno[3,2-b]pyridin-2-yl)-methanone

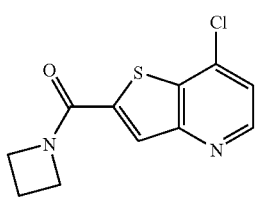

was prepared from 7-chloro-thieno[3,2-b]pyridine-2-carboxylic acid and azetidine hydrochloride following Method A. ¹H NMR (300 MHz, DMSO-d₆) δ 8.72 (1H, d, J=5.1 Hz), 7.96 (1H, s), 7.70 (1H, d, J=5.1 Hz), 4.62 (2H, t, J=7.4 Hz), 4.12 (2H, t, J=7.7 Hz), 2.34 (2H, tt, J=7.4, 7.7 Hz).

Intermediate 21b: {4-[2-(Azetidine-1-carbonyl)-thieno[3,2-b]pyridin-7-yloxy]-phenyl}-acetic acid

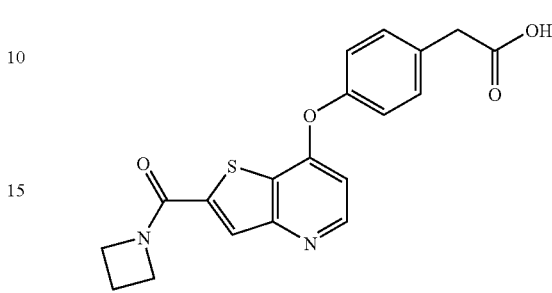

was prepared from azetidin-1-yl-(7-chloro-thieno[3,2-b]pyridin-2-yl)-methanone (21a) and 4-hydroxyphenylacetic acid following Method C. ¹H NMR (300 MHz, DMSO-d₆) δ 8.57 (d, 1H, J=5.27 Hz), 7.88(s, 1H), 7.40 (d, 2H, J=8.10 Hz), 7.24 (d, 2H, J=8.10 Hz), 6.70 (d, 1H, J=5.08 Hz), 4.70–4.52 (m, 2H), 4.18–4.00 (m, 2H), 3.64 (s, 2H), 2.46–2.34(m, 2H). LCMS (ESI+) [M+H]/z Calc'd 369, found 369.

The compound of Example 21 was prepared from intermediate 21b and 5-amino-2-methoxy-pyridine following Method A. ¹H NMR (300 MHz, CD₃OD) δ 8.43 (d, 1H, J=5.66 Hz), 8.23 (d, 1H, J=2.45 Hz), 7.83–7.79 (m, 1H), 7.74 (s, 1H), 7.43 (d, 2H, J=8.48 Hz), 7.15 (d, 2H, J=8.67 Hz), 6.71–6.66 (m, 2H), 4.64–4.57 (m, 2H), 4.22–4.13 (m, 2H), 3.79 (s, 3H), 3.67 (s, 2H), 2.44–2.34(m, 2H). LCMS (ESI+) [M+H]/z Calc'd 475, found 475.

Example 22

2-{4-[2-(Azetidine-1-carbonyl)-thieno[3,2-b]pyridin-7-yloxy]-phenyl}-N-(4,6-dimethyl-pyridin-2-yl)-acetamide

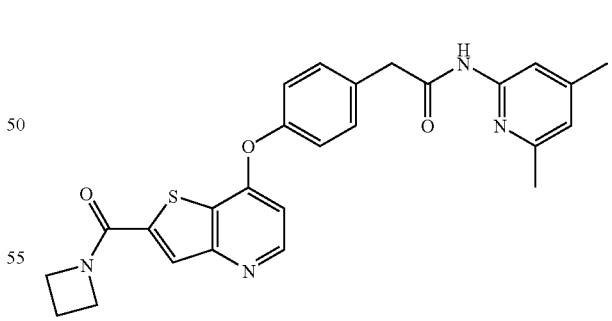

was prepared from intermediate 21b and 2-amino-4,6-dimethylpyridine following Method A. ¹H NMR (300 MHz, CDCl₃) δ 8.50 (d, 1H, J=5.27 Hz), 8.03 (s, 1H), 7.77 (s, 1H), 7.47 (d, 2H, J=8.29 Hz), 7.18 (d, 2H, J=8.29 Hz), 6.81 (s, 1H), 6.64 (d, 1H, J=5.28 Hz), 4.67–4.63 (m, 2H), 4.34–4.22 (m, 2H), 3.82 (s, 2H), 2.48 (s, 3H), 2.46–2.40(m, 2H), 2.37 (s, 3H). LCMS (ESI+) [M+H]/z Calc'd 473, found 473. Anal. (C$_{26}$H$_{24}$N$_4$O$_3$S.0.85CH$_2$Cl$_2$.0.5EtOAc) C, H, N.

Example 23

2-{4-[2-(Azetidine-1-carbonyl)-thieno[3,2-b]pyridin-7-yloxy]-phenyl}-N-(4-methyl-pyridin-2-yl)-acetamide

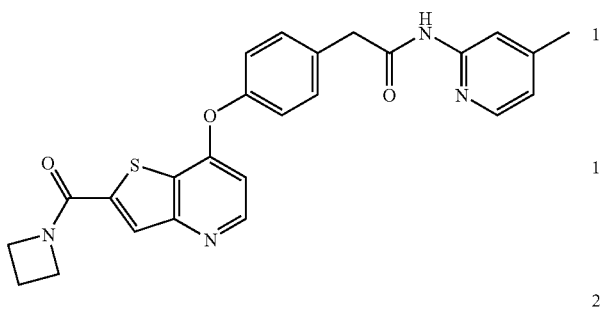

was prepared from intermediate 21b and 2-amino-4-methyl pyridine following Method A. $^1$H NMR (300 MHz, CD$_3$OD) δ 8.42 (d, 1H, J=5.47 Hz), 8.05 ((d, 1H, J=5.09 Hz), 7.85 (s, 1H), 7.73 (s, 1H), 7.43 (d, 2H, J=8.48 Hz), 7.15 (d, 2H, J=8.66 Hz), 6.88 ((d, 1H, J=5.65 Hz), 6.66 (d, 1H, J=5.65 Hz), 4.65–4.54 (m, 2H), 4.22–4.12(m, 2H), 3.74 (s, 2H), 2.45–2.34(m, 2H), 2.27 (s, 3H). LCMS (ESI+) [M+H]/z Calc'd 459, found 459. Anal. (C$_{25}$H$_{22}$N$_4$O$_3$S.0.4CH$_2$Cl$_2$) C, H, N.

Example 24

2-{4-[2-(Azetidine-1-carbonyl)-thieno[3,2-b]pyridin-7-yloxy]-phenyl}-N-(5-methyl-pyridin-2-yl)-acetamide

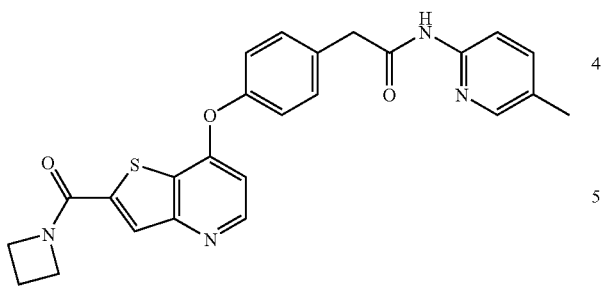

was prepared from intermediate 21b and 2-amino-5-methyl pyridine following Method A. $^1$H NMR (300 MHz, CD$_3$OD) δ 8.42 (d, 1H, J=5.46 Hz), 8.05 ((s, 1H), 7.88 (d, 1H, J=8.48 Hz), 7.75 (s, 1H), 7.54–7.49 (m, 1H), 7.43 (d, 2H, J=8.67 Hz), 7.15 (d, 2H, J=8.66 Hz), 6.66 (d, 1H, J=5.47 Hz), 4.65–4.56 (m, 2H), 4.22–4.12 (m, 2H), 3.73 (s, 2H), 2.45–2.34 (m, 2H), 2.21 (s, 3H). LCMS (ESI+) [M+H]/z Calc'd 459, found 459. Anal. (C$_{25}$H$_{22}$N$_4$O$_3$S.0.3CH$_2$Cl$_2$) C, H, N.

Example 25

2-{4-[2-(Azetidine-1-carbonyl)-thieno[3,2-b]pyridin-7-yloxy]-phenyl}-N-(6-methyl-pyridin-2-yl)-acetamide

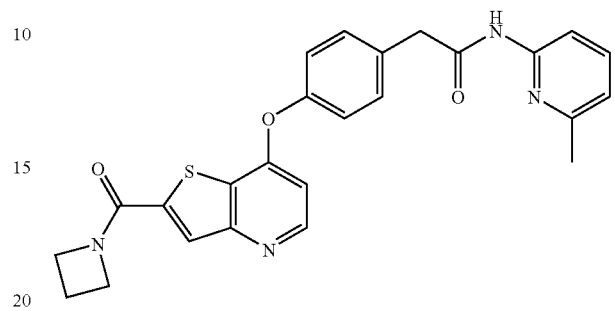

was prepared from intermediate 21b and 2-amino-6-methyl pyridine following Method A. $^1$H NMR (300 MHz, CD$_3$OD) δ 8.41 (d, 1H, J=5.65 Hz), 7.78 (d, 1H, J=8.29 Hz), 7.72 (s, 1H), 7.56–7.51 (m, 1H), 7.43 (d, 2H, J=8.66 Hz), 7.15 (d, 2H, J=8.48 Hz), 6.88 (d, 1H, J=7.54 Hz), 6.66 (d, 1H, J=5.47 Hz), 4.60–4.55 (m, 2H), 4.21–4.12 (m, 2H), 3.72 (s, 2H), 2.45–2.36 (m, 2H), 2.34 (s, 3H). LCMS (ESI+) [M+H]/z Calc'd 459, found 459. Anal. (C$_{25}$H$_{22}$N$_4$O$_3$S.0.6EtOAc.0.4H$_2$O)C, H, N.

Example 26

2-{4-[2-(Azetidine-1-carbonyl)-thieno[3,2-b]pyridin-7-yloxy]-phenyl}-N-(3-methyl-pyridin-2-yl)-acetamide

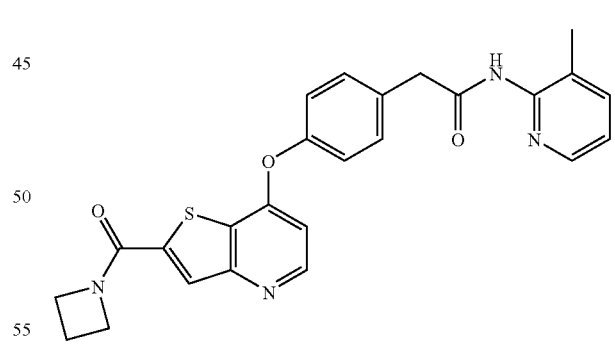

was prepared from intermediate 21b and 2-amino-3-methyl pyridine following Method A. $^1$H NMR (300 MHz, CD$_3$OD) δ 8.41 (d, 1H, J=5.46 Hz), 8.15 (d, 1H, J=4.52 Hz), 7.71 (s, 1H), 7.62 (d, 1H, J=7.72 Hz), 7.45 (d, 2H, J=8.29 Hz), 7.19–7.06 (m, 3H), 6.63 (d, 1H, J=5.47 Hz), 4.63–4.52 (m, 2H), 4.21–4.08 (m, 2H), 3.73 (s, 2H), 2.42–2.29 (m, 2H), 2.11 (s, 3H). LCMS (ESI+) [M+H]/Z Calc'd 459, found 459.

Example 27

2-{4-[2-(Azetidine-1-carbonyl)-thieno[3,2-b]pyridin-7-yloxy]-phenyl}-N-(5-trifluoromethyl-pyridin-2-yl)-acetamide

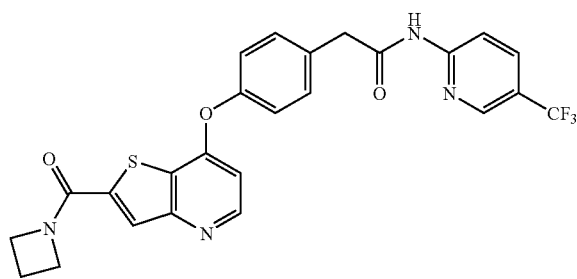

was prepared from intermediate 21b and 2-amino-5-trifluoro-methyl pyridine following Method A. $^1$H NMR (300 MHz, CD$_3$OD) δ 8.61 (s, 1H), 8.42 (d, 1H, J=5.65 Hz), 8.22 (d, 1H, J=8.85 Hz), 7.95 (d, 1H, J=9.04 Hz), 7.74 (s, 1H), 7.43 (d, 2H, J=8.48 Hz), 7.15 (d, 2H, J=8.48 Hz), 6.66 (d, 1H, J=5.46 Hz), 4.63–4.55 (m, 2H), 4.21–4.12(m, 2H), 3.76 (s, 2H), 2.45–2.36 (m, 2H). LCMS (ESI+) [M+H]/z Calc'd 513, found 513.

Example 28

2-{4-[2-(Azetidine-1-carbonyl)-thieno[3,2-b]pyridin-7-yloxy]-phenyl}-N-(5-chloro-pyridin-2-yl)-acetamide

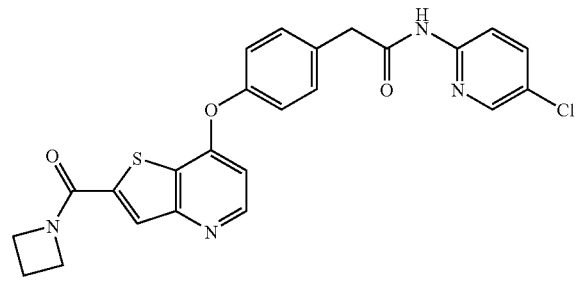

was prepared from intermediate 21b and 2-amino-5-chloro pyridine following Method A. $^1$H. NMR (300 MHz, CD$_3$OD) δ 8.42 (d, 1H, J=5.46 Hz), 8.18 (d, 1H, J=2.07 Hz), 8.03 (d, 1H, J=8.85 Hz), 7.73 (s, 1H), 7.70–7.66 (m, 1H), 7.42 (d, 2H, J=8.48 Hz), 7.15 (d, 2H, J=8.48 Hz), 6.66 (d, 1H, J=5.46 Hz), 4.63–4.55 (m, 2H), 4.21–4.12 (m, 2H), 3.72 (s, 2H), 2.45–2.36 (m, 2H). LCMS (ESI+) [M+H]/z Calc'd 479, found 479. Anal. (C$_{24}$H$_{19}$N$_4$O$_3$SCl.0.5H$_2$O.0.8CH$_3$COOH)C, H, N.

Example 29

2-{4-[2-(Azetidine-1-carbonyl)-thieno[3,2-b]pyridin-7-yloxy]-phenyl}-N-(5-fluoro-pyridin-2-yl)-acetamide

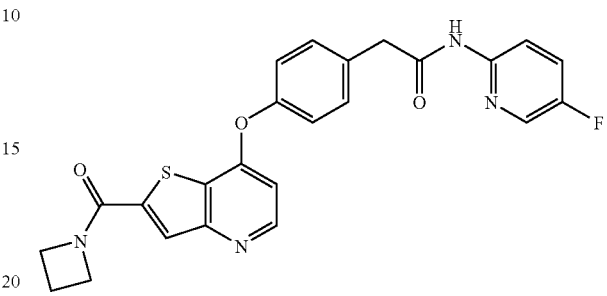

was prepared from intermediate 21b and 2-amino-5-fluoro pyridine following Method A. $^1$H NMR (300 MHz, CD$_3$OD) δ 8.42 (d, 1H, J=5.46 Hz), 8.12 (d, 1H, J=3.20 Hz), 8.10–8.02 (m, 1H), 7.75 (s, 1H), 7.64–7.48 (m, 1H), 7.45 (d, 2H, J=8.67 Hz), 7.15 (d, 2H, J=8.48 Hz), 6.67 (d, 1H, J=5.65 Hz), 4.66–4.57 (m, 2H), 4.21–4.12(m, 2H), 3.73 (s, 2H), 2.45–2.36 (m, 2H). LCMS (ESI+) [M+H]/z Calc'd 463, found 463. Anal. (C$_{24}$H$_{19}$N$_4$O$_3$SF.0.8CH$_3$COOH)C, H, N.

Example 30

2-{4-[2-(Azetidine-1-carbonyl)-thieno[3,2-b]pyridin-7-yloxy]-phenyl}-N-(5-bromo-pyridin-2-yl)-acetamide

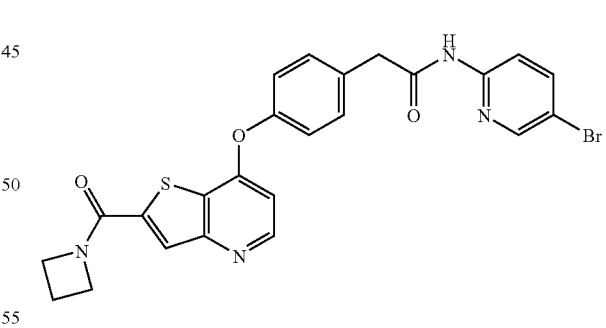

was prepared from intermediate 21b and 2-amino-5-bromo pyridine following Method A. $^1$H NMR (300 MHz, CD$_3$OD) δ 8.42 (d, 1H, J=5.46 Hz), 8.29 (d, 1H, J=2.64 Hz), 7.99 (d, 1H, J=8.67 Hz), 7.85–7.78 (m, 1H), 7.74 (s, 1H), 7.43 (d, 2H, J=8.67 Hz), 7.15 (d, 2H, J=8.66 Hz), 6.67 (d, 1H, J=5.46 Hz), 4.66–4.55 (m, 2H), 4.21–4.12 (m, 2H), 3.73 (s, 2H), 2.45–2.36 (m, 2H). LCMS (ESI+) [M+H]/z Calc'd 524, found 524. Anal. (C$_{24}$H$_{19}$N$_4$O$_3$SBr.1.0CH$_3$COOH)C, H, N.

Example 31

2-{4-[2-(Azetidine-1-carbonyl)-thieno[3,2-b]pyridin-7-yloxy]-phenyl}-N-isoquinolin-3-yl-acetamide

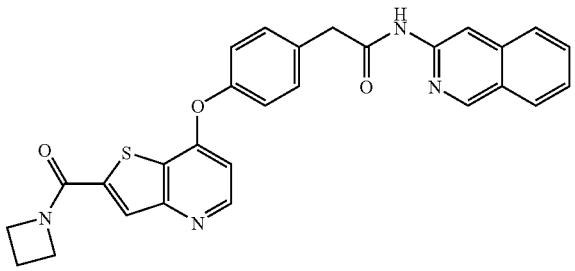

was prepared from intermediate 21b and 3-aminoisoquinoline following Method A. $^1$H NMR (300 MHz, CDCl$_3$) δ 8.95 (s, 1H), 8.61 (s, 1H), 8.52 (d, 1H, J=5.66 Hz), 8.41 (s, 1H), 7.92–7.88 (m, 2H), 7.81 (d, 1H, J=8.29 Hz), 7.70–7.63 (m, 1H), 7.50 (d, 2H, J=8.48 Hz), 7.22 (d, 2H, J=8.66 Hz), 6.73 (d, 1H, J=5.66 Hz), 4.66–4.55 (m, 2H), 4.34–4.24 (m, 2H), 3.86 (s, 2H), 2.52–2.39 (m, 2H). LCMS (ESI+) [M+H]/z Calc'd 495, found 495. Anal. (C$_{28}$H$_{22}$N$_4$O$_3$S. 0.4CH$_2$Cl$_2$) C, H, N.

Example 32

2-{4-[2-(Azetidine-1-carbonyl)-thieno[3,2-b]pyridin-7-yloxy]-phenyl}-N-isoquinolin-1-yl-acetamide

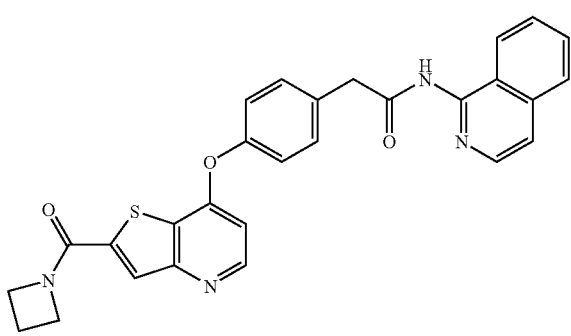

was prepared from intermediate 21b and 1-aminoisoquinoline following Method A. $^1$H NMR (300 MHz, CD$_3$OD) δ 8.42 (d, 1H, J=5.56 Hz), 8.20 (d, 1H, J=5.81 Hz), 7.99–7.93 (m, 1H), 7.86 (d, 1H, J=8.08 Hz), 7.73 (s, 1H), 7.73–7.66 (m, 1H), 7.62 (d, 1H, J=5.81 Hz), 7.58–7.54 (m, 1H), 7.51 (d, 2H, J=8.33 Hz), 7.17 (d, 2H, J=8.34 Hz), 6.64 (d, 1H, J=5.56 Hz), 4.63–4.55 (m, 2H), 4.21–4.12 (m, 2H), 3.89 (s, 2H), 2.45–2.33 (m, 2H). LCMS (ESI+) [M+H]/z Calc'd 495, found 495.

Example 33

2-{4-[2-(Azetidine-1-carbonyl)-thieno[3,2-b]pyridin-7-yloxy]-phenyl}-N-quinolin-2-yl-acetamide

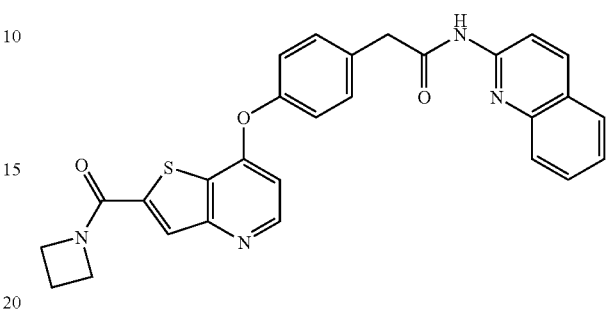

was prepared from intermediate 21b and 2-aminoquinoline following Method A. $^1$H NMR (300 MHz, CDCl$_3$) δ 8.71 (d, 1H, J=9.23 Hz), 8.60 (d, 1H, J=9.42 Hz), 8.54 (d, 1H, J=6.03 Hz), 8.19 (s, 1H), 8.01–7.93 (m, 3H), 7.75 (d, 1H, J=5.84 Hz), 7.68 (d, 2H, J=8.29 Hz), 7.26 (d, 2H, J=8.48 Hz), 7.01 (d, 1H, J=6.22 Hz), 4.71–4.63 (m, 2H), 4.32–4.25 (m, 2H), 4.14 (s, 2H), 2.63–2.43 (m, 2H). LCMS (ESI+) [M+H]/z Calc'd 495, found 495.

Example 34

2-{4-[2-(Azetidine-1-carbonyl)-thieno[3,2-b]pyridin-7-yloxy]-phenyl}-N-pyridin-3-yl-acetamide

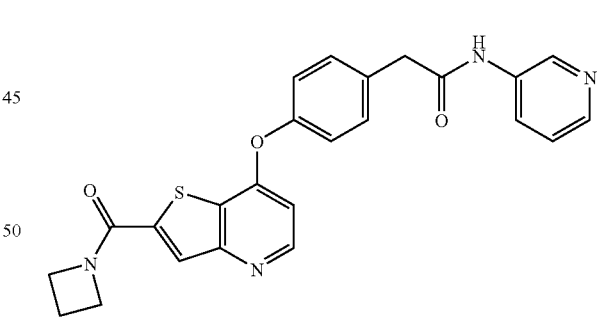

was prepared from intermediate 21b and 3-aminopyridine following Method A. $^1$H NMR (300 MHz, CD$_3$OD) δ8.66 (d, 1H, J=2.26 Hz), 8.42 (d, 1H, J=5.46 Hz), 8.19–8.15 (m, 1H), 8.07–8.02 (m, 1H), 7.73 (s, 1H), 7.43 (d, 2H, J=8.48 Hz), 7.34–7.27 (m, 1H), 7.15 (d, 2H, J=8.33 Hz), 6.66 (d, 1H, J=5.47 Hz), 4.63–4.55 (m, 2H), 4.21–4.12 (m, 2H), 3.71 (s, 2H), 2.45–2.33 (m, 2H). LCMS (ESI+) [M+H]/z Calc'd 445, found 445. Anal. (C$_{24}$H$_{20}$N$_4$O$_3$S.0.3CH$_2$Cl$_2$. 0.4EtOAc) C, H, N.

Example 35

2-{4-[2-(Azetidine-1-carbonyl)-thieno[3,2-b]pyridin-7-yloxy]-phenyl}-N-pyridin-4-yl-acetamide

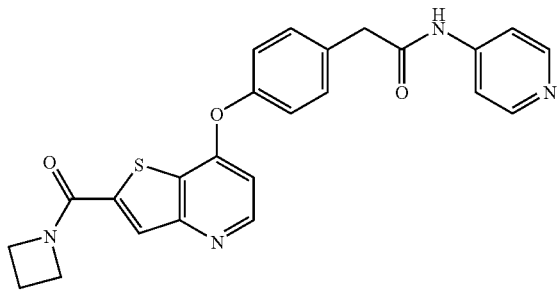

was prepared from intermediate 21b and 4-aminopyridine following Method A. ¹H NMR (300 MHz, CD₃OD) δ 8.42 (d, 1H, J=5.46 Hz), 8.30 (d, 2H, J=6.21 Hz), 7.74 (s, 1H), 7.58 (d, 2H, J=6.60 Hz), 7.43 (d, 2H, J=8.67 Hz), 7.15 (d, 2H, J=8.48 Hz), 6.66 (d, 1H, J=5.65 Hz), 4.63–4.55 (m, 2H), 4.21–4.12 (m, 2H), 3.72 (s, 2H), 2.45–2.33 (m, 2H). LCMS (ESI+) [M+H]/z Calc'd 445, found 445.

Example 36

2-{4-[2-(Azetidine-1-carbonyl)-thieno[3,2-b]pyridin-7-yloxy]-phenyl}-N-(1H-indazol-5-yl)-acetamide

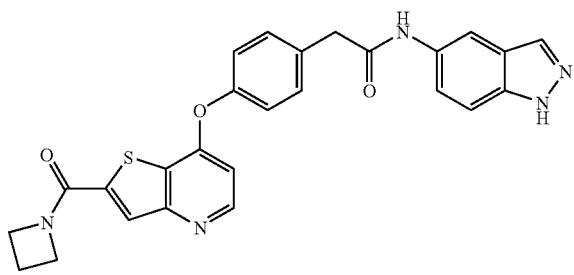

was prepared from intermediate 21b and 5-aminoindazole following Method A. ¹H NMR (300 MHz, CD₃OD) δ 8.42 (d, 1H, J=6.32 Hz), 8.00 (bs, 1H), 7.74 (s, 1H), 7.46 (d, 2H, J=9.36 Hz), 7.40 (s, 1H), 7.80 (d, 2H, J=8.34 Hz), 7.15 (d, 2H, J=10.11 Hz), 6.66 (d, 1H, J=5.81 Hz), 4.63–4.55 (m, 2H), 4.21–4.12 (m, 2H), 3.70 (s, 2H), 2.43–2.36 (m, 2H). LCMS (ESI+) [M+H]/z Calc'd 484, found 484.

Example 37

2-{4-[2-(Azetidine-1-carbonyl)-thieno[3,2-b]pyridin-7-yloxy]-phenyl}-N-benzothiazol-6-yl-acetamide

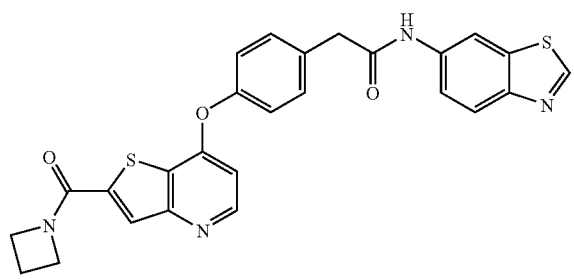

was prepared from intermediate 21b and 6-aminobenzothiazole following Method A. ¹H NMR (300 MHz, CD₃OD) δ 9.06 (s, 1H), 8.45 (1H, J=2.02 Hz), 8.42 (d, 1H, J=5.56 Hz), 7.91 (1H, J=8.85 Hz)), 7.74 (s, 1H), 7.54–7.49 (m, 1H), 7.45 (d, 2H, J=8.59 Hz), 7.16 (d, 2H, J=8.59 Hz), 6.67 (d, 1H, J=5.56 Hz), 4.64–4.53 (m, 2H), 4.21–4.12 (m, 2H), 3.73 (s, 2H), 2.43–2.36 (m, 2H). LCMS (ESI+) [M+H]/z Calc'd 501, found 501. Anal. (C₂₆H₂₀N₄O₃S₂.0.2CH₂Cl₂) C, H, N.

Example 38

2{-4-[2-(Azetidine-1-carbonyl)-thieno[3,2-b]pyridin-7-yloxy]-phenyl}-N-(6-morpholin-4-yl-pyridin-3-yl)-acetamide

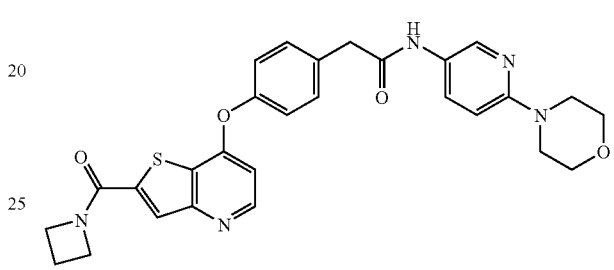

was prepared from intermediate 21b and 6-morpholin-4-yl-pyridin-3-ylamine following Method A. ¹H NMR (300 MHz, CD₃OD) δ 8.43 (d, 1H, J=5.46 Hz), 8.33 (d, 1H, J=2.26 Hz), 7.78–7.72 (m, 2H), 7.43 (d, 2H, J=8.48 Hz), 7.15 (d, 2H, J=8.48 Hz), 6.73 (d, 1H, J=9.04 Hz), 6.67 (d, 1H, J=5.47 Hz), 4.63–4.55 (m, 2H), 4.21–4.15(m, 2H), 3.74–3.64 (m, 6H), 3.37–3.30 (m, 4H), 2.45–2.33 (m, 2H). LCMS (ESI+) [M+H]/z Calc'd 530, found 530. Anal. (C₂₈H₂₇N₅O₄S.0.1CH₂Cl₂.1.0MeOH) C, H, N.

Example 39

2-{4-[2-(Azetidine-1-carbonyl)-thieno[3,2-b]pyridin-7-yloxy]-phenyl}-N-(5-methyl-1H-pyrazol-3-yl)-acetamide

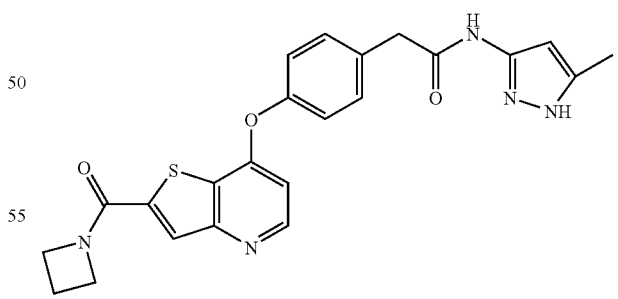

was prepared from intermediate 21b and 3-amino-5-methylpyrazole following Method A. ¹H NMR (300 MHz, CD₃OD) δ 8.43 (d, 1H, J=5.46 Hz), 7.75 (s, 1H), 7.43 (d, 2H, J=8.48 Hz), 7.15 (d, 2H, J=8.48 Hz), 6.66 (d, 1H, J=5.47 Hz), 5.19 (s, 1H), 4.66–4.57 (m, 2H), 4.21–4.15(m, 2H), 3.68 (s, 2H), 2.45–2.33 (m, 2H), 2.07 (s, 3H). LCMS (ESI+) [M+H]/z Calc'd 448, found 448. Anal. (C₂₃H₂₁N₅O₃S.1.1H₂O) C, H, N.

Example 40

2-{4-[2-(Azetidine-1-carbonyl)-thieno[3,2-b]pyridin-7-yloxy]-phenyl}-N-(1H-pyrazol-3-yl)-acetamide

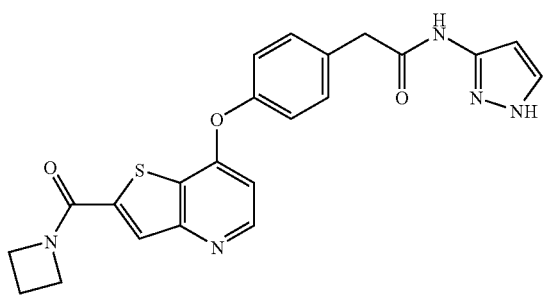

was prepared from intermediate 21b and 2-aminopyrazole following Method A. $^1$H NMR (300 MHz, CD$_3$OD) δ 8.43 (d, 1H, J=5.46 Hz), 7.75 (s, 1H), 7.43 (d, 3H, J=8.48 Hz), 7.15 (d, 2H, J=8.48 Hz), 6.67 (d, 1H, J=5.47 Hz), 6.46–6.42 (m, 1H), 4.66–4.57 (m, 2H), 4.21–4.15(m, 2H), 3.68 (s, 2H), 2.45–2.33 (m, 2H). LCMS (ESI+) [M+H]/z Calc'd 434, found 434.

Example 41

2-{4-[2-(Azetidine-1-carbonyl)-thieno[3,2-b]pyridin-7-yloxy]-phenyl}-N-(5-methyl-isoxazol-3-yl)-acetamide

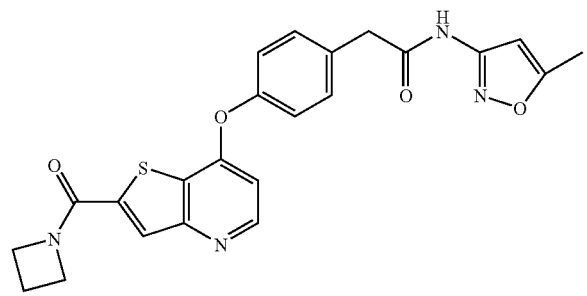

was prepared from intermediate 21b and 3-amino-5-methyl isoxazole following Method A. $^1$H NMR (300 MHz, CD$_3$OD) δ 8.43 (d, 1H, J=5.65 Hz), 7.75 (s, 1H), 7.40 (d, 2H, J=8.48 Hz), 7.15 (d, 2H, J=8.66 Hz), 6.66 (d, 1H, J=5.65 Hz), 6.51 (s, 1H), 4.66–4.57 (m, 2H), 4.21–4.15 (m, 2H), 3.70 (s, 2H), 2.45–2.33 (m, 2H), 2.07 (s, 3H). LCMS (ESI+) [M+H]/z Calc'd 449, found 449. Anal. (C$_{23}$H$_{20}$N$_4$O$_4$S.0.55CH$_2$Cl$_2$) C, H, N.

Example 42

2-{4-[2-(Azetidine-1-carbonyl)-thieno[3,2-b]pyridin-7-yloxy]-phenyl}-N-isoxazol-3-yl-acetamide

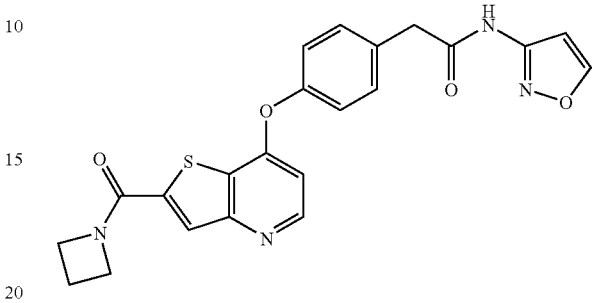

was prepared from intermediate 21b and 3-aminoisoxazole following Method A. $^1$H NMR (300 MHz, CD$_3$OD) δ 8.43 (m, 2H), 7.74 (s, 1H), 7.42 (d, 2H, J=8.67 Hz), 7.16 (d, 2H, J=8.48 Hz), 6.66 (d, 1H, J=5.46 Hz), 6.51 (s, 1H), 4.66–4.57 (m, 2H), 4.21–4.15 (m, 2H), 3.72 (s, 2H), 2.45–2.33 (m, 2H). LCMS (ESI+) [M+H]/z Calc'd 435, found 435. Anal. (C$_{22}$H$_{18}$N$_4$O$_4$S.0.2CH$_2$Cl$_2$) C, H, N.

Example 43

2-{4-[2-(Azetidine-1-carbonyl)-thieno[3,2-b]pyridin-7-yloxy]-phenyl}-N-(3,4-dimethyl-isoxazol-5-yl)-acetamide

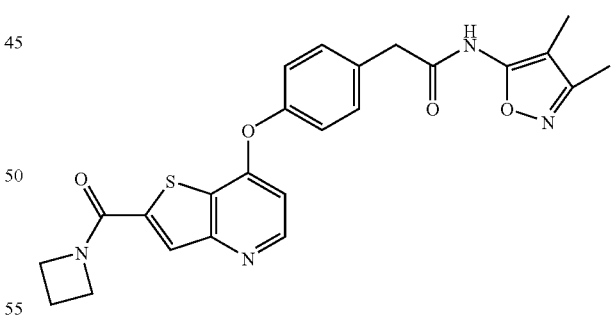

was prepared from intermediate 21b and 3,4-dimethyl-5-amino isoxazole following Method A.

$^1$H NMR (300 MHz, CD$_3$OD) δ 8.44 (d, 1H, J=5.47 Hz), 7.75 (s, 1H), 7.42 (d, 2H, J=8.10 Hz), 7.16 (d, 2H, J=8.48 Hz), 6.67 (d, 1H, J=5.46 Hz), 4.66–4.57 (m, 2H), 4.21–4.15 (m, 2H), 3.72 (s, 2H), 2.45–2.33 (m, 2H), 2.11 (s, 3H), 1.77 (s, 3H). LCMS (ESI+) [M+H]/z Calc'd 463, found 463.

Example 44

2-{4-[2-(Azetidine-1-carbonyl)-thieno[3,2-b]pyridin-7-yloxy]-phenyl}-N-thiazol-2-yl-acetamide

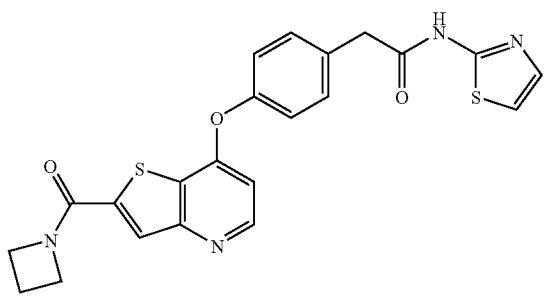

was prepared from intermediate 21b and 2-aminothiazole following Method A. $^1$H NMR (300 MHz, CD$_3$OD) δ 8.43 (d, 1H, J=5.56 Hz), 7.74 (s, 1H), 7.42 (d, 2H, J=8.59 Hz), 7.34 (d, 1H, J=5.56 Hz), 7.16 (d, 2H, J=8.59 Hz), 7.03 (d, 1H, J=3.54 Hz), 6.66 (d, 1H, J=5.31 Hz), 4.66–4.57 (m, 2H), 4.21–4.15 (m, 2H), 3.79 (s, 2H), 2.45–2.33 (m, 2H). LCMS (ESI+) [M+H]/z Calc'd 451, found 451.

Example 45

2-{4-[2-(Azetidine-1-carbonyl)-thieno[3,2-b]pyridin-7-yloxy]-phenyl}-N-cyclopropyl-acetamide

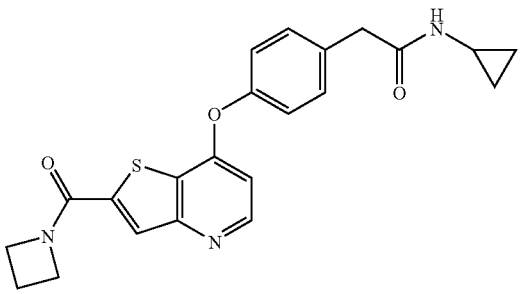

was prepared from intermediate 21b and cyclopropylamine following Method A. $^1$H NMR (300 MHz, CD$_3$OD) δ 8.42 (d, 1H, J=5.46 Hz), 7.73 (s, 1H), 7.34 (d, 2H, J=8.48 Hz), 7.12 (d, 2H, J=8.48 Hz), 6.63 (d, 1H, J=5.47 Hz), 4.66–4.57 (m, 2H), 4.21–4.15 (m, 2H), 3.43 (s, 2H), 2.64–2.56 (m, 1H), 2.45–2.33 (m, 2H), 0.68–0.62 (m, 2H), 0.45–0.39 (m, 2H). LCMS (ESI+) [M+H]/z Calc'd 408, found 408. Anal. (C$_{22}$H$_{21}$N$_3$O$_3$S.0.4CH$_2$Cl$_2$) C, H, N.

Example 46

2-{4-[2-(Azetidine-1-carbonyl)-thieno[3,2-b]pyridin-7-yloxy]-phenyl}-N-cyclobutyl-acetamide

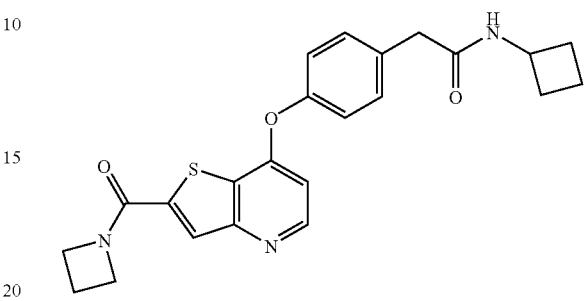

was prepared from intermediate 21b and cyclobutylamine following Method A. $^1$H NMR (300 MHz, CD$_3$OD) δ 8.42 (d, 1H, J=5.46 Hz), 7.74 (s, 1H), 7.35 (d, 2H, J=8.48 Hz), 7.12 (d, 2H, J=8.48 Hz), 6.64 (d, 1H, J=5.47 Hz), 4.66–4.57 (m, 2H), 4.21–4.15(m, 3H), 3.44 (s, 2H), 2.45–2.33 (m, 2H), 2.25–2.13 (m, 2H), 1.96–1.81 (m, 2H), 1.72–1.69 (m, 2H). LCMS (ESI+) [M+H]/z Calc'd 422, found 422.

Example 47

2-{4-[2-(Azetidine-1-carbonyl)-thieno[3,2-b]pyridin-7-yloxy]-phenyl}-N-cyclopentyl-acetamide

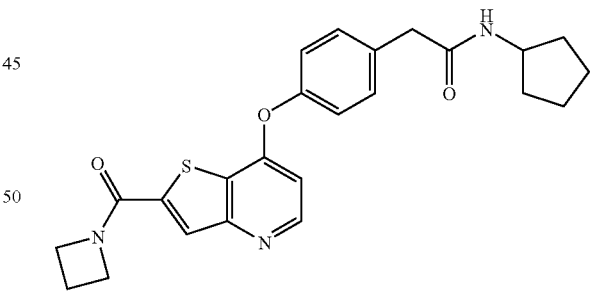

was prepared from intermediate 21b and cyclopentylamine following Method A. $^1$H NMR (300 MHz, CD$_3$OD) δ 8.43 (d, 1H, J=5.46 Hz), 7.74 (s, 1H), 7.35 (d, 2H, J=8.48 Hz), 7.13 (d, 2H, J=8.66 Hz), 6.64 (d, 1H, J=5.46 Hz), 4.66.4.57 (m, 2H), 4.21–4.15(m, 2H), 4.07–3.98 (m, 1H), 3.45 (s, 2H), 2.45–2.33 (m, 2H), 1.91–1.81 (m, 2H), 1.69–1.60 (m, 2H), 1.57–1.47 (m, 2H), 1.46–1.34 (m, 2H). LCMS (ESI+) [M+H]/z Calc'd 436, found 436.

Example 48

2-{4-[2-(Azetidine-1-carbonyl)-thieno[3,2-b]pyridin-7-yloxy]-phenyl}-N-cyclohexyl-acetamide

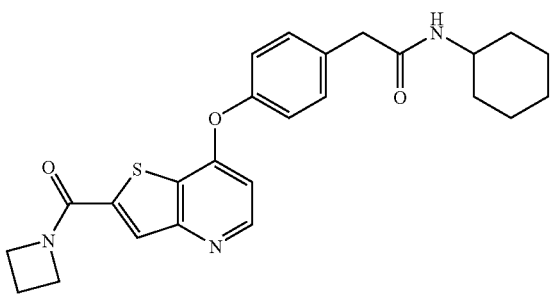

was prepared from intermediate 21b and cyclohexylamine following Method A. ¹H NMR (300 MHz, CD₃OD) δ 8.43 (d, 1H, J=5.47 Hz), 7.74 (s, 1H), 7.35 (d, 2H, J=8.48 Hz), 7.13 (d, 2H, J=8.48 Hz), 6.64 (d, 1H, J=5.47 Hz), 4.66–4.57 (m, 2H), 4.21–4.15 (m, 2H), 3.60–3.52 (m, 1H), 3.45 (s, 2H), 2.45–2.33 (m, 2H), 1.83–1.62 (m, 5H), 1.33–1.06 (m, 5H). LCMS (ESI+) [M+H]/z Calc'd 450, found 450.

Example 49

2-{4-[2-(Azetidine-1-carbonyl)-thieno[3,2-b]pyridin-7-yloxy]-2-chloro-phenyl}-N-(4,6-dimethyl-pyridin-2-yl)-acetamide

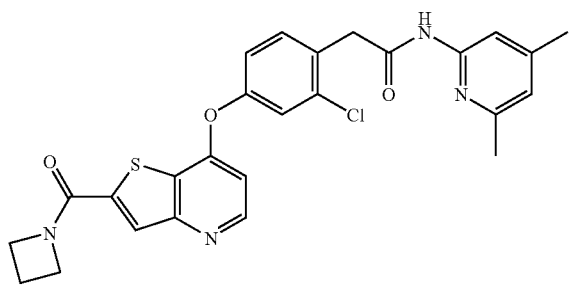

Intermediate 49a:
1-Bromomethyl-2-chloro-4-methoxy-benzene

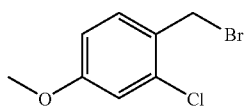

A suspension of 3-chloro-4-methylanisole (2.23 g, 14.24 mmol), N-bromosuccinimide (2.53 g, 14.24 mmol), and 70% benzoyl peroxide (493 mg, 1.424 mmol) in 40 mL CCl₄ was heated to reflux at 80° C. for two hours. The mixture was cooled to room temperature, filtered, and the filtrate was concentrated under rotary evaporator. The residue was purified by flash column chromatography eluting with 5% EtOAc in Hexane to provide 2.25 g of intermediate 49a as a white solid. ¹H NMR (300 MHz, CDCl₃) δ 7.33 (d, 1H, J=8.48 Hz), 6.93 (d, 1H, J=2.63 Hz), 6.81–6.75 (m, 1H), 4.58 (m, 2H), 3.79 (m, 3H).

Intermediate 49b:
(2-Chloro-4-methoxy-phenyl)-acetonitrile

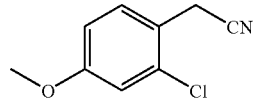

To a solution of 1-bromomethyl-2-chloro-4-methoxy-benzene (49a) (1.67 g, 7.14 mmol) in methylene chloride (15 mL) was added tetraethylammonium cyanide (1.67 g, 10.71 mmol). The mixture was stirred at room temperature for two hours, poured into water, and extracted with EtOAc for three times. The combined organic layer was dried over MgSO₄, and concentrated under rotary evaporator. The residue was purified by flash column chromatography eluting with 10% EtOAc in hexane to provide 1.13 g of intermediate 49b as a white solid. ¹H NMR (300 MHz, CDCl₃) δ 7.37 (d, 1H, J=8.48 Hz), 6.96 (d, 1H, J=2.64 Hz), 6.86–6.80 (m, 1H), 3.80 (m, 3H), 3.75 (m, 2H).

Intermediate 49c:
(2-Chloro-4-methoxy-phenyl)-acetic acid

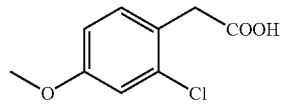

To a solution of (2-chloro-4-methoxy-phenyl)-acetonitrile (49b) (1.13 g, 6.24 mmol) in acetic acid (6 mL) and water (6 mL) was added dropwise concentrated H₂SO₄ (6 mL). The mixture was refluxed for eight hours, cooled to room temperature, poured into ice-water, adjusted pH to ~9 by aqueous NaOH solution, and washed with EtOAc. The aqueous layer was acidified with concentrated HCl aqueous solution to pH 5 and extracted with EtOAc three times, and combined organic extracts were dried over MgSO₄, concentrated in vacuo, to give 960 mg of intermediate 49c as a white solid. ¹H NMR (300 MHz, DMSO-d₆) δ 12.33 (s, 1H), 7.29 (d, 1H, J=8.48 Hz), 7.02 (d, 1H, J=2.64 Hz), 6.90–6.83 (m, 1H), 3.75 (m, 3H), 3.61 (m, 2H). LCMS (ESI-) [M-H]/z Calc'd 199, found 199.

Intermediate 49d:
(2-Chloro-4-methoxy-phenyl)-acetic acid methyl ester

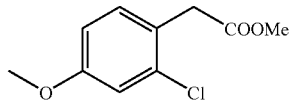

To a solution of (2-chloro-4-methoxy-phenyl)-acetic acid (49c) (0.86 g, 4.30 mmol) in 20 mL of MeOH was added 0.5 mL of 4.0 M HCl in dioxane. The mixture was stirred at room temperature overnight, concentrated, poured into water, and extracted three times with EtOAc. The combined organic layers were dried over Na$_2$SO$_4$, concentrated in vacuo, to give 870 mg of the intermediate 49d as a colorless syrup. $^1$H NMR (300 MHz, CDCl$_3$) δ 7.18 (d, 1H, J=8.67 Hz), 6.93 (d, 1H, J=2.64 Hz), 6.80–6.75 (m, 1H), 3.78 (m, 3H), 3.70 (m, 2H). LCMS (ESI+) [M+H]/z Calc'd 215, found 215.

Intermediate 49e:
(2-Chloro-4-hydroxy-phenyl)-acetic acid methyl ester

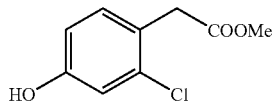

To a solution of (2-chloro-4-methoxy-phenyl)-acetic acid methyl ester (49d) (870 mg, 4.06 mmol) in 3 mL of CH$_2$Cl$_2$ was added 1.0 M BBr$_3$ (12.2 mL, 12.20 mmol), the mixture was stirred at ambient temperature overnight. The reaction was quenched with methanol, neutralized with concentrated aqueous NH$_4$OH to pH ~7. The resulting mixture was stirred at room temperature for one hour, poured into water, and extracted three times with CH$_2$Cl$_2$. The combined organic layer were dried over Na$_2$SO$_4$, concentrated in vacuo to give 740 mg of the intermediate 49e as a yellow syrup. $^1$H NMR (300 MHz, CDCl$_3$ δ 7.09 (d, 1H, J=8.48 Hz), 6.87 (d, 1H, J=2.63 Hz), 6.69–6.62 (m, 1H), 3.72 (m, 3H), 3.69 (m, 2H). LCMS (ESI+) [M+H]/z Calc'd 201, found 201.

Intermediate 49f: {4-[2-(Azetidine-1-carbonyl)-thieno[3,2-b]pyridin-7-yloxy]-2-chloro-phenyl}-acetic acid methyl ester

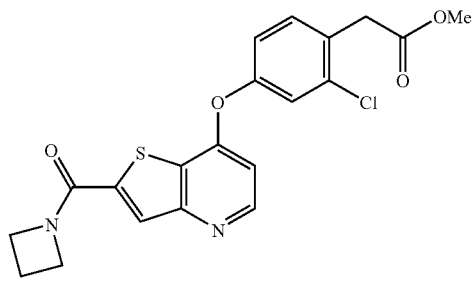

A mixture of azetidin-1-yl-(7-chloro-thieno[3,2-b]pyridin-2-yl)-methanone (21a) (930 mg, 3.70 mmol), (2-chloro-4-hydroxy-phenyl)-acetic acid methyl ester (49e) (740 mg, 3.70 mmol), and Cs$_2$CO$_3$ (1.82 g, 7.40 mmol) in 7 mL of DMSO was heated at 100° C. for overnight and cooled to room temperature. EtOAc and water were added. The organic layer was washed three times with water, dried over Na$_2$SO$_4$, and concentrated in vacuo. The residue was purified by flash column chromatography eluting with EtOAc: CHCl$_3$:MeOH (1:1:0.04) to provide 640 mg of white solid as the intermediate 49f. $^1$H NMR (300 MHz, CD$_3$OD) δ 8.47 (d, 1H, J=5.46 Hz), 7.74 (s, 1H), 7.43 (d, 1H, J=8.48 Hz), 7.32 (d, 1H, J=2.45 Hz), 7.15–7.10 (m, 1H), 6.73 (d, 1H, J=5.47 Hz), 4.67–4.54 (m, 2H), 4.24–4.13 (m, 2H), 3.80 (s, 3H), 3.65 (s, 2H), 2.48–2.33 (m, 2H). LCMS (ESI+) [M+H]/z Calc'd 417, found 417.

Intermediate 49g: {4-[2-(Azetidine-1-carbonyl)-thieno[3,2-b]pyridin-7-yloxy]-2-chloro-phenyl}-acetic acid

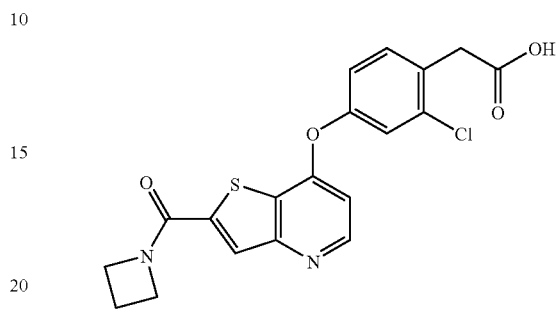

To a solution of {4-[2-(azetidine-1-carbonyl)-thieno[3,2-b]pyridin-7-yloxy]-2-chloro-phenyl}-acetic acid methyl ester (49f) (0.64 g, 1.54 mmol) in 15 mL of THF was added 8 mL of 0.33 N KOH at 0° C. The mixture was stirred at room temperature for three hours, and concentrated in vacuo. Water was added. The aqueous layer was acidified with 1 N HCl until precipitate was formed. The solid was filtered, and washed with water. The solid was dried in a vacuum-oven at 60° C. overnight. The intermediate 49g (600 mg) was obtained as a white solid. $^1$H NMR (300 MHz, CD$_3$OD) δ 8.47 (d, 1H, J=5.46 Hz), 7.74 (s, 1H), 7.43 (d, 1H, J=8.48 Hz), 7.32 (d, 1H, J=2.45 Hz), 7.15–7.10 (m, 1H), 6.73 (d, 1H, J=5.47 Hz), 4.67–4.54 (m, 2H), 4.24–4.13 (m, 2H), 3.65 (s, 2H), 2.48–2.33 (m, 2H). LCMS (ESI+) [M+H]/z Calc'd 403, found 403.

The compound of Example 49 was prepared from intermediate 49g and 2-amino-4,6-dimethyl pyridine following Method A. $^1$H NMR (300 MHz, CD$_3$OD) δ 8.47 (d, 1H, J=5.47 Hz), 7.75 (s, 1H), 7.65 (s, 1H), 7.47 (d, 2H, J=8.29 Hz), 7.33 (d, 1H, J=2.45 Hz), 7.18–7.11 (m, 1H), 6.69–6.75 (m, 1H), 4.67–4.63 (m, 2H), 4.34–4.22 (m, 2H), 3.90 (s, 2H), 2.46–2.34 (m, 2H), 2.31 (s, 3H), 2.21 (s, 3H). LCMS (ESI+) [M+H]/z Calc'd 507, found 507.

Example 50

2-{4-[2-(Azetidine-1-carbonyl)-thieno[3,2-b]pyridin-7-yloxy]-2-chloro-phenyl}-N-(5-chloro-pyridin-2-yl)-acetamide

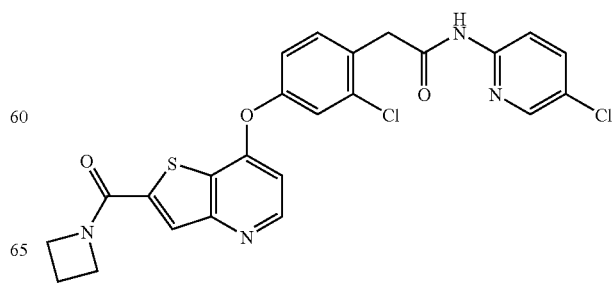

was prepared from intermediate 49g and 2-amino-5-chloro pyridine following Method A. $^1$H NMR (300 MHz, CD$_3$OD) δ 8.47 (d, 1H, J=5.66 Hz), 8.19 (d, 1H, J=2.64 Hz), 7.99 (s, 1H), 7.75 (s, 1H), 7.70–7.67 (m, 1H), 7.45 (d, 1H, J=8.29 Hz), 7.32 (d, 1H, J=2.45 Hz), 7.15–7.10 (m, 1H), 6.77–6.73 (m, 1H), 4.67–4.56 (m, 2H), 4.22–4.12 (m, 2H), 3.92 (s, 2H), 2.46–2.34(m, 2H). LCMS (ESI+) [M+H]/z Calc'd 514, found 514.

Example 51

2-{4-[2-(Azetidine-1-carbonyl)-thieno[3,2-b]pyridin-7-yloxy]-2-chloro-phenyl}-N-pyridin-2-yl-acetamide

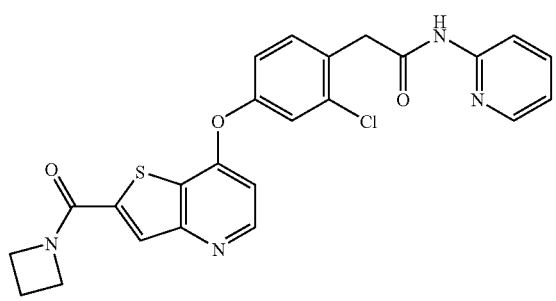

was prepared from intermediate 49g and 2-aminopyridine following Method A. $^1$H NMR (300 MHz, CD$_3$OD) δ 8.47 (d, 1H, J=5.47 Hz), 8.20 (d, 1H, J=4.34 Hz), 7.99 (d, 1H, J=4.34 Hz), 7.75 (s, 1H), 7.72–7.63 (m, 1H), 7.46 (d, 1H, J=8.48 Hz), 7.33 (d, 1H, J=2.26 Hz), 7.18–7.11 (m, 1H), 7.06–6.99 (m, 1H), 6.77 (d, 1H, J=5.46 Hz), 4.65–4.57 (m, 2H), 4.22–4.12(m, 2H), 3.93 (s, 2H), 2.46–2.34(m, 2H). LCMS (ESI+) [M+H]/z Calc'd 479, found 479. Anal. (C$_{24}$H$_{19}$N$_4$O$_3$SCl.0.5EtOAc.1.2 MeOH)C, H, N.

Example 52

2-{4-[2-(Azetidine-1-carbonyl)-thieno[3,2-b]pyridin-7-yloxy]-2-chloro-phenyl}-N-(5-methyl-isoxazol-3-yl)-acetamide

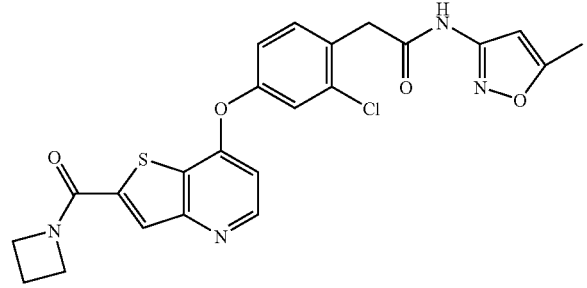

was prepared from intermediate 49g and 3-amino-5-methyl isoxazole following Method A. $^1$H NMR (300 MHz, CD$_3$OD) δ 8.46 (d, 1H, J=4.90 Hz), 7.74 (s, 1H), 7.43 (d, 1H, J=8.29 Hz), 7.31 (d, 1H, J=2.45 Hz), 7.15 (d, 1H, J=6.79 Hz), 6.75 (d, 1H, J=5.27 Hz), 6.49 (s, 1H), 4.67–4.56 (m, 2H), 4.22–4.12 (m, 2H), 3.86 (s, 2H), 2.46–2.34 (m, 2H), 2.29 (s, 3H). LCMS (ESI+) [M+H]/z Calc'd 483, found 483. Anal. (C$_{23}$H$_{19}$N$_4$O$_4$SCl.0.6 CH$_3$COOH.1.5 H$_2$O)C, H, N.

Example 53

2-{4-[2-(Azetidine-1-carbonyl)-thieno[3,2-b]pyridin-7-yloxy]-2-chloro-phenyl}-N-(3-methyl-isoxazol-5-yl)-acetamide

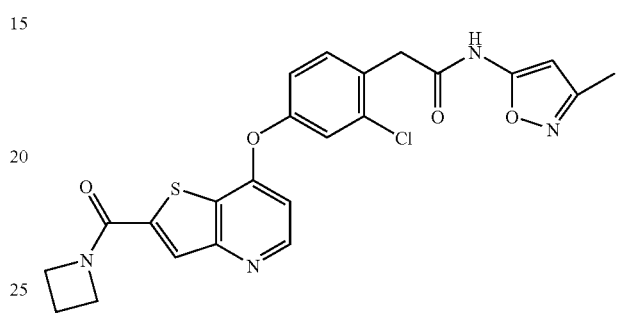

was prepared from intermediate 49g and 5-amino-3-methyl isoxazole following Method A. $^1$H NMR (300 MHz, CD$_3$OD) δ 8.46 (d, 1H, J=5.28 Hz), 7.74 (s, 1H), 7.43 (d, 1H, J=8.29 Hz), 7.31 (d, 1H, J=2.45 Hz), 7.15–7.10 (m, 1H), 6.75 (d, 1H, J=5.36 Hz), 6.49 (s, 1H), 4.67–4.56 (m, 2H), 4.22–4.12 (m, 2H), 3.87 (s, 2H), 2.46–2.34 (m, 2H), 2.13 (s, 3H). LCMS (ESI+) [M+H]/z Calc'd 483, found 483.

Example 54

2-{4-[2-(Azetidine-1-carbonyl)-thieno[3,2-b]pyridin-7-yloxy]-2-chloro-phenyl}-N-(4-methyl-oxazol-2-yl)-acetamide

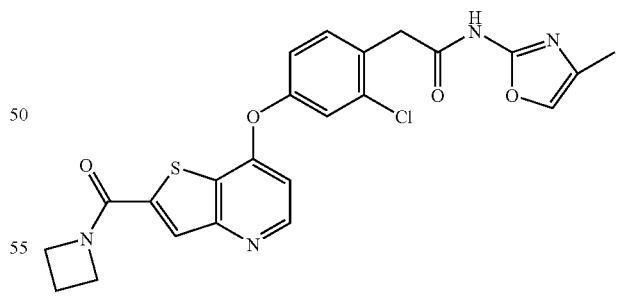

was prepared from intermediate 49g and 2-amino-4-methyl-oxazole following Method A. $^1$H NMR (300 MHz, CD$_3$OD) 38.47 (d, 1H, J=5.47 Hz), 7.77 (s, 1H), 7.40 (d, 1H, J=9.23 Hz), 7.33 (d, 1H, J=2.45 Hz), 7.29 (s, 1H), 7.18–7.09 (m, 1H), 6.77 (d, 1H, J=5.09 Hz), 4.67–4.56 (m, 2H), 4.22–4.12 (m, 2H), 3.83 (s, 2H), 2.46–2.34 (m, 2H), 1.97 (s, 3H). LCMS (ESI+) [M+H]/z Calc'd 483, found 483.

Example 55

2-{4-[2-(Azetidine-1-carbonyl)-thieno[3,2-b]pyridin-7-yloxy]-2-chloro-phenyl}-N-(5-methyl-1H-pyrazol-3-yl)-acetamide

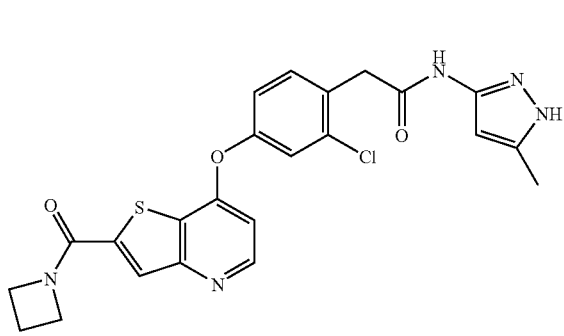

was prepared from intermediate 49g and 3-amino-5-methyl pyrazole following Method A. $^1$H NMR (300 MHz, CD$_3$OD) δ 8.48 (d, 1H, J=5.27 Hz), 7.77 (s, 1H), 7.47 (d, 1H, J=8.67 Hz), 7.32 (s, 1H), 7.14 (d, 1H, J=9.42 Hz), 6.77 (d, 1H, J=5.27 Hz), 6.22 (s, 1H), 4.67–4.56 (m, 2H), 4.22–4.12 m, 2H), 3.85 (s, 2H), 2.46–2.34 (m, 2H), 2.18 (s, 3H). LCMS (ESI+) [M+H]/z Calc'd 482, found 482. Anal. (C$_{23}$H$_{20}$N$_5$O$_3$SCl.1.7H$_2$O)C, H, N.

Example 56

2-{4-[2-(Azetidine-1-carbonyl)-thieno[3,2-b]pyridin-7-yloxy]-2-chloro-phenyl}-N-(1,5-dimethyl-1H-pyrazol-3-yl)-acetamide

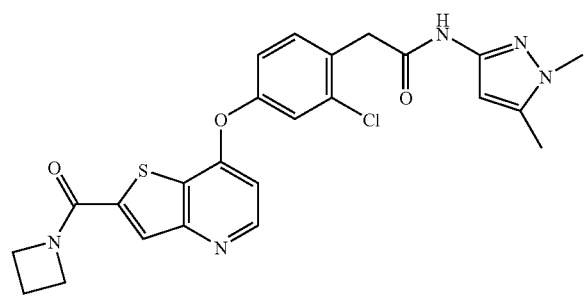

was prepared from intermediate 49g and 3-amino-1,5-dimethylpyrazole following Method A. $^1$H NMR (300 MHz, CD$_3$OD) δ 8.48 (d, 1H, J=5.47 Hz), 7.76 (s, 1H), 7.48 (d, 1H, J=8.29 Hz), 7.34 (d, 1H, J=2.45 Hz), 7.18–7.12 (m, 1H), 6.66 (d, 1H, J=5.46 Hz), 5.97 (s, 1H), 4.67–4.56 (m, 2H), 4.22–4.12 (m, 2H), 3.90 (s, 2H), 3.59 (s, 3H), 2.46–2.34 (m, 2H), 2.10 (s, 3H). LCMS (ESI+) [M+H]/z Calc'd 496, found 496. Anal. (C$_{24}$H$_{22}$N$_5$O$_3$SCl.0.1CH$_2$Cl$_2$.1.0EtOAc) C, H, N.

Example 57

2-{4-[2-(Azetidine-1-carbonyl)-thieno[3,2-b]pyridin-7-yloxy]-2-chloro-phenyl}-N-(3-morpholin-4-yl-propyl)-acetamide

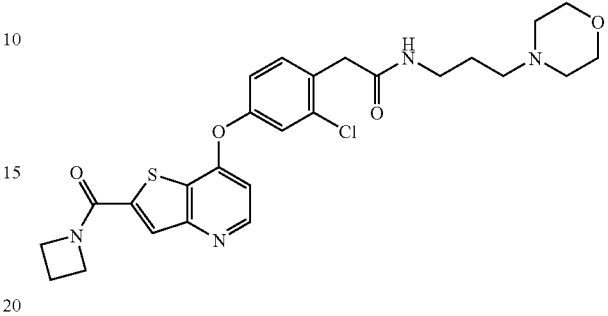

was prepared from intermediate 49g and 3-morpholin-4-yl-propylamine following Method A. $^1$H NMR (300 MHz, CD$_3$OD) δ 8.48 (d, 1H, J=5.47 Hz), 7.76 (s, 1H), 7.43 (d, 1H, J=8.48 Hz), 7.31 (d, 1H, J=2.48 Hz), 7.16–7.10 (m, 1H), 6.76 (d, 1H, J=5.46 Hz), 4.67–4.56 (m, 2H), 4.22–4.12 (m, 2H), 3.66–3.59 (m, 6H), 3.24–3.18 (m, 2H), 2.46–2.34(m, 8H), 1.72–1.63 (m, 2H). LCMS (ESI+) [M+H]/z Calc'd 529, found 529. Anal. (C$_{26}$H$_{29}$N$_4$O$_4$SCl.0.8CH$_3$COOH) C, H, N.

Example 58

2-{2-Chloro-4-[2-(1-methyl-1H-imidazol-2-yl)-thieno[3,2-b]pyridin-7-yloxy]-phenyl}-N-(5-methyl-furan-2-ylmethyl)-acetamide

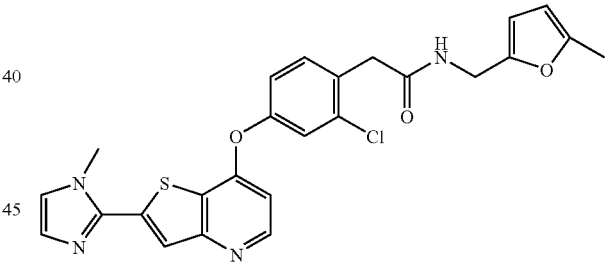

Intermediate 58a: {2-Chloro-4-[2-(1-methyl-1H-imidazol-2-yl)-thieno[3,2-b]pyridin-7-yloxy]-phenyl}-acetic acid

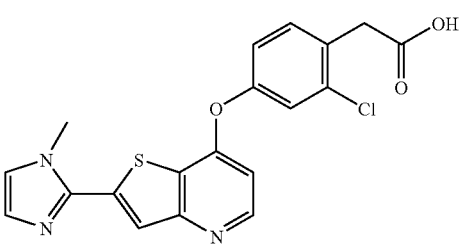

was prepared from hydrolysis of its corresponding methyl ester following the procedure described for the preparation of intermediate 49g. The corresponding methyl ester was prepared from coupling of 7-chloro-2-(1-methyl-1H-imidazol-2-yl)-thieno[3,2-b]pyridine and 49e following Method C. $^1$H NMR (300 MHz, CD$_3$OD) δ 8.42 (d, 1H, J=5.66 Hz), 7.72 (s, 1H), 7.42 (d, 1H, J=8.48 Hz), 7.29 (d, 1H, J=2.45 Hz), 7.23 (s, 1H), 7.14–7.08 (m, 1H), 7.10 (s, 1H), 6.70 (d, 1H, J=5.46 Hz), 3.93 (s, 3H), 3.74 (s, 2H). LCMS (ESI+) [M+H]/z Calc'd 400, found 400.

The compound of Example 58 was prepared from intermediate 58a and C-(5-methyl-furan-2-yl)-methylamine following Method A. $^1$H NMR (300 MHz, CD$_3$OD) δ 8.37 (d, 1H, J=5.66 Hz), 7.66 (s, 1H), 7.36 (d, 1H, J=8.29 Hz), 7.25 (d, 1H, J=2.26 Hz), 7.19 (s, 1H), 7.10–7.03 (m, 1H), 6.98 (d, 1H, J=1.32 Hz), 6.65(d, 1H, J=5.46 Hz), 6.00(d, 1H, J=3.02 Hz), 5.80–5.78 (m, 1H), 4.22 (s, 2H), 3.90 (s, 3H), 3.64 (s, 2H), 2.12(s, 3H). LCMS (ESI+) [M+H]/z Calc'd 493, found 493. Anal. (C$_{25}$H$_{21}$N$_4$O$_3$SCl.0.2CH$_2$Cl$_2$), C, H, N.

Example 59

2-{2-Chloro-4-[2-(1-methyl-1H-imidazol-2-yl)-thieno[3,2-b]pyridin-7-yloxy]-phenyl}-N-(3-fluoro-benzyl)-acetamide

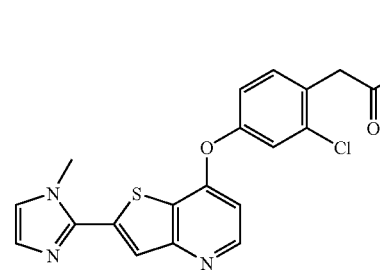

was prepared from intermediate 58a and 3-fluoro-benzylamine following Method A. $^1$H NMR (300 MHz, CD$_3$OD) δ 8.40 (d, 1H, J=5.46 Hz), 7.70 (s, 1H), 7.41 (d, 1H, J=8.47 Hz), 7.28 (d, 1H, J=2.45 Hz), 7.23–7.19 (m, 2H), 7.13–7.07 (m, 1H), 6.99 (d, 1H, J=1.14 Hz), 6.69(d, 1H, J=5.65 Hz), 7.04–6.85 (m, 2H), 6.69(d, 1H, J=5.65 Hz), 4.32 (s, 2H), 3.92 (s, 3H), 3.70 (s, 2H). LCMS (ESI+) [M+H]/z Calc'd 507, found 507. Anal. (C$_{26}$H$_{20}$N$_4$O$_2$SCl F.0.1CH$_2$Cl$_2$), C, H, N.

Example 60

2-{2-Chloro-4-[2-(1-methyl-1H-imidazol-2-yl)-thieno[3,2-b]pyridin-7-yloxy]-phenyl}-N-pyridin-2-yl-acetamide

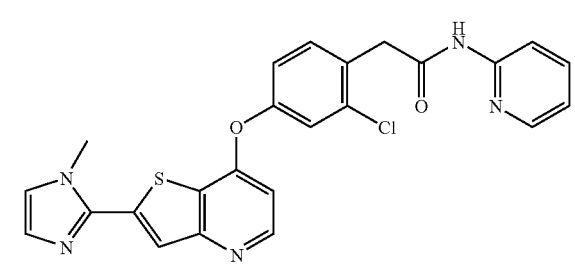

was prepared from intermediate 58a and 2-aminopyridine following Method A. $^1$H NMR (300 MHz, CD$_3$OD) δ 8.41 (d, 1H, J=5.65 Hz), 8.22–8.18 (m, 1H), 7.98 (d, 1H, J=8.48 Hz), 7.70–7.63 (m, 2H), 7.46 (d, 1H, J=8.48 Hz), 7.31 (d, 1H, J=2.45 Hz), 7.22 (s, 1H), 7.16–7.10 (m, 1H), 7.05–6.98 (m, 2H), 6.71 (d, 1H, J=5.46 Hz), 3.92 (s, 5H). LCMS (ESI+) [M+H]/z Calc'd 476, found 476. Anal. (C$_{24}$H$_{18}$N$_5$O$_2$SCl.0.5CH$_2$Cl$_2$.0.6EtOAc), C, H, N.

Example 61

2-{2-Chloro-4-[2-((R)-3-hydroxy-pyrrolidine-1-carbonyl)-thieno[3,2-b]pyridin-7-yloxy]-phenyl}-N-pyridin-2-yl-acetamide

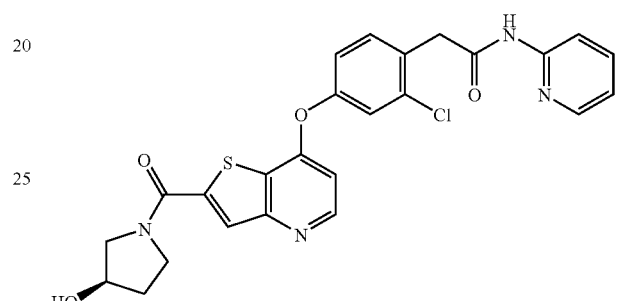

Intermediate 61a: 2-(2-Chloro-4-hydroxy-phenyl)-N-pyridin-2-yl-acetamide

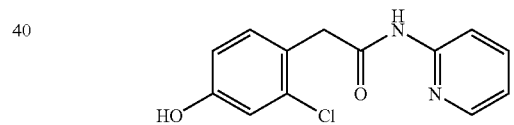

was prepared from (1) coupling of intermediate 49c with 2-aminopyridine following Method A, and (2) converting the resulting methyl ether to the corresponding phenol following Method D. $^1$H NMR (300 MHz, CD$_3$OD) δ 8.16 (d, 1H, J=5.09 Hz), 7.97 (d, 1H, J=8.47 Hz), 7.69–7.60 (m, 1H), 7.10 (d, 1H, J=8.48 Hz), 7.04–6.97 (m, 1H), 6.76 (d, 1H, J=2.25 Hz), 6.66–6.60 (m, 1H), 3.72 (s, 2H). LCMS (ESI+) [M+H]/z Calc'd 263, found 263.

The compound of Example 61 was prepared from coupling of (7-chloro-thieno[3,2-b]pyridin-2-yl)-(3-hydroxy-pyrrolidin-1-yl)-methanone (2b) with intermediate 61a following Method C. $^1$H NMR (300 MHz, CD$_3$OD) δ 8.46 (d, 1H, J=5.46 Hz), 8.20 (d, 1H, J=5.46 Hz), 7.98 (d, 1H, J=8.47 Hz), 7.85 (d, 1H, J=17.33 Hz), 7.70–7.60 (m, 1H), 7.40 (d, 1H, J=8.48 Hz), 7.31 (d, 1H, J=2.45 Hz), 7.16–7.10 (m, 1H), 7.04–6.98 (m, 1H), 6.76 (d, 1H, J=5.46 Hz), 4.41 (bs, 1H), 4.03–3.96 (m, 4H), 3.75–3.57(m, 3H), 2.13–1.94(m, 2H). LCMS (ESI+) [M+Na]/z Calc'd 510, found 510. Anal. (C$_{25}$H$_{21}$N$_4$O$_4$SCl.0.5CH$_2$Cl$_2$), C, H, N.

Example 62

2-{2-Chloro-4-[2-((R)-3-methoxy-pyrrolidine-1-carbonyl)-thieno[3,2-b]pyridin-7-yloxy]-phenyl}-N-pyridin-2-yl-acetamide

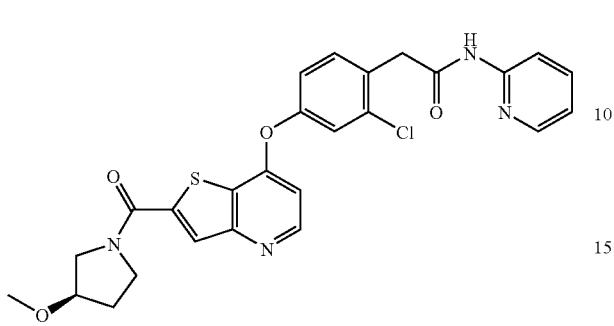

Intermediate 62a (7-Chloro-thieno[3,2-b]pyridin-2-yl)-(3-methoxy-pyrrolidin-1-yl)-methanone

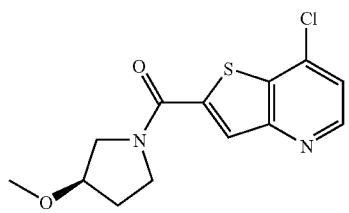

was prepared from 7-chloro-thieno[3,2-b]pyridine-2-carboxylic acid and 3R-methoxy-pyrrolidine following Method A. $^1$H NMR (300 MHz, CDCl$_3$) δ 8.68 (d, 1H, J=5.5 Hz), 7.85 (d, 1H, J=14.3 Hz), 7.40 (d, 1H, J=5.5 Hz), 4.18–4.07 (m, 1H), 4.03–3.73 (m, 4H), 3.20 (d, 3H, J=14.5 Hz), 2.36–2.03 (m, 2H). LCMS ESI (M+H$^+$): 297.05.

The compound of Example 62 was prepared from coupling of (7-chloro-thieno[3,2-b]pyridin-2-yl)-(3-methoxy-pyrrolidin-1-yl)-methanone (62a) with intermediate 61a following Method C. $^1$H NMR (300 MHz, CD$_3$OD) δ 8.46 (d, 1H, J=5.46 Hz), 8.20 (d, 1H, J=6.03 Hz), 7.98 (d, 1H, J=8.10 Hz), 7.84 (d, 1H, J=6.31 Hz), 7.71–7.62 (m, 1H), 7.46 (d, 1H, J=8.48 Hz), 7.31 (d, 1H, J=2.44 Hz), 7.16–7.10 (m, 1H), 7.04–6.98 (m, 1H), 6.66 (d, 1H, J=5.46 Hz), 4.08–3.96 (m, 3H), 3.92 (s, 3H), 3.79 (s, 2H), 3.71–3.57(m, 2H), 2.43–2.33 (m, 2H). LCMS (ESI+) [M+H]/z Calc'd 524, found 524. Anal. (C$_{26}$H$_{23}$N$_4$O$_4$SCl.0.5CH$_2$Cl$_2$.1.5EtOAc), C, H, N.

Example 63

2-{4-[2-(Azetidine-1-carbonyl)-thieno[3,2-b]pyridin-7-yloxy]-2-chloro-phenyl}-N-methyl-acetamide

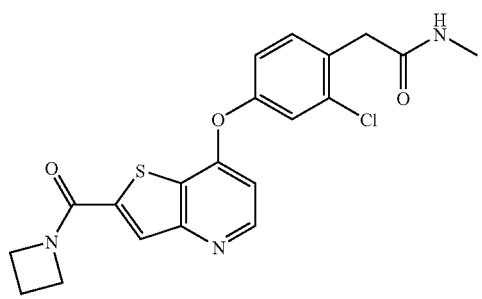

Intermediate 2-(2-Chloro-4-hydroxy-phenyl)-N-methyl-acetamide (63a)

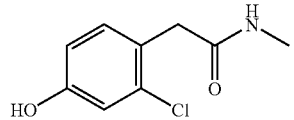

was prepared from (1) coupling of intermediate 49c with methylamine following Method A, and (2) converting methyl ether to the corresponding phenol following Method D. $^1$H NMR (300 MHz, CD$_3$OD) δ 7.02 (d, 1H, J=8.29 Hz), 6.71 (d, 1H, J=2.45 Hz), 6.61–6.56 (m, 1H), 3.43 (s, 2H), 2.61 (s, 3H). LCMS (ESI+) [M+H]/z Calc'd 200, found 200.

The compound of Example 63 was prepared from coupling of azetidin-1-yl-(7-chloro-thieno[3,2-b]pyridin-2-yl)-methanone (21a) and intermediate 63a following Method C. $^1$H NMR (300 MHz, CD$_3$OD) δ 8.47 (d, 1H, J=5.46 Hz), 7.76 (s, 1H), 7.42 (d, 1H, J=8.48 Hz), 7.30 (d, 1H, J=2.45 Hz), 7.15–7.09 (m, 1H), 6.76 (d, 1H, J=5.46 Hz), 4.674.57 (m, 2H), 4.23–4.13(m, 2H), 3.65 (s, 2H), 2.68 (s, 3H), 2.45–2.33 (m, 2H). LCMS (ESI+) [M+H]/z Calc'd 416, found 416. Anal. (C$_{20}$H$_{18}$N$_3$O$_3$SCl.0.3CH$_2$Cl$_2$) C, H, N.

Example 64

2-{2-Chloro-4-[2-((R)-3-hydroxy-pyrrolidine-1-carbonyl)-thieno[3,2-b]pyridin-7-yloxy]-phenyl}-N-methyl-acetamide

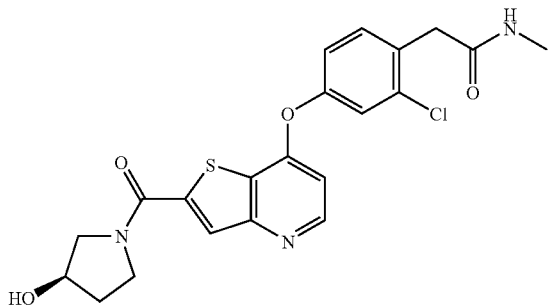

was prepared from coupling of (7-chloro-thieno[3,2-b]pyridin-2-yl)-(3-hydroxy-pyrrolidin-1-yl)-methanone (2b) with intermediate 63a following Method C. $^1$H NMR (300 MHz, CD$_3$OD) δ 8.45 (d, 1H, J=5.47 Hz), 7.84 (d, 1H, J=17.33 Hz), 7.40 (d, 1H, J=8.48 Hz), 7.29 (d, 1H, J=2.26 Hz), 7.13–7.08 (m, 1H), 6.74 (d, 1H, J=5.46 Hz), 4.42 (bs, 1H), 4.03–3.90 (m, 2H), 3.74–3.58(m, 5H), 2.66 (s, 3H), 2.10–1.97(m, 2H). LCMS (ESI+) [M+H]/z Calc'd 446, found 446. Anal. (C$_{21}$H$_{20}$N$_3$O$_4$SCl.0.7CH$_2$Cl$_2$), C, H, N.

Example 65

2-{2-Chloro-4-[2-(1-methyl-1H-imidazol-2-yl)-thieno[3,2-b]pyridin-7-yloxy]-phenyl}-N-methyl-acetamide

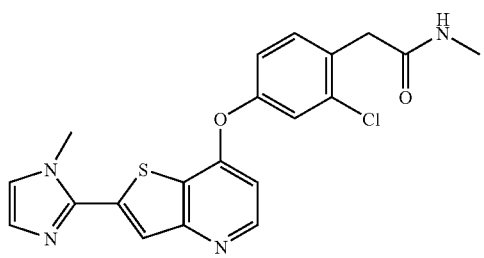

was prepared from coupling of 7-chloro-2-(1-methyl-1H-imidazol-2-yl)-thieno[3,2-b]pyridine and intermediate 63a following Method C. $^1$H NMR (300 MHz, CD$_3$OD) δ 8.38 (d, 1H, J=5.65 Hz), 7.67 (s, 1H), 7.38 (d, 1H, J=8.48 Hz), 7.27 (d, 1H, J=2.44 Hz), 7.20 (s, 1H), 7.12–7.06 (m, 1H), 6.99 (s, 1H), 6.67 (d, 1H, J=5.47 Hz), 3.91 (s, 3H), 3.61(s, 2H), 2.66 (s, 3H). LCMS (ESI+) [M+H]/z Calc'd 413, found 413. Anal. (C$_{20}$H$_{17}$N$_4$O$_2$SCl.0.25CH$_2$Cl$_2$), C, H, N.

Example 66

2-{4-[2-((R)-3-Hydroxy-pyrrolidine-1-carbonyl)-thieno[3,2-b]pyridin-7-yloxy]-phenyl}-N-methyl-acrylamide

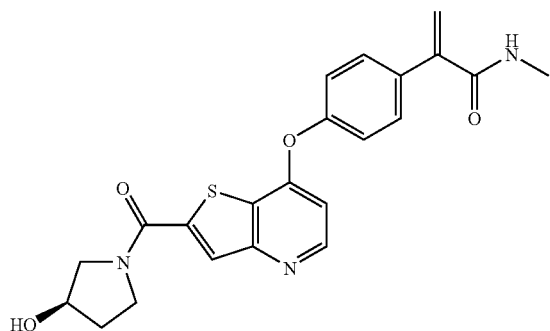

Intermediate 66a: 2-(4-Methoxy-phenyl)-acrylic acid ethyl ester

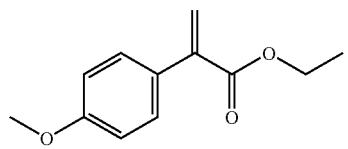

A mixture of ethyl-4-methoxyphenethyl acetate (3.0 g, 15.44 mmol), 95% parafomaldehyde (732 mg, 23.16 mmol), K$_2$CO$_3$ (3.30 g, 23.88 mmol), and Bu$_4$NI (171 mg, 0.463 mmol) in toluene was heated at 80° C. for two hours, cooled to room temperature, poured into water, and extracted with EtOAc for three times. The combined organic phase was dried over Na$_2$SO$_4$, concentrated in vacuo, and purified by flash column chromatography eluting with 10% EtOAc in hexanes to provide 2.14 g of intermediate 66a as a colorless oil. $^1$H NMR (300 MHz, CD$_3$OD) δ 7.36 (d, 2H, J=8.67 Hz), 6.87 (d, 2H, J=8.67 Hz), 6.64 (s, 1H), 5.81 (s, 1H), 4.28 (q, 2H, J=7.16 Hz), 3.81 (s, 3H), 1.32 (t, 2H, J=7.16 Hz). LCMS (ESI+) [M+H]/z Calc'd 207, found 207.

Intermediate 66b: 2-(4-Methoxy-phenyl)-N-methyl-acrylamide

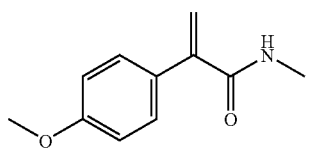

To a solution of 2-(4-methoxy-phenyl)-acrylic acid ethyl ester (66a) (1.0 g, 4.85 mmol) in 15 mL of THF was added dropwise 0.33 N KOH (33.5 mL) at 0° C. The mixture was stirred at ambient temperature for three hours, concentrated in vacuo, re-suspended in water, and extracted with EtOAc three times. The combined organic layer was dried over Na$_2$SO$_4$, and concentrated to give 0.86 g acid as a white solid. It was dissolved in 8 mL of DMF, and to this solution was added 2.0 M methylamine (9.7 mL, 19.40 mmol) and Et$_3$N (2.70 mL, 19.40 mmol), follow by HATU (2.75 g, 7.23 mmol). The resulting mixture was stirred at room temperature for 30 minutes. Sat. NaHCO$_3$ was added, the mixture was extracted with EtOAc. The organic phase was dried over Na$_2$SO$_4$, concentrated, and purified by flash column chromatography eluting with EtOAc:CH$_2$Cl$_2$:MeOH (1:1:0.01) to provide 0.68 g off-white solid as the intermediate 66b. $^1$H NMR (300 MHz, CD$_3$OD) δ 7.23 (d, 2H, J=8.86 Hz), 6.81 (d, 2H, J=8.85 Hz), 5.52 (s, 2H), 3.81 (s, 3H), 2.72 (d, 3H, J=3.77 Hz). LCMS (ESI+) [M+H]/z Calc'd 192, found 192.

Intermediate 66c: 2-(4-Hydroxy-phenyl)-N-methyl-acrylamide

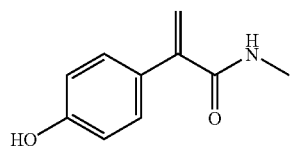

To a solution of 2-(4-methoxy-phenyl)-N-methyl-acrylamide (66b) (0.68 g, 3.56 mmol) in 40 mL of CH$_2$Cl$_2$ was added 1.0 M BBr$_3$ (7.1 mL, 7.10 mmol) at 0° C. The mixture was stirred at 0° C. to room temperature for two hours. The reaction was quenched with MeOH, neutralized with concentrated aqueous NH$_4$OH to pH ~7. The resulting mixture was stirred at room temperature for one hour. Water was added, and the mixture was extracted with CH$_2$Cl$_2$ three times. The combined organic layer was dried over Na$_2$SO$_4$, concentrated, and purified by flash column chromatography eluting with EtOAc:CH$_2$Cl$_2$:MeOH (1:1:0.02) to provide 0.38 g orange solid as the intermediate 66c. $^1$H NMR (300 MHz, CD$_3$OD) δ 7.17 (d, 2H, J=8.67 Hz), 6.67 (d, 2H, J=8.85 Hz), 5.48 (d, 2H, J=1.89 Hz), 2.72 (s, 3H). LCMS (ESI+) [M+H]/z Calc'd 178, found 178.

The compound of Example 66 was prepared from coupling of (7-chloro-thieno[3,2-b]pyridin-2-yl)-(3-hydroxy-pyrrolidin-1-yl)-methanone (2b) and intermediate 66c following Method C. ¹H NMR (300 MHz, CD₃OD) δ 8.42 (d, 1H, J=5.46 Hz), 7.83 (d, 1H, J=16.96 Hz), 7.46 (d, 2H, J=8.66 Hz), 7.16 (d, 2H, J=8.86 Hz), 6.67 (d, 1H, J=5.46 Hz), 5.70 (d, 2H, J=8.86 Hz), 4.42 (bs, 1H), 3.98–3.88 (m, 2H), 3.71–3.57(m, 3H), 2.75 (s, 3H), 2.13–1.93 (m, 2H). LCMS (ESI+) [M+H]/z Calc'd 424, found 424. Anal. (C₂₂H₂₁N₃O₄S.0.6CH₂Cl₂) C, H, N.

Example 67

1-{4-[2-((R)-3-Hydroxy-pyrrolidine-1-carbonyl)-thieno[3,2-b]pyridin-7-yloxy]-phenyl}-cyclopropanecarboxylic acid methylamide

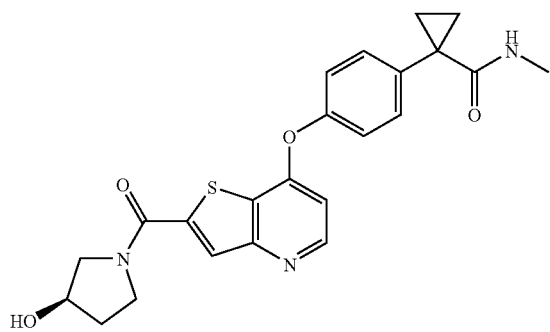

Intermediate 67a:
1-(4-Methoxy-phenyl)-cyclopropanecarboxylic acid methylamide

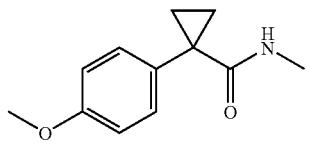

1-(4-Methoxyphenyl)-cyclopropane carboxyl acid (1.0 g, 5.20 mmol) was dissolved in 6 mL of DMF, to this solution was added 2.0 M methylamine (10.4 mL, 20.80 mmol) and Et₃N (3.0 mL, 20.80 mmol), followed by HATU (3.00 g, 7.89 mmol). The resulting mixture was stirred at room temperature for 30 min. Saturated aqueous NaHCO₃ solution was added, and the mixture was extracted with EtOAc for three times. The combined organic phase was dried over Na₂SO₄, concentrated, and purified by flash column chromatography eluting with EtOAc:CH₂Cl₂:MeOH (1:1:0.02) to provide 0.78 g off-white solid as the intermediate 67a. ¹H NMR (300 MHz, CDCl₃) δ 7.32 (d, 2H, J=8.85 Hz), 6.88 (d, 2H, J=8.66 Hz), 5.38 (bs, 1H), 3.82 (s, 3H), 2.70 (d, 3H, J=4.71 Hz), 1.59–1.54 (m, 2H), 1.00–0.97 (m, 2H). LCMS (ESI+) [M+H]/z Calc'd 206, found 206.

Intermediate 67b:
1-(4-Hydroxy-phenyl)-cyclopropanecarboxylic acid methylamide

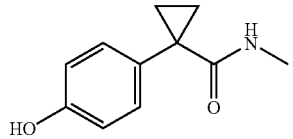

was prepared from intermediate 67a following Method D. ¹H NMR (300 MHz, DMSO-d₆) δ 9.41 (s, 1H), 7.12 (d, 2H, J=8.47 Hz), 6.71 (d, 2H, J=8.47 Hz), 6.47 (s, 1H), 2.49 (s, 3H), 1.28–1.22 (m, 2H), 0.87–0.80 (m, 2H). LCMS (ESI+) [M+H]/z Calc'd 192, found 192.

The compound of Example 67 was prepared from coupling of (7-chloro-thieno[3,2-b]pyridin-2-yl)-(3-hydroxy-pyrrolidin-1-yl)-methanone (2b) and intermediate 67b following Method C. ¹H NMR (300 MHz, CD₃OD) δ 8.41 (d, 1H, J=5.28 Hz), 7.82 (d, 1H, J=17.52 Hz), 7.43 (d, 2H, J=8.47 Hz), 7.15 (d, 2H, J=8.47 Hz), 6.76 (d, 1H, J=5.46 Hz), 4.42 (bs, 1H), 4.01–3.88 (m, 2H), 3.76–3.57(m, 3H), 2.59 (s, 3H), 2.13–1.93 (m, 2H), 1.46–1.39 (m, 2H), 1.02–0.96 (m, 2H). LCMS (ESI+) [M+H]/z Calc'd 438, found 438. Anal. (C₂₃H₂₃N₃O₄S.0.3CH₂Cl₂) C, H, N.

Example 68

2-{4-[2-((S)-3-Methoxy-pyrrolidine-1-carbonyl)-thieno[3,2-b]pyridin-7-yloxy]-phenyl}-N-methyl-acetamide

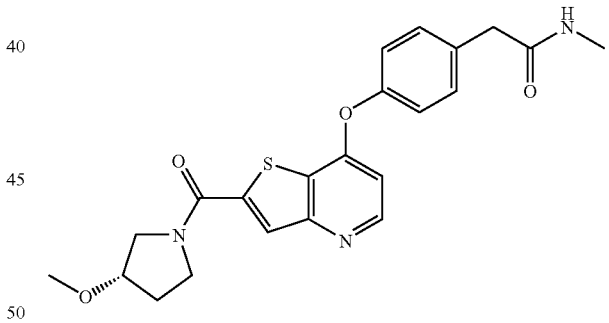

Intermediate 68a:
2-(4-Methoxy-phenyl)-N-methyl-acetamide

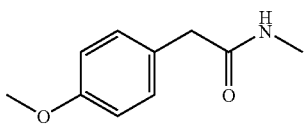

was prepared from 4-methoxyphenylacetic acid chloride and methylamine following Method B. ¹H NMR (300 MHz, CDCl₃) δ 7.14 (d, 2H, J=8.67 Hz), 6.86 (d, 2H, J=8.67 Hz), 3.78 (s, 3H), 3.49 (s, 2H), 2.72 (d, 3H, J=4.71 Hz). LCMS (ESI+) [M+H]/z Calc'd 180, found 180.

Intermediate 68b:
2-(4-Hydroxy-phenyl)-N-methyl-acetamide

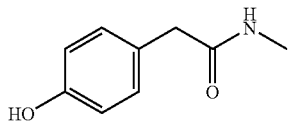

was prepared from intermediate 68a following Method D. ¹H NMR (300 MHz, CD₃OD) δ 6.97 (d, 2H, J=8.48 Hz), 6.61 (d, 2H, J=8.67 Hz), 3.27 (s, 2H), 2.59 (d, 3H, J=4.52 Hz). LCMS (ESI+) [M+H]/z Calc'd 166, found 166.

Intermediate 68c: (7-chloro-thien[3,2-b]pyridin-2-yl)-(3-(S)-methoxy-pyrrolidin-1-yl)-methanone

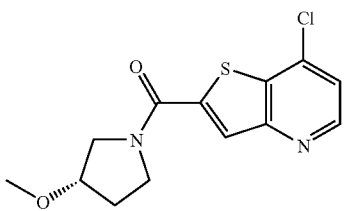

was prepared from 7-chloro-thieno[3,2-b]pyridine-2-carboxylic acid and 3S-methoxy-pyrrolidine following Method A. ¹H NMR (300 MHz, CDCl₃, δ 8.68 (d, 1H, J=5.5 Hz), 7.85 (d, 1H, J=14.3 Hz, 7.40 (d, 1H, J=5.5 Hz), 4.18–4.07 (m, 1H), 4.03–3.73 (m, 4H), 3.2 (d, 3H, J=14.5 Hz), 2.36–2.03 (m, 2H). LCMS ESI (M+H+): 297.05

The compound of Example 68 was prepared from (7-chloro-thieno[3,2-b]pyridin-2-yl)-(3(S)-methoxy-pyrrolidin-1-yl)-methanone (68c) and intermediate 68b following Method C. ¹H NMR (300 MHz, CD₃OD) δ 8.39 (d, 1H, J=5.46 Hz), 7.80 (d, 1H, J=4.53 Hz), 7.34 (d, 2H, J=8.48 Hz), 7.10 (d, 2H, J=8.67 Hz), 6.60 (d, 1H, J=5.47 Hz), 4.05–3.80 (m, 3H), 3.70–3.58 (m, 2H), 3.46 (s, 2H), 3.29 (s, 3H), 2.65 (s, 3H), 2.11–1.95 (m, 2H). LCMS (ESI+) [M+H]/z Calc'd 426, found 426. Anal. (C₂₂H₂₃N₃O₄S. 0.2CH₂Cl₂) C, H, N.

Example 69

2-{4-[2-((R)-3-Hydroxy-pyrrolidine-1-carbonyl)-thieno[3,2-b]pyridin-7-yloxy]-phenyl}-N-methyl-acetamide

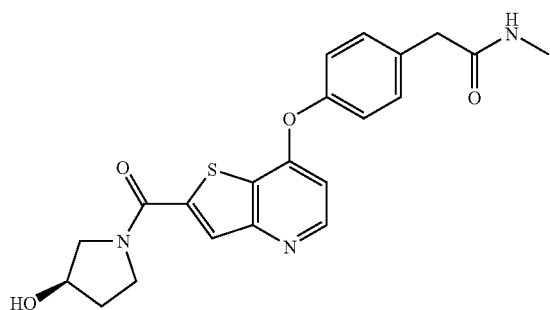

was prepared from (7-chloro-thieno[3,2-b]pyridin-2-yl)-(3-hydroxy-pyrrolidin-1-yl)-methanone (2b) and intermediate 68b following Method C. ¹H NMR (300 MHz, CD₃OD) δ 8.39 (d, 1H, J=5.65 Hz), 7.81 (d, 1H, J=17.14 Hz), 7.43 (d, 2H, J=8.48 Hz), 7.10 (d, 2H, J=8.67 Hz), 6.61 (d, 1H, J=5.46 Hz), 4.42 (bs, 1H), 4.01–3.88 (m, 2H), 3.76–3.57(m, 3H), 3.45 (s, 2H), 2.64 (s, 3H), 2.09–1.98 (m, 2H). LCMS (ESI+) [M+H]/z Calc'd 412, found 412. Anal. (C₂₁H₂₁N₃O₄S. 0.4CH₂Cl₂) C, H, N.

Example 70

2-{2-Chloro-4-[2-((R)-3-hydroxy-pyrrolidine-1-carbonyl)-thieno[3,2-b]pyridin-7-yloxy]-phenyl}-2-methoxy-N-methyl-acetamide

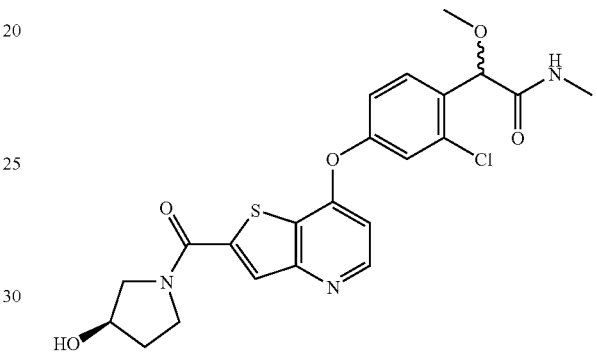

Intermediate 70a:
2-(2-Chloro-4-methoxy-phenyl)-N-methyl-acetamide

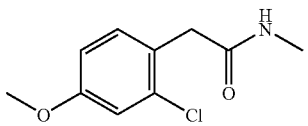

To a suspension of (2-chloro-4-methoxy-phenyl)-acetic acid (49c) (500 mg, 2.50 mmol) in CH₂Cl₂ (10 mL) was added 2.0 M oxalyl chloride in CH₂Cl₂ (3.75 mL, 7.50 mmol), follow by 4 drops of DMF. The mixture was stirred at ambient temperature for one hour, concentrated, and further dried under high vacuum. The residue was re-dissolved in CH₂Cl₂ (10 mL), to this solution was added 2.0 M methylamine in THF (3.5 mL, 7.50 mmol). After stirring at ambient temperature overnight, the reaction was quenched with water, extracted with CH₂Cl₂ for three times. The combined organic phase was dried over Na₂SO₄, and concentrated to give 0.46 g white solid as the intermediate 70a. ¹H NMR (300 MHz, CD₃OD) δ 7.14 (d, 1H, J=8.66 Hz), 6.87 (d, 1H, J=2.64 Hz), 6.78–6.72 (m, 1H), 3.68 (s, 3H), 3.48 (s, 2H), 2.62 (s, 3H). LCMS (ESI+) [M+H]/z Calc'd 214, found 214.

Intermediate 70b: 2-Bromo-2-(2-chloro-4-methoxy-phenyl)-N-methyl-acetamide

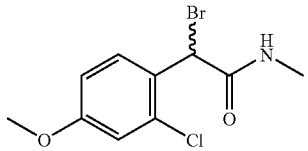

A mixture of 2-(2-chloro-4-methoxy-phenyl)-N-methyl-acetamide (70a) (0.22 g, 1.03 mmol), NBS (183 mg, 1.03 mmol), and 70% benzyl peroxide (36 mg, 0.103 mmol) in 6 mL of $CCl_4$ was refluxed at 80° C. for three hours, cooled to room temperature, filtered, and concentrated in vacuo. The residue was purified by flash column chromatography eluting with 1:1 EtOAc and hexanes to provide 185 mg white solid as the intermediate 70b. $^1$H NMR (300 MHz, $CDCl_3$) δ 7.42 (d, 1H, J=8.85 Hz), 6.90 (d, 1H, J=2.63 Hz), 6.83–6.76 (m, 1H), 5.83 (s, 1H), 3.78 (s, 3H), 2.90 (d, 3H, J=4.90 Hz). LCMS (ESI+) [M+H]/z Calc'd 294, found 294.

Intermediate 70c: 2-(2-Chloro-4-hydroxy-phenyl)-2-methoxy-N-methyl-acetamide

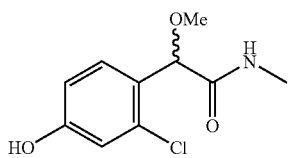

To a solution of 2-bromo-2-(2-chloro-4-methoxy-phenyl)-N-methyl-acetamide (70b) (185 mg, 0.632 mmol) in 5 mL of $CH_2Cl_2$ was added 1.0 M $BBr_3$ (1.90 mL, 1.90 mmol) in $CH_2Cl_2$ at 0° C. The mixture was stirred at 0° C. to room temperature for two hours. The reaction was quenched with MeOH, neutralized with concentrated aqueous $NH_4OH$. The resulting mixture was stirred at room temperature for one hour. Water was added, the mixture was extracted with $CH_2Cl_2$ for three times. The combined organic layer was dried over $Na_2SO_4$, concentrated, and purified by flash column chromatography eluting with 3:1 EtOAc and hexanes to provide 80 mg white solid as the intermediate 70c. $^1$H NMR (300 MHz, $CD_3OD$) δ 8.06 (s, 1H), 7.06 (d, 1H, J=8.48 Hz), 6.73 (d, 1H, J=2.45 Hz), 6.65–6.59 (m, 1H), 4.91 (s, 1H), 3.22 (s, 3H), 2.69 (s, 3H, J=4.71 Hz). LCMS (ESI+) [M+H]/z Calc'd 230, found 230.

The compound of Example 70 was prepared from the coupling of (7-chloro-thieno[3,2-b] pyridin-2-yl)-((R)-3-hydroxy-pyrrolidin-1-yl)-methanone (2b) and intermediate 70c following Method C. $^1$H NMR (300 MHz, $CD_3OD$) δ 8.46 (d, 1H, J=5.46 Hz), 7.85 (d, 1H, J=17.33 Hz), 7.45 (d, 1H, J=8.47 Hz), 7.31 (d, 1H, J=2.26 Hz), 7.18–7.13 (m, 1H), 6.73 (d, 1H, J=5.46 Hz), 5.07 (s, 1H), 4.42 (bs, 1H), 4.03–3.90 (m, 2H), 3.74–3.58 (m, 3H), 3.31 (s, 3H), 2.72 (s, 3H), 2.06–1.97 (m, 2H). LCMS (ESI+) [M+H]/z Calc'd 476, found 476. Anal. ($C_{22}H_{22}N_3O_5SCl$. 0.2$CH_2Cl_2$.0.2EtOAc), C, H, N.

Example 71

2-{2-Chloro-4-[2-((R)-3-hydroxy-pyrrolidine-1-carbonyl)-thieno[3,2-b]pyridin-7-yloxy]-phenyl}-2-hydroxy-N-methyl-acetamide

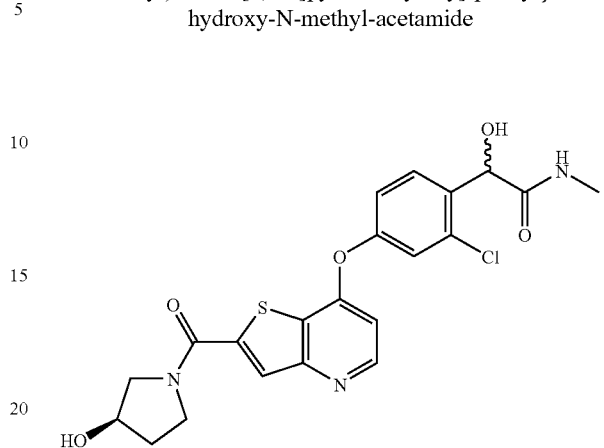

was prepared from the title compound of Example 70 following Method D. $^1$H NMR (300 MHz, $CD_3OD$) δ 8.46 (d, 1H, J=5.46 Hz), 7.85 (d, 1H, J=17.52 Hz), 7.46 (d, 1H, J=8.48 Hz), 7.28 (d, 1H, J=2.45 Hz), 7.16–7.08 (m, 1H), 6.71 (d, 1H, J=5.46 Hz), 5.41 (s, 1H), 4.42 (bs, 1H), 4.03–3.90 (m, 3H), 3.74–3.58(m, 2H), 2.73 (s, 3H), 2.12–1.97(m, 2H). LCMS (ESI+) [M+H]/z Calc'd 462, found 462 Anal. ($C_{21}H_{20}N_3O_5SCl$.0.7$CH_2Cl_2$) C, H, N.

Example 72

2-{2-Chloro-4-[2-(1-methyl-1H-imidazol-2-yl)-thieno[3,2-b]pyridin-7-yloxy]-phenyl}-2-methoxy-N-methyl-acetamide

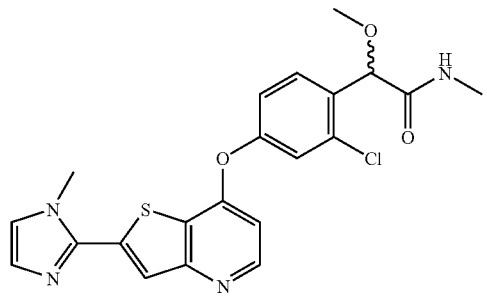

was prepared from the coupling of 7-chloro-2-(1-methyl-1H-imidazol-2-yl)-thieno[3,2-b]pyridine and intermediate 70c following Method C. $^1$H NMR (300 MHz, $CD_3OD$) δ 8.42 (d, 1H, J=5.46 Hz), 7.71 (s, 1H), 7.48 (d, 1H, J=8.47 Hz), 7.34 (d, 1H, J=2.26 Hz), 7.24 (s, 1H), 7.21–7.15 (m, 1H), 7.02 (s, 1H), 6.69 (d, 1H, J=5.46 Hz), 5.09 (s, 1H), 3.94 (s, 3H), 3.34 (s, 3H), 2.75 (s, 3H). LCMS (ESI+) [M+H]/z Calc'd 443, found 443. Anal. ($C_{21}H_{19}N_4O_3SCl$.0.7$CH_2Cl_2$.0.3EtOAc) C, H, N.

Example 73

2-{2-Chloro-4-[2-(1-methyl-1H-imidazol-2-yl)-thieno[3,2-b]pyridin-7-yloxy]-phenyl}-2-hydroxy-N-methyl-acetamide

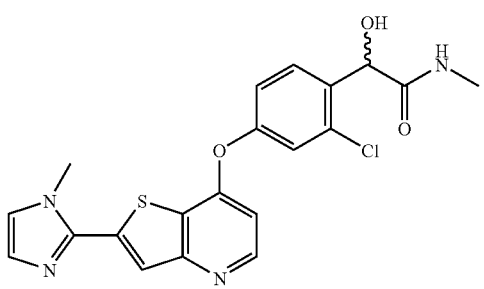

was prepared from the title compound of Example 72 following Method D. ¹H NMR (300 MHz, CD₃OD) δ 8.41 (d, 1H, J=5.46 Hz), 7.70 (s, 1H), 7.46 (d, 1H, J=8.47 Hz), 7.28 (d, 1H, J=2.45 Hz), 7.21 (s, 1H), 7.16–7.10 (m, 1H), 7.00 (s, 1H), 6.67 (d, 1H, J=5.65 Hz), 5.39 (s, 1H), 3.92 (s, 3H), 2.73 (s, 3H). LCMS (ESI+) [M+H]/z Calc'd 429, found 429. Anal. (C₂₀H₁₇N₄O₃SCl.0.5EtOAc.0.5MeOH)C, H, N.

Example 74

2-{4-[2-(Azetidine-1-carbonyl)-thieno[3,2-b]pyridin-7-yloxy]-phenyl}-2-hydroxy-N-methyl-acetamide

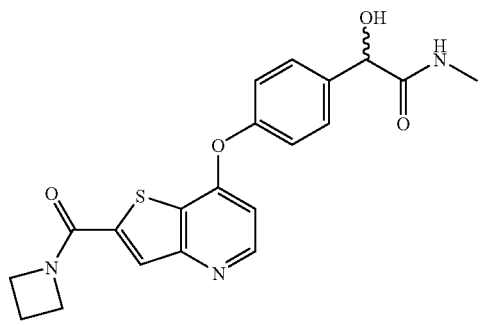

Intermediate 74a:
2-(4-Methoxy-phenyl)-N-methyl-2-oxo-acetamide

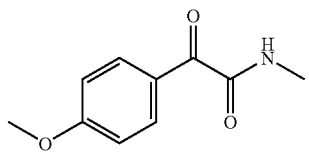

To a solution of ethyl-4-methoxylbenzoformate (2.00 g, 7.99 mmol) in 17 mL of THF was added dropwise 0.33 N KOH (55 mL) at 0° C. The mixture was stirred at room temperature for three hours, and concentrated in vacuo. Saturated aqueous NaHCO₃ solution was added, and the mixture was extracted with EtOAc. The combined organic layer was dried over Na₂SO₄, and concentrated to give 1.969 acid as white solid. It was dissolved in 10 mL of DMF, and to this solution was added 2.0 M methylamine in THF (21.78 mL, 43.56 mmol) and Et₃N (6.07 mL, 43.56 mmol), follow by HATU (6.71 g, 17.65 mmol). The resulting mixture was stirred at room temperature for one hour. Water was added, the mixture was extracted with EtOAc. The organic phase was dried over Na₂SO₄, concentrated, and purified by flash column chromatography eluting with EtOAc:CH₂Cl₂:MeOH (1:1:0.01) to provide 1.35 g off-white solid as the intermediate 74a. ¹H NMR (300 MHz, CD₃OD) δ 8.03 (d, 2H, J=9.04 Hz), 6.94 (d, 2H, J=9.04 Hz), 3.80 (s, 3H), 2.78 (s, 3H). LCMS (ESI+) [M+H]/z Calc'd 194, found 194.

Intermediate 74b:
2-(4-Hydroxy-phenyl)-N-methyl-2-oxo-acetamide

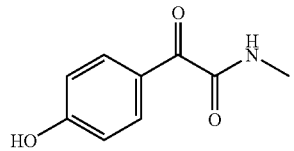

To a solution of 2-(4-methoxy-phenyl)-N-methyl-2-oxo-acetamide (74a) (1.35 g, 6.99 mmol) in 25 mL of CH₂Cl₂ was added 1.0 M BBr₃ in CH₂Cl₂ (14 mL, 28.0 mmol) at 0° C. The mixture was stirred at 0° C. to room temperature for two hours. The reaction was quenched with MeOH, neutralized with concentrated aqueous NH₄OH to pH ~7. The resulting mixture was stirred at room temperature for one hour. Water was added, and the mixture was extracted with CH₂Cl₂. The organic phase was dried over Na₂SO₄, concentrated, and purified by flash column chromatography eluting with 1:1 EtOAc and hexanes to provide 0.53 g off-white solid as the intermediate 74b. ¹H NMR (300 MHz, CD₃OD) δ 7.03 (d, 2H, J=8.86 Hz), 6.75 (d, 2H, J=8.86 Hz), 2.76 (s, 3H). LCMS (ESI+) [M+Na]/z Calc'd 202, found 202.

Intermediate 74c:
2-Hydroxy-2-(4-hydroxy-phenyl)-N-methyl-acetamide

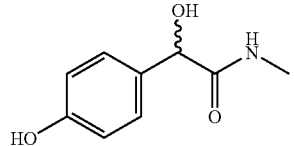

To solution of 2-(4-hydroxy-phenyl)-N-methyl-2-oxo-acetamide (74b) (121 mg, 0.676 mmol) in 3 mL of MeOH was added NaBH₄ (51 mg, 1.352 mmol). The mixture was stirred at room temperature for 30 min, and concentrated. 1.0 N aqueous HCl solution was added, the mixture was extracted with EtOAc for three times. The organic phase was dried over Na₂SO₄, and concentrated to give 114 mg of the intermediate 74c as a white solid. ¹H NMR (300 MHz, CD₃OD) δ 7.18 (d, 2H, J=8.48 Hz), 6.67 (d, 2H, J=8.48 Hz), 4.78 (s, 1H), 2.61 (s, 3H). LCMS (ESI+) [M+Na]/z Calc'd 204, found 204.

The compound of Example 74 was prepared from coupling of azetidin-1-yl-(7-chloro-thieno[3,2-b]pyridin-2-yl)-methanone (21a) and intermediate 74c following Method C. ¹H NMR (300 MHz, CD₃OD) δ 8.41 (d, 1H, J=5.47 Hz), 7.72 (s, 1H), 7.52 (d, 2H, J=8.48 Hz), 7.14 (d, 2H, J=8.48 Hz), 6.61 (d, 1H, J=5.47 Hz), 4.97 (s, 1H), 4.67–4.57 (m, 2H), 4.23–4.13(m, 2H), 2.69 (s, 3H), 2.45–2.33 (m, 2H). LCMS (ESI+) [M+H]/z Calc'd 398, found 398. Anal. (C₂₀H₁₉N₃O₄S.0.6CH₂Cl₂) C, H, N.

Example 75

2-Hydroxy-2-(4-{2-[4-(1-hydroxy-1-methyl-ethyl)-thiazol-2-yl]-thieno[3,2-b]pyridin-7-yloxy}-phenyl)-N-methyl-acetamide

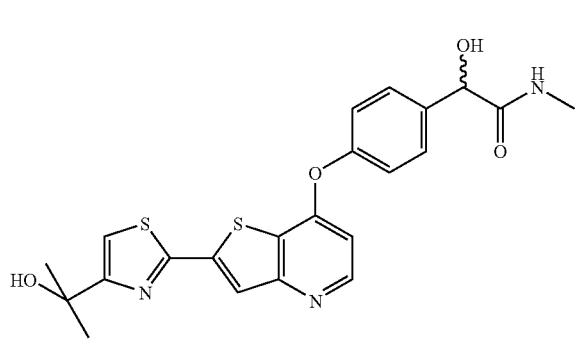

was prepared from the coupling of 2-[2-(7-chloro-thieno[3,2-b]pyridin-2-yl)-thiazol-4-yl]-propan-2-ol and intermediate 74c following Method C. ¹H NMR (300 MHz, CD₃OD) δ 8.36 (d, 1H, J=5.46 Hz), 7.82 (s, 1H), 7.61 (d, 2H, J=8.66 Hz), 7.39 (s, 1H), 7.15 (d, 2H, J=8.66 Hz), 6.61 (d, 1H, J=5.47 Hz), 4.98 (s, 1H), 2.69 (s, 3H), 1.52 (s, 6H). LCMS (ESI+) [M+H]/z Calc'd 456, found 456. Anal. (C₂₂H₂₁N₃O₄S₂.0.2CH₂Cl₂) C, H, N.

Example 76

2-Hydroxy-2-{4-[2-((R)-3-hydroxy-pyrrolidine-1-carbonyl)-thieno[3,2-b]pyridin-7-yloxy]-phenyl}-N-methyl-acetamide

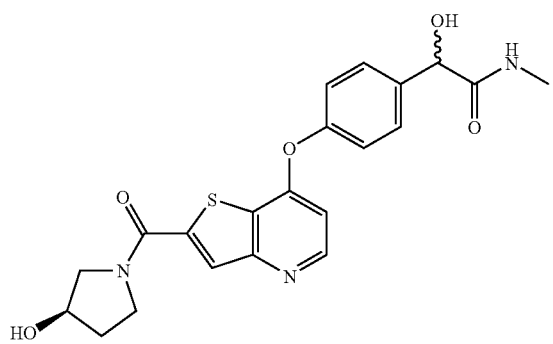

was prepared from coupling of (7-chloro-thieno[3,2-b]pyridin-2-yl)-(3-hydroxy-pyrrolidin-1-yl)-methanone (2b) and intermediate 74c following Method C. ¹H NMR (300 MHz, CD₃OD) δ 8.41 (d, 1H, J=5.47 Hz), 7.84 (d, 1H, J=17.33 Hz), 7.52 (d, 2H, J=8.48 Hz), 7.14 (d, 2H, J=8.48 Hz), 6.61 (d, 1H, J=5.47 Hz), 5.09 (s, 1H), 4.42 (bs, 1H), 4.23–3.90 (m, 2H), 3.89–3.54(m, 3H), 2.69 (s, 3H), 2.20–1.97(m, 2H). LCMS (ESI+) [M+H]/z Calc'd 428, found 428. Anal. (C₂₁H₂₁N₃O₅S.0.6CH₂Cl₂.1.0H₂O)C, H, N.

Example 77

2-Hydroxy-2-{4-[2-((R)-3-methoxy-pyrrolidine-1-carbonyl)-thieno[3,2-b]pyridin-7-yloxy]-phenyl}-N-methyl-acetamide

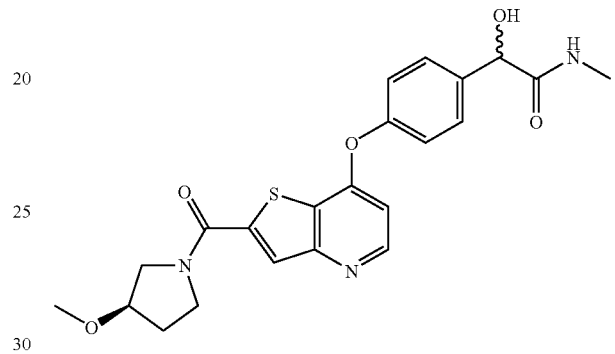

was prepared from coupling of (7-chloro-thieno[3,2-b]pyridin-2-yl)-(3-methoxy-pyrrolidin-1-yl)-methanone (62a) and intermediate 74c following Method C. ¹H NMR (300 MHz, CD₃OD) δ 8.41 (d, 1H, J=5.47 Hz), 7.82 (s, 1H), 7.52 (d, 2H, J=8.48 Hz), 7.14 (d, 2H, J=8.48 Hz), 6.61 (d, 1H, J=5.47 Hz), 4.98 (s, 1H), 4.08–3.76 (m, 5H), 3.75–3.52 (m, 2H), 2.69 (s, 3H), 2.33–1.97(m, 2H). LCMS (ESI+) [M+H]/z Calc'd 442, found 442. Anal. (C₂₂H₂₃N₃O₅S.2.0H₂0)C, H, N.

Example 78

2-{4-[2-((R)-3-Methoxy-pyrrolidine-1-carbonyl)-thieno[3,2-b]pyridin-7-yloxy]-phenyl}-N-methyl-2-oxo-acetamide

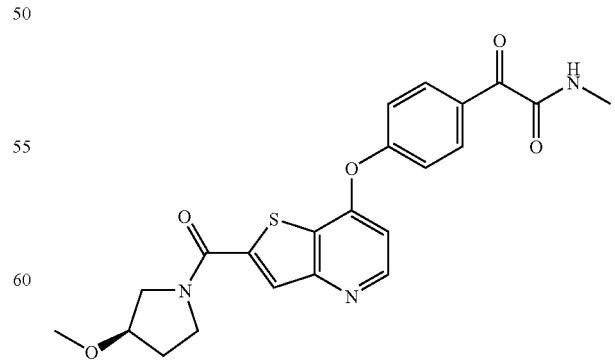

To a solution of Dess-Martin reagent (48 mg, 0.114 mmol) in 1.5 mL of CH₂Cl₂ cooled to 0° C., was added dropwise a solution of 2-hydroxy-2-{4-[2-((R)-3-methoxy-pyrrolidine-1-carbonyl)-thieno[3,2-b]pyridin-7-yloxy]-phenyl}-N-methyl-acetamide (Example 77) (42 mg, 0.095 mmol) in 1.5 mL of CH$_2$Cl$_2$. The mixture was stirred at 0° C. to room temperature for one hour. Saturated aqueous NaHCO$_3$ solution was added, and the mixture was extracted with CH$_2$Cl$_2$ and a small amount of MeOH. The combined organic phase was dried over Na$_2$SO$_4$, concentrated, and purified by flash column chromatography eluting with EtOAc:CH$_2$Cl$_2$:MeOH (1:1:0.04) to provide 30 mg white solid as the compound of Example 78. $^1$H NMR (300 MHz, CD$_3$OD) δ 8.47 (d, 1H, J=5.47 Hz), 8.17 (d, 2H, J=8.66 Hz), 7.28 (d, 2H, J=8.66 Hz), 7.78–7.62 (m, 1H), 6.81 (d, 1H, J=5.47 Hz), 4.08–3.76 (m, 5H), 3.75–3.52 (m, 3H), 2.78 (s, 3H), 2.30–1.97 (m, 2H). LCMS (ESI+) [M+H]/z Calc'd 440, found 440. Anal. (C$_{22}$H$_{21}$N$_3$O$_5$S.0.4CH$_2$Cl$_2$) C, H, N.

Example 79

2-{4-[2-(Azetidine-1-carbonyl)-thieno[3,2-b]pyridin-7-yloxy]-phenyl}-2-methoxy-N-(3-methyl-isoxazol-5-yl)-acetamide

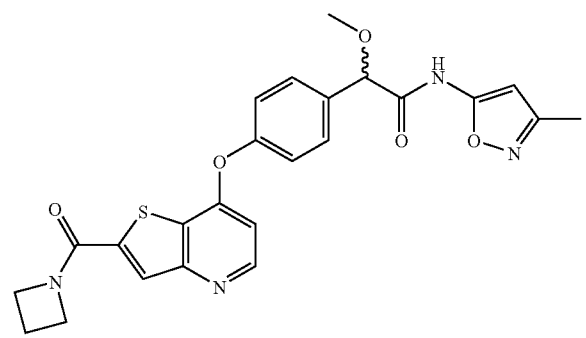

Intermediate 79a:
acetoxy-(4-methoxy-phenyl)-acetic acid

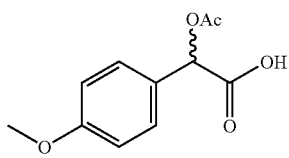

4-Methoxymandelic acid (5.00 g, 27.44 mmol) was dissolved in 100 mL of THF. To this solution was added acetic anhydride (2.85 mL, 30.18 mmol), followed by Et$_3$N (10 mL). The resulting mixture was stirred at room temperature overnight, concentrated, re-suspended in water, and extracted with EtOAc. The combined organic phase was dried over Na$_2$SO$_4$, and concentrated to give 5.95 g yellow syrup as the intermediate 79a. $^1$H NMR (300 MHz, CDCl$_3$) δ 7.38 (d, 2H, J=8.67 Hz), 6.90 (d, 2H, J=8.67 Hz), 5.87 (s, 1H), 3.80 (s, 3H), 2.16 (s, 3H). LCMS (ESI–) [M–H]/z Calc'd 223, found 223.

Intermediate 79b: acetic acid (4-methoxy-phenyl)-(3-methyl-isoxazol-5-ylcarbamoyl)-methyl ester

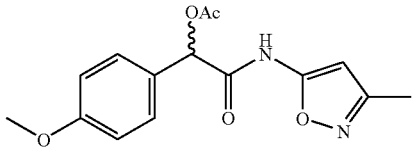

To a suspension of acetoxy-(4-methoxy-phenyl)-acetic acid (79a) (2.78 g, 12.40 mmol) in CH$_2$Cl$_2$ (50 mL), was added 2.0 M oxalyl chloride in CH$_2$Cl$_2$ (9.30 mL, 18.60 mmol), followed by 10 drops of DMF. The mixture was stirred at ambient temperature for one hour, concentrated and further dried under high vacuum. It was re-dissolved in CH$_2$Cl$_2$ (50 mL); to this solution was added 5-amino-3-methylisoxazole (1.34 g, 13.66 mmol), followed by Et$_3$N (2.60 mL, 18.60 mmol). After stirring at ambient temperature overnight, the mixture was concentrated in vacuo and purified by flash column chromatography eluting with 1:1 EtOAc and hexanes to provide 2.70 g yellow solid as the intermediate 79b. $^1$H NMR (300 MHz, CDCl$_3$) δ 8.56 (s, 1H), 7.36 (d, 2H, J=8.67 Hz), 6.90 (d, 2H, J=8.67 Hz), 6.24 (s, 1H), 6.17 (s, 1H), 3.80 (s, 3H), 2.25 (s, 3H), 2.22 (s, 3H). LCMS (ESI—) [M–H]/z Calc'd 303, found 303.

Intermediate 79c: 2-(4-Hydroxy-phenyl)-2-methoxy-N-(3-methyl-isoxazol-5-yl)-acetamide

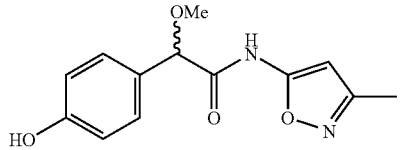

To a solution of acetic acid (4-methoxy-phenyl)-(3-methyl-isoxazol-5-ylcarbamoyl)-methyl ester (79b) (1.07 g, 3.52 mmol) in 40 mL of CH$_2$Cl$_2$, was added 1.0 M BBr$_3$ in CH$_2$Cl$_2$ (8.8 mL, 8.80 mmol) at 0° C. The mixture was stirred at 0° C. to room temperature for two hours. The reaction was quenched with MeOH, and then neutralized with concentrated aqueous NH$_4$OH. The resulting mixture was stirred at room temperature for one hour. Water was added. The mixture was extracted with CH$_2$Cl$_2$. The combined organic layer was dried over Na$_2$SO$_4$, concentrated, and purified by flash column chromatography eluting with 1:1 EtOAc and hexanes to provide 0.57 g yellow solid as the intermediate 79c. $^1$H NMR (300 MHz, CD$_3$OD) δ 7.53 (d, 2H, J=7.53 Hz), 6.83 (d, 2H, J=7.54 Hz), 6.25 (s, 1H), 4.90 (s, 1H), 3.40 (s, 3H), 2.25 (s, 3H). LCMS (ESI+) [M+H]/z Calc'd 263, found 263.

The compound of Example 79 was prepared from coupling of azetidin-1-yl-(7-chloro-thieno[3,2-b]pyridin-2-yl)-methanone (21a) and intermediate 79c following Method C. $^1$H NMR (300 MHz, CD$_3$OD) δ 8.41 (d, 1H. J=5.46 Hz), 7.70 (s, 1H), 7.55 (d, 2H, J=8.67 Hz), 7.20 (d, 2H, J=8.47 Hz), 6.62 (d, 1H, J=5.46 Hz), 6.14 (s, 1H), 4.87 (s, 1H), 4.63–4.52 (m, 2H), 4.21–4.09 (m, 2H), 3.39 (s, 3H), 2.43–2.29 (m, 2H), 2.14 (s, 3H). LCMS (ESI+) [M+H]/z Calc'd 479, found 479. Anal. (C$_{24}$H$_{22}$N$_4$O$_5$S.0.1CH$_2$Cl$_2$) C, H, N.

Example 80

2-{4-[2-(Azetidine-1-carbonyl)-thieno[3,2-b]pyridin-7-yloxy]-phenyl}-2-hydroxy-N-(3-methyl-isoxazol-5-yl)-acetamide

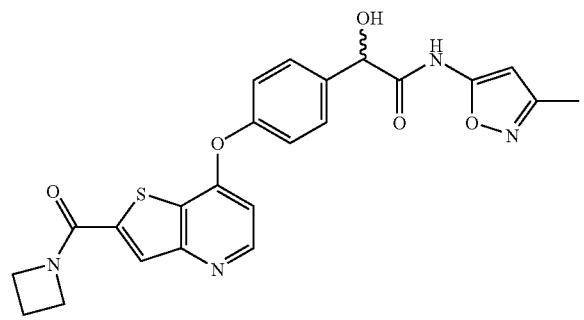

was prepared from the title compound of Example 79 following Method D. $^1$H NMR (300 MHz, CD$_3$OD) δ 8.43 (d, 1H, J=5.65 Hz), 7.74 (s, 1H), 7.60(d, 2H, J=8.67 Hz), 7.19 (d, 2H, J=8.48 Hz), 6.45 (d, 1H, J=5.46 Hz), 6.16 (s, 1H), 5.21 (s, 1H), 4.63–4.52 (m, 2H), 4.21–4.09 (m, 2H), 2.43–2.29 (m, 2H), 2.15 (s, 3H). LCMS (ESI+) [M+H]/z Calc'd 465, found 465. Anal. (C$_{23}$H$_{20}$N$_4$O$_5$S.0.4CH$_2$Cl$_2$) C, H, N.

Example 81

2-{4-[2-(Azetidine-1-carbonyl)-thieno[3,2-b]pyridin-7-yloxy]-phenyl}-N-butyl-2-methoxy-acetamide

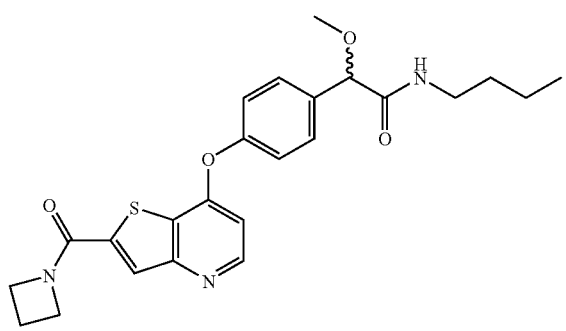

Intermediate 81a: Acetic acid butylcarbamoyl-(4-methoxy-phenyl)-methyl ester

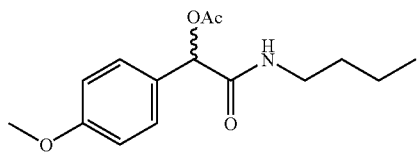

was prepared from intermediate 79a and butylamine following Method A. $^1$H NMR (300 MHz, CDCl$_3$) δ 7.34 (d, 2H, J=8.85 Hz), 6.87 (d, 2H, J=8.67 Hz), 6.01 (s, 1H), 3.79 (s, 3H), 3.31–3.23 (m, 2H), 2.15 (s, 3H), 1.54–1.43 (m, 2H), 1.37–1.22 (m, 2H), 0.94–0.87 (m, 3H). LCMS (ESI+) [2M+Na]/z Calc'd 581, found 581.

Intermediate 81 b: N-Butyl-2-(4-hydroxy-phenyl)-2-methoxy-acetamide

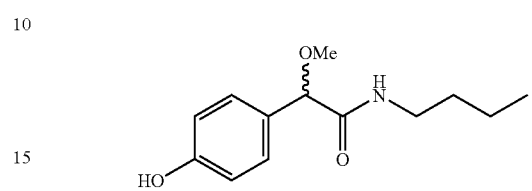

was prepared from intermediate 81a following a similar procedure as in the conversion of 79b to 79c. $^1$H NMR (300 MHz, CD$_3$OD) δ 7.06(d, 2H, J=8.67 Hz), 6.62 (d, 2H, J=8.66 Hz), 4.36 (s, 1H), 3.15 (s, 3H), 3.10–3.02 (m, 2H), 1.40–1.28 (m, 2H), 1.23–1.09 (m, 2H), 0.80–0.70 (m, 3H). LCMS (ESI+) [M+H]/z Calc'd 238, found 238.

The compound of Example 81 was prepared from coupling of azetidin-1-yl-(7-chloro-thieno[3,2-b]pyridin-2-yl)-methanone and intermediate 81b following Method C. $^1$H NMR (300 MHz, CD$_3$OD) δ 8.43 (d, 1H, J=5.46 Hz), 7.74 (s, 1H), 7.53(d, 2H, J=8.66 Hz), 7.16 (d, 2H, J=8.48 Hz), 6.63 (d, 1H, J=5.47 Hz), 4.62 (s, 1H), 4.62–4.54 (m, 2H), 4.19–4.00 (m, 2H), 3.33 (s, 3H), 3.21–3.09 (m, 2H), 2.44–2.30 (m, 2H), 1.49–1.36 (m, 2H), 1.31–1.18 (m, 2H), 0.89–0.77 (m, 3H). LCMS (ESI+) [M+H]/z Calc'd 454, found 454. Anal. (C$_{24}$H$_{27}$N$_3$O$_4$S.0.1CH$_2$Cl$_2$) C, H, N.

Example 82

2-{4-[2-(Azetidine-1-carbonyl)-thieno[3,2-b]pyridin-7-yloxy]-phenyl}-N-butyl-2-hydroxy-acetamide

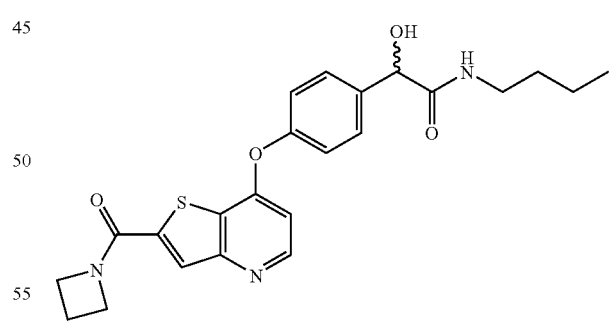

was prepared from the title compound of Example 81 following Method D. $^1$H NMR (300 MHz, CD$_3$OD) δ 8.40 (d, 1H, J=5.46 Hz), 7.67 (s, 1H), 7.49(d, 2H, J=8.47 Hz), 7.18 (d, 2H, J=8.48 Hz), 6.61 (d, 1H, J=5.47 Hz), 4.99 (s, 1H), 4.66–4.56 (m, 2H), 4.22–4.12 (m, 2H), 3.21–3.12 (m, 2H), 2.46–2.36 (m, 2H), 1.49–1.36 (m, 2H), 1.31–1.18 (m, 2H), 0.89–0.77 (m, 3H). LCMS (ESI+) [M+H]/z Calc'd 440, found 440. Anal. (C$_{23}$H$_{25}$N$_3$O$_4$S.0.2CH$_2$Cl$_2$) C, H, N.

Example 83

2-{4-[2-(Azetidine-1-carbonyl)-thieno[3,2-b]pyridin-7-yloxy]-phenyl}-2-methoxy-N-pyridin-2-yl-acetamide

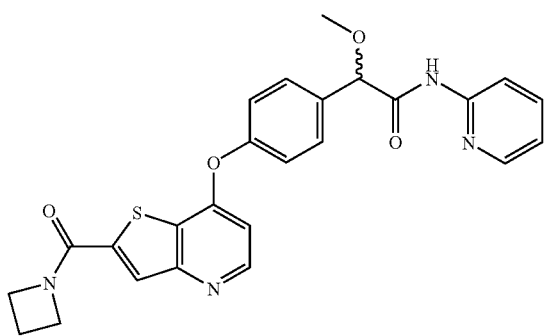

Intermediate 83a: Acetic acid (4-methoxy-phenyl)-(pyridin-2-ylcarbamoyl)-methyl ester

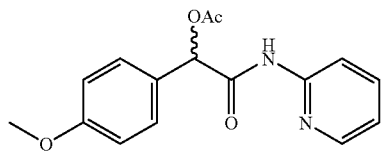

was prepared from intermediate 79a and 2-aminopyridine following Method A. ¹H NMR (300 MHz, CDCl₃) δ 9.06 (s, 1H), 8.31–8.23 (m, 2H), 7.81–7.75 (m, 1H), 7.43 (d, 2H, J=8.59 Hz), 6.90 (d, 2H, J=8.59 Hz), 6.14 (s, 1H), 3.79 (s, 3H), 2.25 (s, 3H). LCMS (ESI+) [M+H]/z Calc'd 301, found 301.

Intermediate 83b: 2-(4-Hydroxy-phenyl)-2-methoxy-N-pyridin-2-yl-acetamide

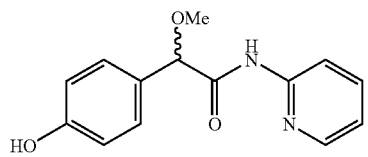

was prepared from intermediate 83a following a similar procedure as in the conversion of intermediate 79b to intermediate 79c. ¹H NMR (300 MHz, CD₃OD) δ 8.21 (d, 1H, J=5.05 Hz), 8.01 (d, 1H J=8.34 Hz), 7.72–7.66 (m, 1H), 7.20 (d, 2H, J=8.59 Hz), 7.08–7.01 (m, 1H), 6.72 (d, 2H, J=8.34 Hz), 4.66 (s, 1H), 3.31 (s, 3H). LCMS (ESI+) [M+H]/z Calc'd 259, found 259.

The compound of Example 83 was prepared from coupling of azetidin-1-yl-(7-chloro-thieno[3,2-b]pyridin-2-yl)-methanone (21a) and intermediate 83b following Method C. ¹H NMR (300 MHz, CD₃OD) δ 8.38 (d, 1H, J=5.28 Hz), 8.24–8.15 (m, 1H), 8.00 (d, 1H, J=8.29 Hz), 7.72–7.62 (m, 2H), 7.55 (d, 2H, J=8.29 Hz), 7.18 (d, 2H, J=8.29 Hz), 7.09–6.99 (m, 1H), 6.61 (d, 1H, J=5.27 Hz), 5.39 (s, 1H), 4.63–4.48 (m, 2H), 4.21–4.08 (m, 2H), 3.40 (s, 3H), 2.45–2.28 (m, 2H). LCMS (ESI+) [M+H]/z Calc'd 475, found 475. Anal. (C₂₅H₂₂N₄O₄S.0.4EtOAc.0.3CH₂Cl₂) C, H, N.

Example 84

2-{4-[2-(Azetidine-1-carbonyl)-thieno[3,2-b]pyridin-7-yloxy]-phenyl}-2-hydroxy-N-pyridin-2-yl-acetamide

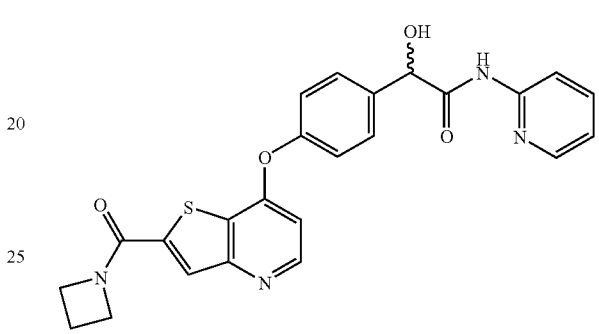

was prepared from the title compound of Example 83 following Method D. ¹H NMR (300 MHz, CD₃OD) δ 8.42 (d, 1H, J=5.46 Hz), 8.26–8.20 (m, 1H), 8.06 (d, 1H, J=8.29 Hz), 7.77–7.69 (m, 2H), 7.63 (d, 2H, J=8.67 Hz), 7.19 (d, 2H, J=8.66 Hz), 7.11–7.03 (m, 1H), 6.65 (d, 1H, J=5.65 Hz), 5.20 (s, 1H), 4.65–4.55 (m, 2H), 4.23–4.13 (m, 2H), 2.47–2.33 (m, 2H). LCMS (ESI+) [M+H]/z Calc'd 461, found 461. Anal. (C₂₄H₂₀N₄O₄S.0.7EtOAc.0.5CH₂Cl₂) C, H, N.

Example 85

2-Methoxy-2-{4-[2-(1-methyl-1H-imidazol-2-yl)-thieno[3,2-b]pyridin-7-yloxy]-phenyl}-N-pyridin-2-yl-acetamide

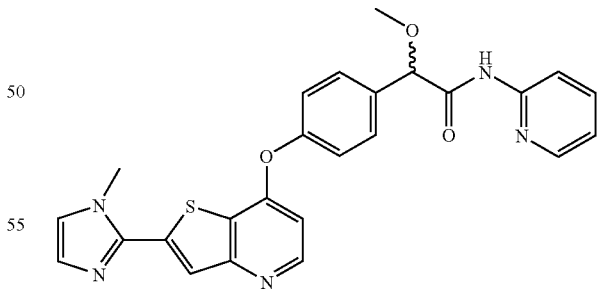

was prepared from coupling of 7-chloro-2-(1-methyl-1H-imidazol-2-yl)-thieno[3,2-b]pyridine and intermediate 83b following Method C. ¹H NMR (300 MHz, CD₃OD) δ 8.44 (d, 1H, J=5.31 Hz), 8.00 (d, 2H, J=9.10 Hz), 7.78–7.74 (m, 1H), 7.72 (s, 1H), 7.38–7.32 (m, 1H), 7.28–7.20 (m, 3H), 7.00 (s, 1H), 6.61 (d, 1H, J=5.27 Hz), 6.51–6.45 (m, 2H), 3.93 (s, 3H), 3.83 (s, 3H). LCMS (ESI+) [M+H]/z Calc'd 472, found 472. Anal. (C₂₅H₂₁N₅O₃S.0.5EtOAc.1.0CH₂Cl₂) C, H, N.

Example 86 butyl-carbamic acid 4-[2-(azetidine-1-carbonyl)-thieno[3,2-b]pyridin-7-yloxy]-phenyl ester

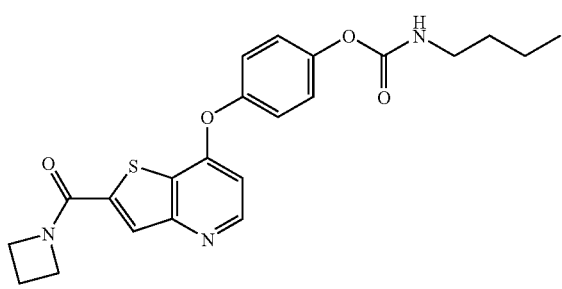

Intermediate 86a: Azetidin-1-yl-[7-(4-methoxy-phenoxy)-thieno[3,2-b]pyridin-2-yl]-methanone

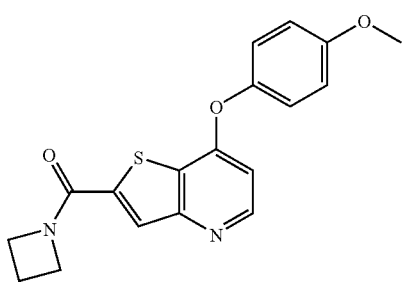

A mixture of azetidin-1-yl-(7-chloro-thieno[3,2-b]pyridin-2-yl)-methanone (21a) (200 mg, 0.794 mmol), 4-methoxyphenol (148 mg, 1.191 mmol), and $Cs_2CO_3$ (391 mg, 1.191 mmol) in 2 mL of DMSO was heated at 100° C. for overnight. It was cooled to room temperature, EtOAc and 1.0 N NaOH were added. The organic layer was washed with water and brine, dried over $Na_2SO_4$, and concentrated to give 0.27 g of the intermediate 86a as off-white solid. $^1$H NMR (300 MHz, $CDCl_3$) δ 8.46 (d, 1H, J=5.46 Hz), 7.75 (s, 1H), 7.09 (d, 2H, J=9.05 Hz), 6.94 (d, 2H, J=9.04 Hz), 6.53 (d, 1H, J=5.46 Hz), 4.63–4.53 (m, 2H), 4.31–4.20 (m, 2H), 2.40–2.36 (m, 2H). LCMS (ESI+) [M+H]/z Calc'd 341, found 341.

Intermediate 86b: azetidin-1-yl-[7-(4-hydroxy-phenoxy)-thieno[3,2-b]pyridin-2-yl]-methanone

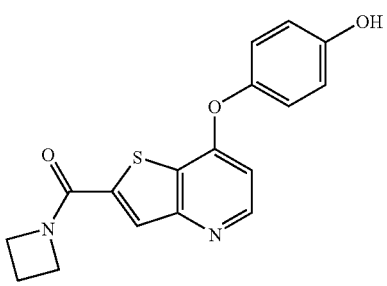

To a solution of azetidin-1-yl-[7-(4-methoxy-phenoxy)-thieno[3,2-b]pyridin-2-yl]-methanone (86a) (400 mg, 1.176 mmol) in 10 mL of $CH_2Cl_2$ was added 1.0 M $BBr_3$ (3.53 mL, 3.53 mmol). The mixture was stirred at room temperature overnight. The reaction was quenched with MeOH, and then neutralized with concentrated aqueous $NH_4OH$ to pH ~7. The resulting mixture was stirred at room temperature for one hour. Water was added; the mixture was extracted with $CH_2Cl_2$. The combined organic layer was dried over $Na_2SO_4$, concentrated, and purified by flash column chromatography eluting with EtOAc:Hex:MeOH (1:1:0.01) to provide 187 mg off-white solid as the intermediate 86b. $^1$H NMR (300 MHz, $CD_3OD$) δ 8.39 (d, 1H, J=5.56 Hz), 7.70 (s, 1H), 6.97 (d, 2H, J=8.84 Hz), 6.80 (d, 2H, J=8.84 Hz), 6.57 (d, 1H, J=5.56 Hz), 4.65–4.54 (m, 2H), 4.23–4.11(m, 2H), 2.39–2.33 (m, 2H). LCMS (ESI+) [M+H]/z Calc'd 327, found 327.

To a suspension of azetidin-1-yl-[7-(4-hydroxy-phenoxy)-thieno[3,2-b]pyridin-2-yl]-methanone (86b) (41 mg, 0.126 mmol) in 3 mL of toluene, was added 20% phosgene in toluene (1.38 mL). The mixture was stirred at room temperature for 15 minutes, followed by addition of $Et_3N$ (0.021 ml, 0.151 mmol). The resulting suspension was stirred at room temperature for two hours, and concentrated. It was re-dissolved in 3 mL of THF. To this solution was added n-butyl amine (0.014 mL, 0.139 mmol), followed by $Et_3N$ (0.021 ml, 0.151 mmol). The mixture was stirred at room temperature for two hours, concentrated, and purified by preparative TLC plate eluting with EtOAc:$CH_2Cl_2$:MeOH (1:1:0.05) to provide 14 mg off-white solid as the title compound. $^1$H NMR (300 MHz, $CD_3OD$) δ 8.42 (d, 1H, J=5.65 Hz), 7.72 (s, 1H), 7.16 (s, 4H), 6.65 (d, 1H, J=5.47 Hz), 4.65–4.54 (m, 2H), 4.23–4.11(m, 2H), 3.14–3.05(m, 2H), 2.39–2.33 (m, 2H), 1.53–1.40(m, 2H), 1.39–1.27(m, 2H), 0.92–0.83(m, 3H). LCMS (ESI+) [M+H]/z Calc'd 426, found 426. Anal. ($C_{22}H_{23}N_3O_4S$) C, H, N.

Example 87

N-(5-Chloro-pyridin-2-yl)-2-[4-(7-methoxy-quinolin-4-yloxy)-phenyl]-acetamide

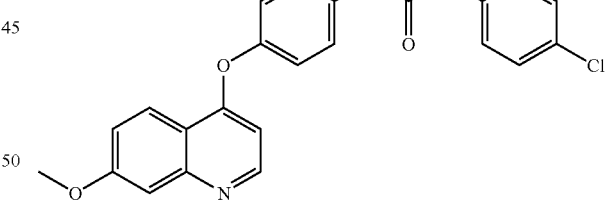

A mixture of 3-methoxyaniline (25 g, 204 mmol) A and diethyl (ethoxymethylene) malonate (44 g, 204 mmol) B were heated in an oil bath to 150° C. for 40 minutes. EtOH was generated when the temperature reached 132° C. and collected. The reaction flask was moved away from oil bath and phenyl ether (70 mL) was added into the reaction mixture. The oil bath was preheated to 270° C. The reaction was heated at 270° C. (oil bath temperature) for 15 minutes. The reaction mixture was poured slowly into 800 ml of hexane with stirring. Ethyl 4-hydroxy-7-methoxyquinoline-3-carboxylate C was precipitated, filtrated, washed with hexane and dried (28.4 g, 56% yield).

A solution of compound C (4.2 g) and KOH (3 g, 3 eq.) in 40 mL of EtOH/$H_2O$ (1:1) was heated by microwave to 180° C. for 50 minutes. The mixture was cooled to room temperature, poured into water (100 mL), neutralized with AcOH to pH 7 and saturated with NaCl. The solution was extracted with THF (3×300 mL) and concentrated to yield 3.1 g of 7-methoxyquinolin-4-ol D as a solid.

Compound D (7.4 g) was dissolved in 20 mL of POCl$_3$. The solution was heated to reflux for 2 hours. The excess amount of POCl$_3$ was removed by evaporation under vacuum. The residue was neutralized with NH$_4$OH to pH ~7 and extracted with EtOAc. The organic layer was concentrated and purified by chromatography on a silica gel column using hexane/ethylacetate (3:1) to give 6.5 g of 4-chloro-7-methoxyquinoline as E as a yellow solid.

Intermediate 87a:
[4-(7-Methoxy-quinolin-4-yloxy)-phenyl]-acetic acid

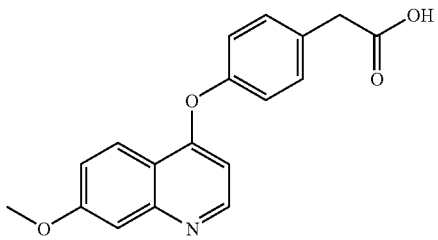

A mixture of 4-chloro-7-methoxy-quinoline (200 mg, 1.036 mmol), 4-hydroxyphenylacetic acid (158 mg, 1.036 mmol), and Cs$_2$CO$_3$ (1.02 g, 3.11 mmol) in 2 mL of DMSO was heated at 100° C. overnight. The mixture was then cooled to room temperature. EtOAc and water were added. The aqueous layer was acidified with 1 N HCl until a precipitate was formed. The solid was filtered and washed with water. The solid was dried in a vacuum-oven at 60° C. overnight. The intermediate 87a (160 mg) was obtained as a brown solid. $^1$H NMR (300 MHz, CD$_3$OD) δ 8.63 (s, 1H), 8.39 (d, 1H, J=9.04 Hz), 7.47–7.28 (m, 4H), 7.16 (d, 2H, J=7.72 Hz), 6.76 (s, 1H), 3.93 (s, 3H), 3.58(s, 2H). LCMS (ESI+) [M+H]/z Calc'd 310, found 310.

The compound of Example 87 was prepared from intermediate 87a and 2-amino-5-chloro pyridine following Method A. $^1$H NMR (300 MHz, CD$_3$OD) δ 8.42 (d, 1H, J=5.47 Hz), 8.20 (s, 1H), 8.18 (d, 1H, J=6.97 Hz), 8.05 (d, 1H, J=8.86 Hz), 7.71–7.65 (m, 1H), 7.43 (d, 2H, J=8.47 Hz), 7.43 (d, 1H, J=2.26 Hz), 7.22–7.10 (m, 1H), 7.12 (d, 2H, J=8.67 Hz), 6.24 (d, 1H, J=5.47 Hz), 3.89 (s, 3H), 3.73(s, 2H). LCMS (ESI+) [M+H]/z Calc'd 420, found 420. Anal. (C$_{23}$H$_{18}$N$_3$O$_3$Cl.0.2CH$_2$Cl$_2$.0.5MeOH) C, H, N.

Biological Testing—Enzyme Assays

The stimulation of cell proliferation by growth factors such as VEFG, FGF, and others is dependent upon their induction of autophosphorylation of each of their respective receptor's tyrosine kinases. Therefore, the ability of a protein kinase inhibitor to block cellular proliferation induced by these growth factors is directly correlated with its ability to block receptor autophosphorylation. To measure the protein kinase inhibition activity of the compounds, the following constructs were devised.

(i) VEGF-R2 Construct for Assay:

This construct determines the ability of a test compound to inhibit tyrosine kinase activity. A construct (VEGF-R2D50) of the cytosolic domain of human vascular endothelial growth factor receptor 2 (VEGF-R2) lacking the 50 central residues of the 68 residues of the kinase insert domain was expressed in a baculovirus/insect cell system. Of the 1356 residues of full-length VEGF-R2, VEGF-R2D50 contains residues 806–939 and 990–1171, and also one point mutation (E990V) within the kinase insert domain relative to wild-type VEGF-R2. Autophosphorylation of the purified construct was performed by incubation of the enzyme at a concentration of 4 mM in the presence of 3 mM ATP and 40 mM MgCl$_2$ in 100 mM HEPES, pH 7.5, containing 5% glycerol and 5 mM DTT, at 4° C. for 2 h. After autophosphorylation, this construct has been shown to possess catalytic activity essentially equivalent to the wild-type autophosphorylated kinase domain construct. See Parast et al., *Biochemistry*, 37, 16788–16801 (1998).

(ii) FGF-R1 Construct for Assay:

The intracellular kinase domain of human FGF-R1 was expressed using the baculovirus vector expression system starting from the endogenous methionine residue 456 to glutamate 766, according to the residue numbering system of Mohammadi et al., *Mol. Cell. Biol.*, 16, 977–989 (1996). In addition, the construct also has the following 3 amino acid substitutions: L457V, C488A, and C584S.

Example A

VEGF-R2 Assay: Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (PK) and lactic dehydrogenase (LDH). The oxidation of NADH was monitored by following the decrease of absorbance at 340 nm ($e_{340}$=6.22 cm$^{-1}$ mM$^{-1}$) using a Beckman DU 650 spectrophotometer. Assay conditions for phosphorylated VEGF-R2D50 (indicated as FLVK-P in the tables below) were the following: 1 mM PEP; 250 mM NADH; 50 units of LDH/mL; 20 units of PK/mL; 5 mM DTT; 5.1 mM poly(E$_4$Y$_1$); 1 mM ATP; and 25 mM MgCl$_2$ in 200 mM HEPES, pH 7.5. Assay conditions for unphosphorylated VEGF-R2D50 (indicated as FLVK in the tables) were the following: 1 mM PEP; 250 mM NADH; 50 units of LDH/mL; 20 units of PK/mL; 5 mM DTT; 20 mM poly(E$_4$Y$_1$); 3 mM ATP; and 60 mM MgCl$_2$ and 2 mM MnCl$_2$ in 200 mM HEPES, pH 7.5. Assays were initiated with 5 to 40 nM of enzyme. K$_i$ values were determined by measuring enzyme activity in the presence of varying concentrations of test compounds. The percent inhibition at 50 nm (% inhibition@50 nm) was determined by linear least-squares regression analysis of absorpbance as a function of time. The binding inhibitions were fitted to equation as described by Morrison. The data were analyzed using Enzyme Kinetic and Kaleidagraph software.

Example B

FGF-R Assay

The spectrophotometric assay was carried out as described above for VEGF-R2, except for the following changes in concentration: FGF-R=50 nM, ATP=2 mM, and poly(E4Y1)=15 mM.

Example C

HUVEC+VEGF Proliferation Assay

This assay determines the ability of a test compound to inhibit the growth factor-stimulated proliferation of human umbilical vein endothelial cells ("HUVEC"). HUVEC cells (passage 3–4, Clonetics, Corp.) were thawed into EGM2 culture medium (Clonetics Corp) in T75 flasks. Fresh EGM2 medium was added to the flasks 24 hours later. Four or five days later, cells were exposed to another culture medium (F12K medium supplemented with 10% fetal bovine serum (FBS), 60 mg/mL endothelial cell growth supplement (ECGS), and 0.1 mg/mL heparin). Exponentially-growing HUVEC cells were used in experiments thereafter. Ten to twelve thousand HUVEC cells were plated in 96-well dishes in 100 ml of rich, culture medium (described above). The cells were allowed to attach for 24 hours in this medium. The medium was then removed by aspiration and 105 ml of starvation media (F12K+1% FBS) was added to each well. After 24 hours, 15 ml of test agent dissolved in 1% DMSO in starvation medium or this vehicle alone was added into each treatment well; the final DMSO concentration was 0.1%. One hour later, 30 ml of VEGF (30 ng/mL) in starvation media was added to all wells except those containing untreated controls; the final VEGF concentration was 6 ng/mL. Cellular proliferation was quantified 72 hours later by MTT dye reduction, at which time cells were exposed for 4 hours MTT (Promega Corp.). Dye reduction was stopped by addition of a stop solution (Promega Corp.) and absorbance at 595 nm was determined on a 96-well spectrophotometer plate reader.

Example D

Mouse PK Assay

The pharmacokinetics (e.g., absorption and elimination) of drugs in mice were analyzed using the following experiment. Test compounds were formulated as a suspension in a 30:70 (PEG 400: acidified $H_2O$) vehicle. This solution was administered orally (p.o.) and intraperitoneally (i.p.) at 50 mg/kg to two distinct groups (n=4) of B6 female mice. Blood samples were collected via an orbital bleed at time points: 0 hour (pre-dose), 0.5 hr, 1.0 hr, 2.0 hr, and 4.0 hr post dose. Plasma was obtained from each sample by centrifugation at 2500 rpm for 5 min. Test compound was extracted from the plasma by an organic protein precipitation method. For each time bleed, 50 µL of plasma was combined with 1.0 mL of acetonitrile, vortexed for 2 min. and then spun at 4000 rpm for 15 min. to precipitate the protein and extract out the test compound. Next, the acetonitrile supernatant (the extract containing test compound) was poured into new test tubes and evaporated on a hot plate (25° C.) under a steam of $N_2$ gas. To each tube containing the dried test compound extract, 125 µL of mobile phase (60:40, 0.025 M $NH_4H_2PO_4$+2.5 mL/L TEA:acetonitrile) was added. The test compound was resuspended in the mobile phase by vortexing and more protein was removed by centrifugation at 4000 rpm for 5 min. Each sample was poured into an HPLC vial for test compound analysis on an Hewlett Packard 1100 series HPLC with UV detection. From each sample, 95 µL was injected onto a Phenomenex-Prodigy reverse phase C-18, 150×3.2 mm column and eluted with a 45–50% acetonitrie gradient run over 10 min. Test-compound plasma concentrations (µg/mL) were determined by a comparison to standard curve (peak area vs. conc. µg/mL) using known concentrations of test compound extracted from plasma samples in the manner described above. Along with the standards and unknowns, three groups (n=4) of quality controls (0.25 µg/mL, 1.5 µg/mL, and 7.5 µg/mL) were run to insure the consistency of the analysis. The standard curve had an $R_2$>0.99 and the quality controls were all within 10% of their expected values. The quantitated test samples were plotted for visual display using Kalidagraph software and their pharmacokinetic parameters were determined using WIN NONLIN software.

Example E

Human Liver Microsome (HLM) Assay

Compound metabolism in human liver microsomes was measured by LC-MS analytical assay procedures as follows. First, human liver microsomes (HLM) were thawed and diluted to 5 mg/mL with cold 100 mM potassium phosphate ($KPO_4$) buffer. Appropriate amounts of $KPO_4$ buffer, NADPH-regenerating solution (containing B-NADP, glucose-6-phosphate, glucose-6-phosphate dehydrogenase, and $MgCl_2$), and HLM were preincubated in 13×100 mm glass tubes at 37° C. for 10 min. (3 tubes per test compound—triplicate). Test compound (5 µM final) was added to each tube to initiate reaction and was mixed by gentle vortexing, followed by incubation at 37° C. At t=0, and 2 h, a 250-uL sample was removed from each incubation tube to separate 12×75 mm glass tubes containing 1 mL ice-cold acetonitrile with 0.05 µM reserpine. Samples were centrifuged at 4000 rpm for 20 min. to precipitate proteins and salt (Beckman Allegra 6KR, S/N ALK98D06, #634). Supernatant was transferred to new 12×75 mm glass tubes and evaporated by Speed-Vac centrifugal vacuum evaporator. Samples were reconstituted in 200 µL 0.1% formic acid/acetonitrile (90/10) and vortexed vigorously to dissolve. The samples were then transferred to separate polypropylene microcentrifuge tubes and centrifuged at 14000×g for 10 min. (Fisher Micro 14, S/N M0017580). For each replicate (#1–3) at each timepoint (0 and 2 h), an aliquot sample of each test compound was combined into a single HPLC vial insert (6 total samples) for LC-MS analysis, which is described below.

The combined compound samples were injected into the LC-MS system, composed of a Hewlett-Packard HP1100 diode array HPLC and a Micromass Quattro II triple quadruple mass spectrometer operating in positive electrospray SIR mode (programmed to scan specifically for the molecular ion of each test compound). Each test compound peak was integrated at each timepoint. For each compound, peak area at each timepoint (n=3) was averaged, and this mean peak area at 2 h was divided by the average peak area at time 0 hour to obtain the percent test compound remaining at 2 h.

Example F

KDR (YEGFR2) Phosphorylation in PAE-KDR Cells Assay

This assay determines the ability of a test compound to inhibit the autophosphorylation of KDR in porcine aorta endothelial (PAE)-KDR cells. PAE cells that overexpress human KDR were used in this assay. The cells were cultured in Ham's F12 media supplemented with 10% fetal bovine serum (FBS) and 400 ug/mL G418. Thirty thousands cells were seeded into each well of a 96-well plate in 75 mL of growth media and allowed to attach for 6 hours at 37° C.

Cells were then exposed to the starvation media (Ham's F12 media supplemented with 0.1% FBS) for 16 hours. After the starvation period was over, 10 mL of test agent in 5% DMSO in starvation media were added to the test wells and 10 mL of the vehicle (5% DMSO in starvation media) were added into the control wells. The final DMSO concentration in each well was 0.5%. Plates were incubated at 37° C. for 1 hour and the cells were then stimulated with 500 ng/ml VEGF (commercially available from R & D System) in the presence of 2 mM Na$_3$VO$_4$ for 8 minutes. The cells were washed once with 1 mm Na$_3$VO$_4$ in HBSS and lysed by adding 50 mL per well of lysis buffer. One hundred mL of dilution buffer were then added to each well and the diluted cell lysate was transferred to a 96-well goat ant-rabbit coated plate (commercially available from Pierce) which was pre-coated with Rabbit anti Human Anti-flk-1 C-20 antibody (commercially available from Santa Cruz). The plates were incubated at room temperature for 2 hours and washed seven times with 1% Tween 20 in PBS. HRP-PY20 (commercially available from Santa Cruz) was diluted and added to the plate for a 30-minute incubation. Plates were then washed again and TMB peroxidase substrate (commercially available from Kirkegaard & Perry) was added for a 10-minute incubation. One hundred mL of 0.09 N H$_2$SO$_4$ was added to each well of the 96-well plates to stop the reaction. Phosphorylation status was assessed by spectrophotometer reading at 450 nm. IC$_{50}$ values were calculated by curve fitting using a four-parameter analysis.

Example G

PAE-PDGFRb Phosphorylation in PAE-PDGFRB Cells Assay

This assay determines the ability of a test compound to inhibit the autophosphorylation of PDGFRb in porcine aorta endothelial (PAE)-PDGFRb cells. PAE cells that overexpress human PDGFRb were used in this assay. The cells were cultured in Ham's F12 media supplemented with 10% fetal bovine serum (FBS) and 400 ug/ml G418. Twenty thousands cells were seeded in each well of a 96-well plate in 50 mL of growth media and allowed to attach for 6 hours at 37° C. Cells were then exposed to the starvation media (Ham's F12 media supplemented with 0.1% FBS) for 16 hours. After the starvation period was over, 10 mL of test agent in 5% DMSO in starvation media were added to the test wells and 10 mL of the vehicle (5% DMSO in starvation media) were added into the control wells. The final DMSO concentration in each well was 0.5%. Plates were incubated at 37° C. for 1 hour and the cells were then stimulated with 1 mg/mL PDGF-BB (R & D System) in the presence of 2 mM Na$_3$VO$_4$ for 8 minutes. The cells were washed once with 1 mm Na$_3$VO$_4$ in HBSS and lysed by adding 50 mL per well of lysis buffer. One hundred mL of dilution buffer were then added to each well and the diluted cell lysate was transferred to a 96-well goat ant-rabbit coated plate (Pierce), which was pre-coated with Rabbit anti Human PDGFRb antibody (Santa Cruz). The plates were incubated at room temperature for 2 hours and washed seven times with 1% Tween 20 in PBS. HRP-PY20 (Santa Cruz) was diluted and added to the plate for a 30-minute incubation. Plates were then washed again and TMB peroxidase substrate (Kirkegaard & Perry) was added for a 10-minute incubation. One hundred mL of 0.09 N H$_2$SO$_4$ was added into each well of the 96well plate to stop the reaction. Phosphorylation status was assessed by spectrophotometer reading at 450 nm. IC$_{50}$ values were calculated by curve fitting using a four-parameter analysis.

The results of the testing of the compounds using various assays are summarized in Table 1.

TABLE 1

| Example Number | FLVK Ki<br>A = >10 nM<br>B = 1–10 nM<br>C = <1 nM<br>NT = not tested | FGF-P (% inh @ 50 nM)<br>A = 0–5%<br>B = 5–10%<br>C = >10%<br>NT = not tested | HUVEC + VEGF<br>IC50 A = >10 nM<br>B = 1–10 nM<br>C = <1 nM<br>NT = not tested |
|---|---|---|---|
| 1 | C | A | NT |
| 2 | A | A | NT |
| 3 | NT | A | C |
| 4 | C | B | B |
| 5 | NT | A | NT |
| 6 | C | B | A |
| 7 | C | B | C |
| 8 | B | A | A |
| 9 | C* | B | C |
| 10 | C | A | C |
| 11 | C | A | A |
| 12 | C | B | A |
| 13 | C | B | A |
| 14 | C | B | B |
| 15 | C | A | C |
| 16 | B | A | A |
| 17 | C | C | A |
| 18 | C | B | A |
| 19 | B | A | A |
| 20 | B | A | B |
| 21 | NT | A | B |
| 22 | NT | A | C |
| 23 | C | A | C |
| 24 | C | A | B |
| 25 | C | B | B |
| 26 | A | NT | NT |
| 27 | C | A | B |
| 28 | C | B | C |
| 29 | B | A | A |
| 30 | C | A | B |
| 31 | C | A | C |
| 32 | B | A | A |
| 33 | C* | A | A |
| 34 | NT | NT | NT |
| 35 | A | A | NT |
| 36 | NT | A | A |
| 37 | NT | NT | NT |
| 38 | NT | A | A |
| 39 | NT | A | NT |
| 40 | A | A | NT |
| 41 | B | B | B |
| 42 | A | A | NT |
| 43 | NT | NT | NT |
| 44 | NT | NT | NT |
| 45 | NT | NT | NT |
| 46 | NT | NT | NT |
| 47 | NT | NT | NT |
| 48 | NT | NT | NT |
| 49 | C | C | B |
| 50 | B | C | A |
| 51 | B | A | A |
| 52 | B | C | A |
| 53 | C | A | B |
| 54 | A | A | NT |
| 55 | C | A | C |
| 56 | NT | A | A |
| 57 | A | A | NT |
| 58 | A | A | NT |
| 59 | A | A | NT |
| 60 | B | A | A |
| 61 | B | A | A |
| 62 | B | A | A |
| 63 | A | A | NT |
| 64 | A | A | NT |
| 65 | A | A | NT |
| 66 | A | A | A |

TABLE 1-continued

| Example Number | FLVK Ki<br>A = >10 nM<br>B = 1–10 nM<br>C = <1 nM<br>NT = not tested | FGF-P (% inh @ 50 nM)<br>A = 0–5%<br>B = 5–10%<br>C = >10%<br>NT = not tested | HUVEC + VEGF<br>IC50 A = >10 nM<br>B = 1–10 nM<br>C = <1 nM<br>NT = not tested |
|---|---|---|---|
| 67 | A | A | NT |
| 68 | A | A | NT |
| 69 | A | A | A |
| 70 | A | B | NT |
| 71 | A | A | NT |
| 72 | NT | A | NT |
| 73 | NT | A | NT |
| 74 | B | A | A |
| 75 | A | A | NT |
| 76 | B | A | A |
| 77 | A | A | NT |
| 78 | A | C | NT |
| 79 | A | A | NT |
| 80 | A | B | NT |
| 81 | NT | NT | NT |
| 82 | A | A | NT |
| 83 | A | B | NT |
| 84 | A | B | NT |
| 85 | NT | NT | NT |
| 86 | B | A | C |
| 87 | B | A | A |

Examples of Pharmaceutical Formulations

The exemplary compounds described above may be formulated into pharmaceutical compositions according to the following general examples.

Example I

Parenteral Composition

To prepare a parenteral pharmaceutical composition suitable for administration by injection, 100 mg of a water-soluble salt of a compound of Formula I is dissolved in DMSO and then mixed with 10 mL of 0.9% sterile saline. The mixture is incorporated into a dosage unit form suitable for administration by injection.

Example II

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A compound represented by Formula (I):

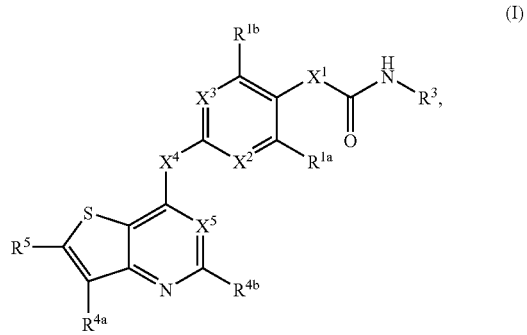

wherein
(a) $X^1$ is O or $CR^{2a}R^{2b}$;
(b) $X^2$ is $CR^{1c}$;
(c) $X^3$ is $CR^{1d}$;
(d) $X^4$ is O;
(e) $X^5$ is $CR^{4c}$;
each of $R^{1a}$, $R^{1b}$, $R^{1c}$, and $R^{1d}$ is independently selected from the group consisting of hydrogen, halogen, $(C_1-C_6)$alkoxy, $(C_1-C_6)$alkyl, $(C_1-C_6)$fluoroalkoxy, and $(C_1-C_6)$fluoroalkyl;
(g) each of $R^{2a}$ and $R^{2b}$ is independently selected from H, halogen, or a moiety, (optionally substituted with 1 to 3 independently selected $Y^1$ groups) selected from the group consisting of $(C_1-C_6)$alkoxy, $(C_1-C_6)$alkylamine and $(C_1-C_6)$alkyl, wherein any number of the hydrogen atoms on the $(C_1-C_6)$alkoxy and $(C_1-C_6)$alkyl groups may be optionally replaced with F; or $R^{2a}$ and $R^{2b}$ together can be oxo or a moiety (optionally substituted with 1 to 3 independently selected $Y^1$ groups) selected from the group consisting of $(C_3-C_6)$cycloalkyl, 3–6 membered heterocycloalkyl and =CH—$(C_1-C_5)$alkyl;
(h) $R^3$ is H or a moiety (optionally substituted with 1–3 independently selected $Y^2$ groups) selected from the group consisting of —$(CZ^1Z^2)_s$CN, —$(CZ^1Z^2)_s$—$(C_3-C_8)$cycloalkyl, —$(CZ^1Z^2)_s$—$(C_5-C_8)$cycloalkenyl, $(C_2-C_6)$alkenyl, $(C_2-C_6)$alkynyl, —$(CZ^1Z^2)_s$-aryl, —$(CZ^1Z^2)_s$-heterocycle, and $(C_1-C_8)$alkyl, where s is 0, 1, 2, or 3, and wherein when s is 2 or 3, the —$CZ^1Z^2$ units may be the same or different;
(i) each of $R^{4a}$, $R^{4b}$, and $R^{4c}$ is independently selected from the group consisting of H, F, Cl, $CF_3$, $CH_3$, $OCH_3$, and $OCF_3$;
(j) $R^5$ is selected from the group consisting of hydrogen, nitro, halogen, azido, —$NR^{6a}R^{6b}$, —$NR^{6a}SO_2R^{6b}$, —$NR^{6a}C(O)R^{6b}$, —$OC(O)R^{6b}$, —$NR^{6a}C(O)OR^{6b}$, —$OC(O)NR^{6a}R^{6b}$, —$OR^{6a}$, —$SR^{6a}$, —$S(O)R^{6a}$, —$SO_2R^{6a}$, —$SO_3R^{6a}$, —$SO_2NR^{6a}R^{6b}$, —$COR^{6a}$, —$CO_2R^{6b}$, —$CONR^{6a}R^{6b}$, —$(C_1-C_4)$fluoroalkyl, —$(C_1-C_4)$fluoroalkoxy, —$(CZ^3Z^4)_t$CN, and a moiety selected from the group consisting of —$(CZ^3Z^4)_t$-aryl, —$(CZ^3Z^4)_t$-heterocycle, $(C_2-C_6)$alkynyl, —$(CZ^3Z^4)_t$—$(C_3-C_6)$cycloalkyl, —$(CZ^3Z^4)_t$—$(C_5-C_6)$cycloalkenyl, $(C_2-C_6)$alkenyl, and $(C_1-C_6)$alkyl, which is optionally substituted with 1 to 3 independently selected $Y^2$ groups, where t is 0, 1, 2, or 3, and wherein when t is 2 or 3, the $CZ^3Z^4$ units may be the same or different;

(k) each $R^{6a}$ and $R^{6b}$ is independently selected from the group consisting of hydrogen and a moiety selected from the group consisting of $-(CZ^5Z^6)_u-(C_3-C_6)$ cycloalkyl, $-(CZ^5Z^6)_u-(C_5-C_6)$cycloalkenyl, $-(CZ^5Z^6)_u$-aryl, $-(CZ^5Z^6)_u$-heterocycle, $(C_2-C_6)$alkenyl, and $(C_1-C_6)$alkyl, which is optionally substituted with 1 to 3 independently selected $Y^3$ groups, where u is 0, 1, 2, or 3, and wherein when u is 2 or 3, the $CZ^5Z^6$ units may be the same or different, or $R^{6a}$ and $R^{6b}$ taken together can with adjacent atoms form a heterocycle;

(l) each $Z^1$, $Z^2$, $Z^3$, $Z^4$, $Z^5$, and $Z^6$ is independently selected from the group consisting of H, F, and $(C_1-C_6)$ alkyl, or each $Z^1$ and $Z^2$, $Z^3$ and $Z^4$, or $Z^5$ and $Z^6$ are selected together to form a carbocycle, or two $Z^1$, $Z^3$ or $Z^3$ groups on adjacent carbon atoms are selected together to optionally form a carbocycle; and (m) each $Y^1$ is independently selected from the group consisting of halogen, cyano, nitro, azido, $-OH$, $-NH_2$, $(C_1-C_6)$alkoxy, $(C_1-C_6)$alkylamino, $(C_1-C_6)$ dialkylamino, $(C_1-C_6)$alkyl, $(C_2-C_6)$alkenyl, $(C_2-C_6)$ alkynyl, $(C_1-C_6)$haloalkyl, $(C_1-C_6)$haloalkoxy, $-(C_3-C_6)$cycloalkyl;

(n) each $Y^2$ and $Y^3$ is independently selected and
  (i) is selected from the group consisting of halogen, cyano, nitro, tetrazolyl, guanidino, amidino, methylguanidino, azido, $-C(O)Z^7$, $-OC(O)NH_2$, $-OC(O)NHZ^7$, $-OC(O)NZ^7Z^8$, $-NHC(O)Z^7$, $-NHC(O)NH_2$, $-NHC(O)NHZ^7$, $-NHC(O)NZ^7Z^8$, $-C(O)OH$, $-C(O)OZ^7$, $-C(O)NH_2$, $-C(O)NHZ^7$, $-C(O)NZ^7Z^8$, $-P(O)_3H_2$, $-P(O)_3(Z^7)_2$, $-S(O)_3H$, $-S(O)Z^7$, $-S(O)_2Z^7$, $-S(O)_3Z^7$, $-Z^7$, $-OZ^7$, $-OH$, $-NH_2$, $-NHZ^7$, $-NZ^7Z^8$, $-C(=NH)NH_2$, $-C(=NOH)NH_2$, $-N$-morpholino, $(C_2-C_6)$alkenyl, $(C_2-C_6)$alkynyl, $(C_1-C_6)$ haloalkyl, $(C_2-C_6)$haloalkenyl, $(C_2-C_6)$haloalkynyl, $(C_1-C_6)$haloalkoxy, $-(CZ^9Z^{10})_rNH_2$, $-(CZ^9Z^{10})_r$ $NHZ^3$, $-(CZ^9Z^{10})_rNZ^7Z^8$, $-X^6(CZ^9Z^{10})_r-$ $(C_3-C_8)$ cycloalkyl, $-X^6(CZ^9Z^{10})_r-(C_5-C_8)$cycloalkenyl, $-X^6(CZ^9Z^{10})_r$-aryl, and $-X^6(CZ^9Z^{10})_r$-heterocycle; r is 1, 2, 3, or 4; $X^6$ is O, S, NH, $-C(O)-$, $-C(O)NH-$, $-C(O)O-$, $-S(O)-$, $-S(O)_2-$, or $-S(O)_3-$; $Z^7$ and $Z^8$ are independently selected from the group consisting of alkyl of 1 to 12 carbon atoms, alkenyl of 2 to 12 carbon atoms, alkynyl of 2 to 12 carbon atoms, cycloalkyl of 3 to 8 carbon atoms, cycloalkenyl of 5 to 8 carbon atoms, aryl of 6 to 14 carbon atoms, heterocycle of 5 to 14 ring atoms, aralkyl of 7 to 15 carbon atoms, and heteroaralkyl of 5 to 14 ring atoms, or $Z^7$ and $Z^8$ together may optionally form a heterocycle; and $Z^9$ and $Z^{10}$ are independently selected from the group consisting of hydrogen, fluorine, alkyl of 1 to 12 carbon atoms, aryl of 6 to 14 carbon atoms, heteroaryl of about 5 to 14 ring atoms, aralkyl of 7 to 15 carbon atoms, and heteroaralkyl of 5 to 14 ring atoms, or $Z^9$ and $Z^{10}$ are selected together to form a carbocycle, or two $Z^9$ groups on adjacent carbon atoms are selected together to form a carbocycle; or
  (ii) any two $Y^2$ or $Y^3$ groups attached to adjacent carbon atoms may be selected together to be $-O[C(Z^9)(Z^{10})]_rO-$ or $-O[C(Z^9)(Z^{10})]_{r+1}-$; or
  (iii) any two $Y^2$ or $Y^3$ groups attached to the same or adjacent carbon atoms may be selected together to form a carbocycle or heterocycle;

and wherein any of the above-mentioned substituents comprising a $CH_3$ (methyl), $CH_2$ (methylene), or CH (methine) group which is not attached to a halogen, SO or $SO_2$ group or to a N, O or S atom optionally bears on said group a substituent selected from hydroxy, halogen, $(C_1-C_4)$alkyl, $(C_1-C_4)$alkoxy and $-N[(C_1-C_4)alkyl][(C_1-C_4)alkyl]$;

or a pharmaceutically acceptable salt or solvate thereof.

2. The compound according to claim 1, wherein $X^1$ is O.

3. The compound according to claim 2, wherein $X^5$ is CH.

4. The compound according to claim 1, wherein $X^1$ is $CH_2$.

5. The compound according to claim 1, wherein $X^5$ is CH.

6. The compound according to claim 5, wherein $X^1$ is $CH_2$.

7. The compound according to claim 6, wherein each of $R^{1a}$, $R^{1b}$, $R^{1c}$, and $R^{1d}$ is independently H, F, or Cl.

8. The compound according to claim 7, wherein each of $R^{4a}$, $R^{4b}$, and $R^{4c}$ is independently selected from the group consisting of H and F.

9. The compound according to claim 1, wherein $R^3$ is a $(C_1-C_8)$alkyl, optionally substituted with 1–3 independently selected $Y^2$ groups.

10. The compound according to claim 8, wherein $R^3$ is a $(C_1-C_8)$alkyl, optionally substituted with 1–3 independently selected $Y^2$ groups.

11. The compound according to claim 1, wherein $R^3$ is a heterocycle, optionally substituted with 1–3 independently selected $Y^2$ groups.

12. The compound according to claim 8, wherein $R^3$ is a heterocycle, optionally substituted with 1–3 independently selected $Y^2$ groups.

13. The compound according to claim 1, wherein $R^5$ is $-CONR^{6a}R^{6b}$.

14. The compound according to claim 1, wherein $R^5$ is a $-(CZ^3Z^4)_t$-heterocycle.

15. The compound according to claim 8, wherein $R^5$ is $-CONR^{6a}R^{6b}$.

16. The compound according to claim 8, wherein $R^5$ is $-(CZ^3Z^4)_t$-heterocycle.

17. The compound according to claim 1, wherein $X^1$ is $CR^{2a}R^{2b}$.

18. The compound according to claim 17, wherein $R^5$ is $-C(O)NR^{6a}R^{6b}$ or $-(CZ^3Z^4)_t$-heterocycle.

19. The compound according to claim 18, wherein $R^3$ is $(C_1-C_6)$alkyl or $-(CZ^1Z^2)_s$ heterocycle.

20. The compound according to claim 19, wherein $R^3$ is heteroaryl.

21. The compound according to claim 20, wherein $R^5$ is $-C(O)NR^{6a}R^{6b}$ or heteroaryl.

22. The compound according to claim 21, wherein R is $-C(O)NR^{6a}R^{6b}$ wherein $R^{6a}$ and $R^{6b}$ taken with the nitrogen atom form a heterocycle or $R^5$ is imidazolye.

23. The compound according to claim 22, wherein $R^{1a}$, $R^{1b}$, $R^{1c}$, $R^{1d}$, $R^{2a}$, $R^{2b}$, $R^{4c}$, $R^{4b}$ and $R^{4c}$ are hydrogen, F or Cl.

24. The compound according to claim 23, wherein $R^{1b}$, $R^{1c}$, $R^{1d}$, $R^{2a}$, $R^{2b}$, $R^{4a}$, $R^{4b}$ and $R^{4c}$ are hydrogen.

25. A compound selected from the group consisting of:

N-(4,6-Dimethyl-pyridin-2-yl)-2-{3-fluoro-4-[2-(1-methyl-1H-imidazol-2-yl)-thieno[3,2-b]pyridin-7-yloxy]-phenyl}-acetamide;

2-{4-[2-((3R, 4R)-3,4-Dihydroxy-pyrrolidine-1-carbonyl)-thieno 3,2-b]pyridin-7-yloxy]-phenyl}-N-(4,6-dimethyl-pyridin-2-yl)-acetamide;

2-{4-[2-((R)-3-Dimethylamino-pyrrolidine-1-carbonyl)-thieno [3,2-b]pyridin-7-yloxy]-phenyl}-N-(4,6-dimethyl-pyridin-2-yl)-acetamide;

7-{4-[(4,6-Dimethyl-pyridin-2-ylcarbamoyl)-methyl]-phenoxy}-thieno[3,2-b]pyridine-2-carboxylic acid dimethylamide;

N-(4,6-Dimethyl-pyridin-2-yl)-2-{4-[2-(1-methyl-1H-imidazol-2-yl)-thieno[3,2-b]pyridin-7-yloxy]-phenyl}-acetamide;

N-(5-Chloro-pyridin-2-yl)-2-{4-[2-(1-methyl-1H-imidazol- 2-yl)-thieno[3,2-b]pyridin-7-yloxy]-phenyl}-acetamide;

N-(4,6-Dimethyl-pyridin-2-yl)-2-{4-[2-((R)-3-hydroxy-pyrrolidine- 1-carbonyl)-thieno[3,2-b]pyridin-7-yloxy]-phenyl}-acetamide;

2-{4-[2-((R)-3-Hydroxy-pyrrolidine-1-carbonyl)-thieno[3,2-b]pyridin- 7-yloxy]-phenyl}-N-isoquinolin-3-yl-acetamide;

2-{4-[2-((R)-3-Hydroxy-pyrrolidine-1-carbonyl)-thieno[3,2-b]pyridin- 7-yloxy]-phenyl}-N-phenyl-acetamide;

2-{4-[2-(Azetidine-1-carbonyl)-thieno[3,2-b]pyridin-7-yloxy]-phenyl}-N-(4,6-dimethyl-pyridin-2-yl)-acetamide;

2-{4-[2-(Azetidine-1-carbonyl)-thieno[3,2-b]pyridin-7-yloxy]-phenyl}-N-(6-methyl-pyridin-2-yl)-acetamide;

2-{4-[2-(Azetidine-1-carbonyl)-thieno[3,2-b]pyridin-7-yloxy]-phenyl}-N-(5-trifluoromethyl-pyridin-2-yl)-acetamide;

2-{4-[2-(Azetidine-1-carbonyl)-thieno[3,2-b]pyridin-7-yloxy]-phenyl}-N-(5-chloro-pyridin-2-yl)-acetamide;

2-{4-[2-(Azetidine-1-carbonyl)-thieno[3,2-b]pyridin-7-yloxy]-phenyl}-N-(5-bromo-pyridin-2-yl)-acetamide;

2-{4-[2-(Azetidine-1-carbonyl)-thieno[3,2-b]pyridin-7-yloxy]-phenyl}-N-isoquinolin-3-yl-acetamide;

2-{4-[2-(Azetidine-1-carbonyl)-thieno[3,2-b]pyridin-7-yloxy]-2-chloro-phenyl}-N-(4,6-dimethyl-pyridin-2-yl)-acetamide;

2-{4-[2-(Azetidine-1-carbonyl)-thieno[3,2-b]pyridin-7-yloxy]-2-chloro-phenyl}-N-(5-methyl-1H-pyrazol-3-yl)-acetamide; and Butyl-carbamic acid 4-[2-(azetidine-1-carbonyl)-thieno[3,2-b]pyridin-7-yloxy]-phenyl ester;

or a pharmaceutically acceptable salt or solvate thereof.

26. A compound selected from the group consisting of:

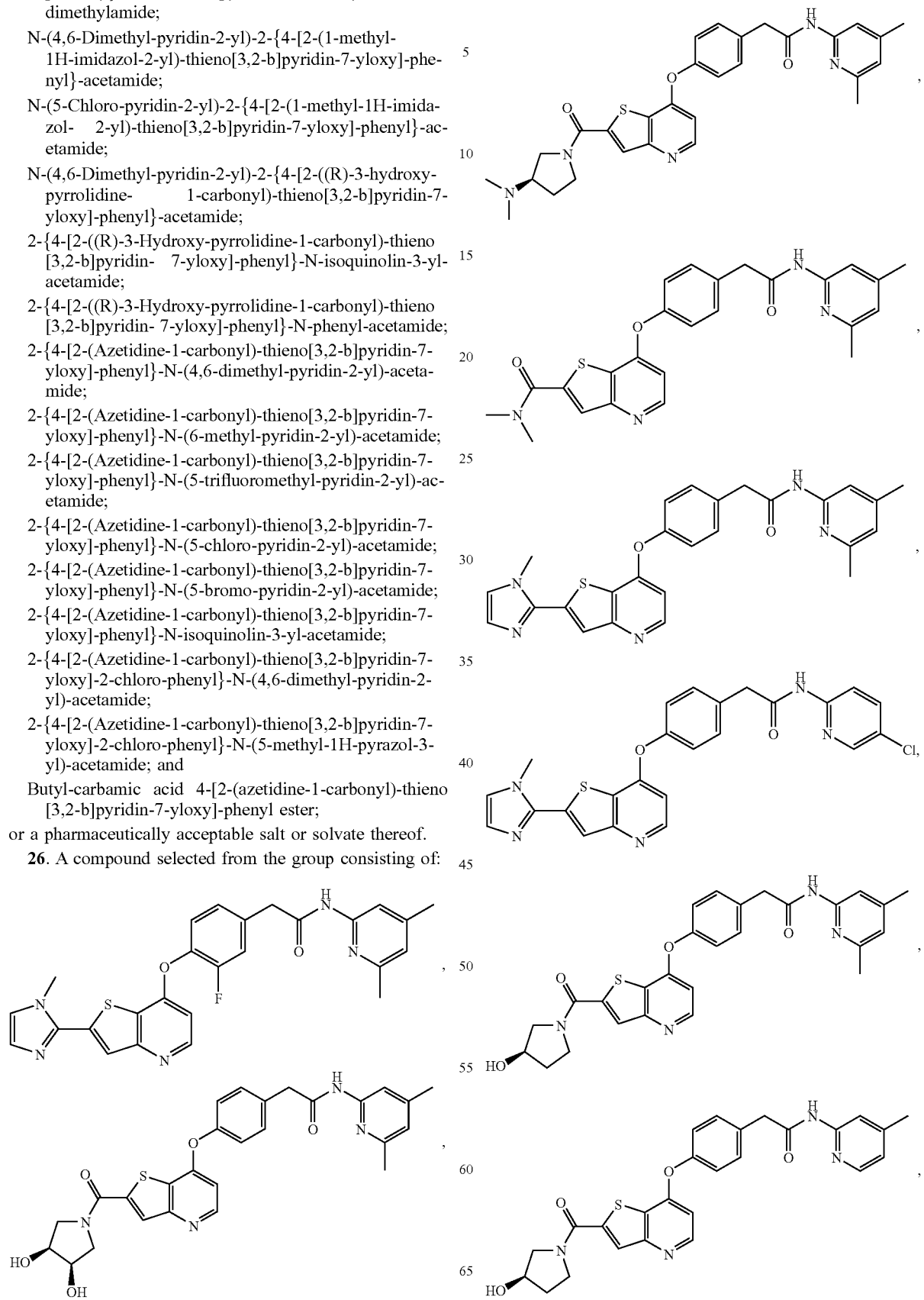

-continued
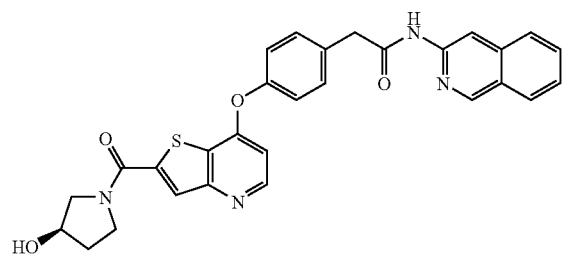
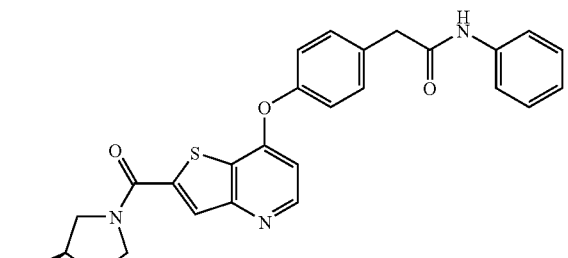
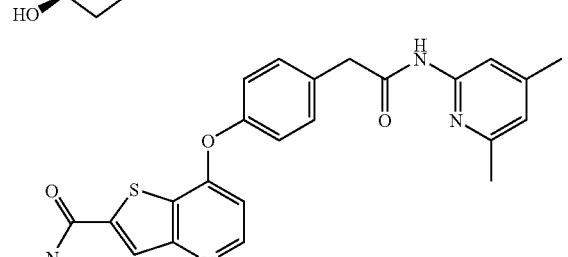
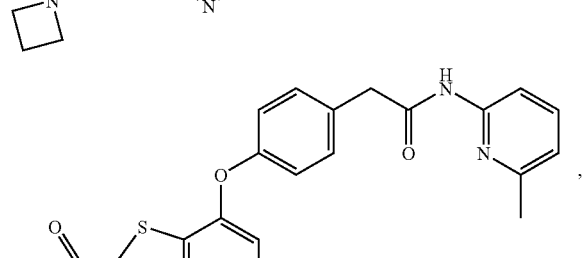
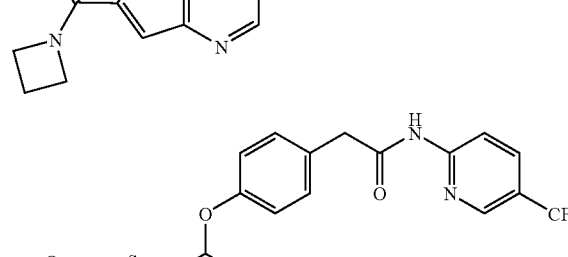
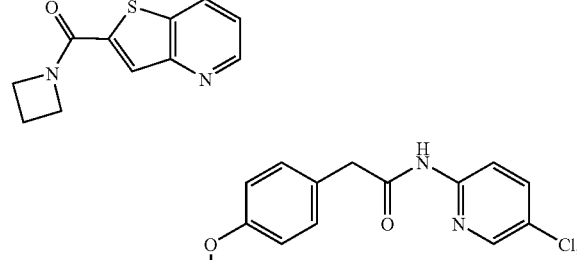
-continued
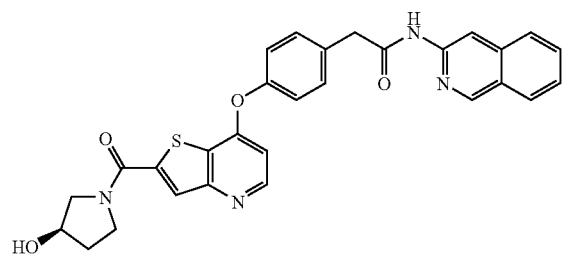
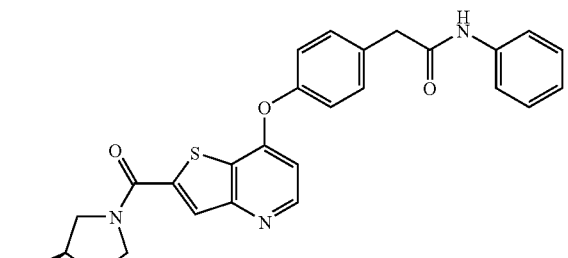
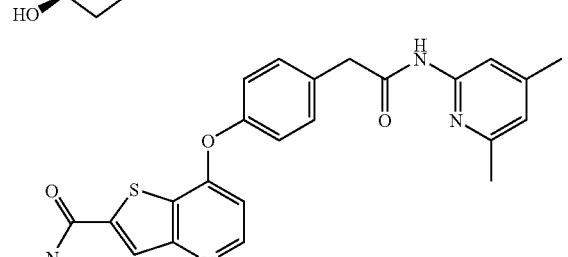
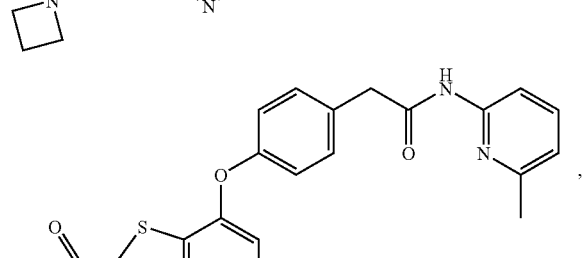
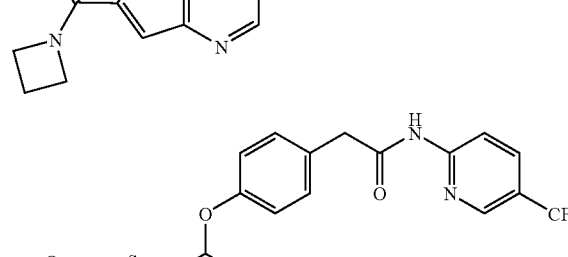, and
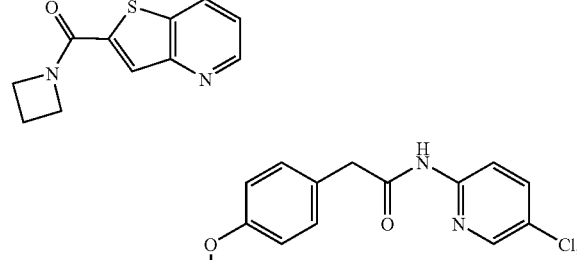
or a pharmaceutically acceptable salt or solvate thereof.
27. A pharmaceutical composition comprising a therapeutically effective amount of the compound of claim 1 and a pharmaceutically acceptable carrier.

28. A method of producing the compound of claim 1, wherein $X^1$ is $CR^{2a}R^{2b}$, comprising:

(a) reacting a carboxylic acid having the structure

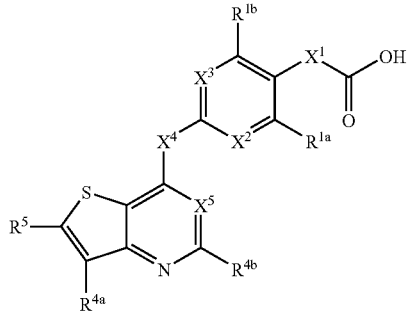

with a chlorinating agent; and (b) reacting the resulting product with $H_2N$—$R^3$.

29. The method of claim 28, wherein the chlorinating agent is selected from the group consisting of thionyl chloride, oxalyl chloride, and chlorine.

30. The method of claim 28, wherein the carboxylic acid is produced by a method comprising:

(a) reacting a compound having the formula

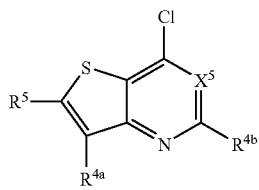

with a compound having the formula

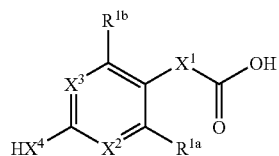

in the presence of a base.

31. A method of producing the compound of claim 1, wherein $X^1$ is O, comprising:

(a) reacting a compound of formula

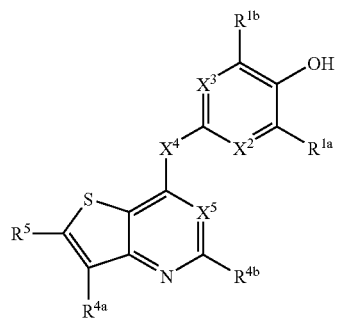

with a carbonyl electrophile; and (b) reacting the resulting product with $H_2N$—$R^3$.

32. The method of claim 31, wherein the carbonyl electrophile is phosgene.

\* \* \* \* \*